(12) United States Patent
Romo et al.

(10) Patent No.: US 11,066,379 B2
(45) Date of Patent: Jul. 20, 2021

(54) GRACILIN A AND CONGENERS AS IMMUNOSUPPRESSIVE AND NEUROPROTECTIVE AGENTS

(71) Applicants: THE TEXAS A&M UNIVERSITY SYSTEM, College Station, TX (US); UNIVERSIDADE DE SANTIAGO DE COMPOSTELA, Santiago de Compostela (ES)

(72) Inventors: Daniel Romo, Waco, TX (US); Mikail E. Abbasov, Waco, TX (US); Eva Alonso Lopez, Santiago de Compostela (ES); Maria Amparo Alfonso Rancano, Santiago de Compostela (ES); Miguel Luis Botana Lopez, Santiago de Compostela (ES)

(73) Assignees: The Texas A&M University System, College Station, TX (US); Universidade de Santiago de Compostela, Santiago de Compostela (ES)

( * ) Notice: Subject to any disclaimer, the term of this patent is extended or adjusted under 35 U.S.C. 154(b) by 0 days.

(21) Appl. No.: 16/977,444

(22) PCT Filed: Mar. 5, 2019

(86) PCT No.: PCT/US2019/020812
§ 371 (c)(1),
(2) Date: Sep. 1, 2020

(87) PCT Pub. No.: WO2019/173382
PCT Pub. Date: Sep. 12, 2019

(65) Prior Publication Data
US 2021/0002245 A1    Jan. 7, 2021

Related U.S. Application Data

(60) Provisional application No. 62/638,856, filed on Mar. 5, 2018.

(51) Int. Cl.
*C07D 307/89* (2006.01)
*C07D 307/88* (2006.01)

(52) U.S. Cl.
CPC ......... *C07D 307/89* (2013.01); *C07D 307/88* (2013.01)

(58) Field of Classification Search
CPC ........................... C07D 307/89; C07D 307/88
USPC ....................................................... 514/470
See application file for complete search history.

(56) References Cited

U.S. PATENT DOCUMENTS 6,638,417 B2    10/2003    Ishida et al.
2016/0030388 A1    2/2016    Baker et al.

OTHER PUBLICATIONS

Abbasov et al., "Simplified Immunusouppresive and Neuroprotective Agents Based on Gracilin A," Nature Chemistry 11:342-250, Apr. 2019.
Leiros et al., "Gracilins: Spongionella-Derived Promising Compounds for Alzheimer Disease," Neuropharmacology 39:285-293, 2015.
Rateb et al., "Bioactive Diterpene Derivatives from the Marine Sponge *Spongionella* sp.," Journal of Natural Products 72:1471-1472, Jul. 14, 2009.
International Search Report dated May 17, 2019, in corresponding International Application PCT/US2019/20812, filed Mar. 5, 2019, 2 pages.

*Primary Examiner* — Kristin A Vajda
(74) *Attorney, Agent, or Firm* — Christensen O'Connor Johnson Kindness PLLC

(57) ABSTRACT

Gracilin A congeners and methods for their use as immunosuppressive and neuroprotective agents.

22 Claims, 22 Drawing Sheets

GRACILIN A AND CONGENERS AS IMMUNOSUPPRESSIVE AND NEUROPROTECTIVE AGENTS

CROSS-REFERENCE TO RELATED APPLICATION

This application claims the benefit of U.S. Application No. 62/638,856, filed Mar. 5, 2018, expressly incorporated herein by reference in its entirety.

STATEMENT OF GOVERNMENT LICENSE RIGHTS

This invention was made with Government support under Contract No. GM R37 052964 awarded by the National Institutes for Health and No. CHE-1546973 awarded by the National Science Foundation. The Government has certain rights in the invention.

BACKGROUND OF THE INVENTION

The phylum *Porifera* (sponges) presents the most ancient metazoan life forms. They have a simple body plan and a limited number of cell types, and often carry a high load of bacterial symbionts or commensals. The diversity of natural products produced by sponges and associated microorganisms is very high containing members of all known biosynthetic classes. Because of this sponges are the most heavily investigated marine invertebrate phylum, and several sponge compounds or their derivatives are in the clinic or in advanced stages of clinical trials.

Previous investigations of *Spongionella* species showed it to contain different biosynthetic classes of natural product: diterpenes, nor- and bisnorditerpenes, polyhydroxylated sterols, and furanosesterterpenes. The gracilins, including the rare nor-diterpene gracilin A, was originally isolated and characterized from the Mediterranean sponge *Spongionella gracilis*. The gracilins, are considered structurally unique owing to the unusual diacetoxyhexahydrodifuro[2,3-b;3',2'-d]furan-2-one core. The cytotoxic activity of gracilins B, G-I isolated from *Spongionella* pulchella against a diverse panel of 12 human cancer cell lines has been reported, but these compounds did not progress further in preclinical evaluation. These diterpenes are structurally unique owing to the unusual diacetoxy furanose found in most members. The cytotoxic activity of gracilins B, G-I isolated from *Spongionella* pulchella against a diverse panel of 12 human cancer cell lines has been reported, but these compounds did not progress further in preclinical evaluation. The absolute configuration of gracilin A was never established, while its relative configuration was determined by X-ray analysis of the keto derivative of 9,11-dihydrogracilin A (3). Gracilin A was reported to be a potent inhibitor of phospholipase A2 (PLA2) with a 69% inactivation efficiency. It has been reported that gracilin A is mildly cytotoxic against K562 and PBMC cells, with $IC_{50}$ values of 0.6 and 0.8 M, respectively, and inhibited EGF-R by 70% at 100 µM concentration. In addition, it was shown that gracilin A mimics the effects of cyclosporin A (CsA) through inhibition of cyclophilin A (CypA) and improves Alzheimer's Disease (AD) hallmarks in vitro and in vivo.

Treatments for neurodegenerative diseases are a challenge for pharmaceutical development given the multiple and highly interconnected cellular processes implicated in neurodegeneration. For example, oxidative stress (OS), an imbalance between the release of reactive oxygen species (ROS) and cellular antioxidant defenses, has been detected in the early stages of Alzheimer's Disease (AD). Neurons are sensitive to OS due to their high oxygen consumption rate, low antioxidant capacity, and high level of polyunsaturated fatty acids. The early role of neuronal OS in AD has been linked to amyloid beta protein (Aβ) formation, mitochondrial dysfunction, microglial activation and τ-hyperphosporylation, and has led to the study of antioxidants now in Phase I or II clinical trials, such as N-acetyl-L-cysteine. The cyclophilins (Cyp) are highly conserved peptidyl-prolyl, cis-trans isomerases (PPIase) involved in protein folding and trafficking and are found in multiple cellular compartments. Cyclophilin A (CypA), the cytoplasmic isoform, has several roles in cell metabolism and energy homeostasis including the calcineurin-mediated activation of pro-inflammatory genes that encode cytokines with enhanced expression in inflammation and cancer. The use of small molecules that selectively block the inflammation-related functions of CypA, while leaving other functions unaffected, is an important pharmacological strategy leading to effective immunosuppressive agents. Cyclophilin D is a mitochondrial isoform that translocates to form the mitochondrial permeability transition pore (mPTP) and this activity correlates with mitochondrial dysfunction observed in AD leading to neuronal death. Furthermore, mitochondrial amyloid-beta protein (AP) has been implicated in CypD-mediated formation of PTP which leads to ROS generation, intracellular calcium concentration disruption, release of pro-apoptotic factors and ultimately cell death. CypD deficiency was correlated to resistance to both Aβ and $Ca^{2+}$-induced mitochondrial swelling and permeability and enhanced cognition and memory in an AD mouse model. Thus, small molecules that selectively inhibit the activity of CypD may be used for AD. CsA does not display the desired selectivity for CypD and this large macrocyclic peptide is not blood-brain barrier permeable. Therefore, CypD inhibitors devoid of immunosuppressive activity through binding to CypA but with the desired mitochondrial effect and BBB permeability could be an approach to AD.

Despite the advances in the development of immunosuppressive and neuroprotective agents noted above, a need exists for simplified gracilin A derivatives with high affinity for CypA with utility as immunosuppressants and other derivatives that demonstrate significant selectivity between CypA and CypD demonstrating their potential as neuroprotective agents devoid of immunosuppressive effects. The present invention seeks to fulfill this need and provides further related advantages.

SUMMARY OF THE INVENTION

The present invention provides gracilin A congeners and methods for using the gracilin A congeners as immunosuppressive and neuroprotective agents.

In one aspect, the invention provides gracilin A congeners. In certain embodiments, the invention provides a compound having the formula:

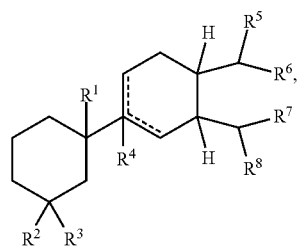

or a stereoisomer or racemate thereof, wherein:
$R^1$, $R^2$, and $R^3$ are independently H or C1-C3 alkyl;
$R^4$ is H, OH, OAc, or absent;
$R^5$ and $R^8$ are independently H or OAc;
$R^6$ and $R^7$ are H or $R^6$ and $R^7$, taken together, are O; and
the dashed line denotes a bond or absence of a bond with the proviso that only one dashed line is a bond, and with a further proviso that both dashed lines denote absence of a bond when $R^4$ is H, OH, or OAc.

In another aspect of the invention, methods for suppressing an immune response in a subject are provided. In certain embodiments, the invention provides a method for suppressing an immune response in a subject, the method comprising administering to a subject in need thereof an effective amount of a compound having the formula:

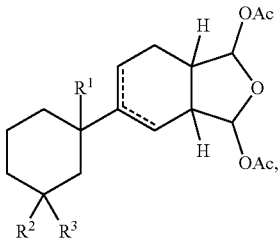

or a stereoisomer or racemate thereof, wherein:
$R^1$, $R^2$, and $R^3$ are independently H or C1-C3 alkyl, and the dashed line denotes a bond or an absence of a bond, with the proviso that only one dashed line is a bond.

In a further aspect, methods for treating a neurodegenerative disease in a subject are provided. In certain embodiments, the invention provides a method for treating a neurodegenerative disease in a subject, the method comprising administering to a subject in need thereof an effective amount of a compound having the formula:

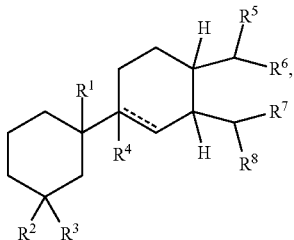

or a stereoisomer or racemate thereof, wherein:
$R^1$, $R^2$, and $R^3$ are independently H or C1-C3 alkyl;
$R^4$ is H, OH, OAc, or absent;
$R^5$ and $R^8$ are independently H or OAc;
$R^6$ and $R^7$ are H or $R^6$ and $R^7$, taken together, are O; and
the dashed line denotes a bond when $R^4$ is absent, or absence of a bond when $R^4$ is H, OH, or OAc.

In other aspects, the invention provides pharmaceutical compositions that include a compound of the invention and a pharmaceutically acceptable carrier, the use of a compound of the invention as an immunosuppressive agent, and the use of a compound of the invention as a neuroprotective agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 1A illustrates Stage I: synthesis of a highly simplified analogue bearing the proposed pharmacophore. FIG. 1B illustrates Stage II: assembly of the cis-fused, 6,5-bicyclic core 15a of gracilin A through an enantioselective, organocatalytic Diels-Alder/lactonization cascade and manipulation to a simplified bicyclic analog. FIG. 1C illustrates Stage III: annulation of the natural and a simplified cyclohexyl moiety. FIG. 1D illustrates SAR profile gap filling: alternate oxidation states of the original bis-acetoxy furanose and further simplified cyclohexyl substituents.

DETAILED DESCRIPTION OF THE INVENTION

Figure 1A:
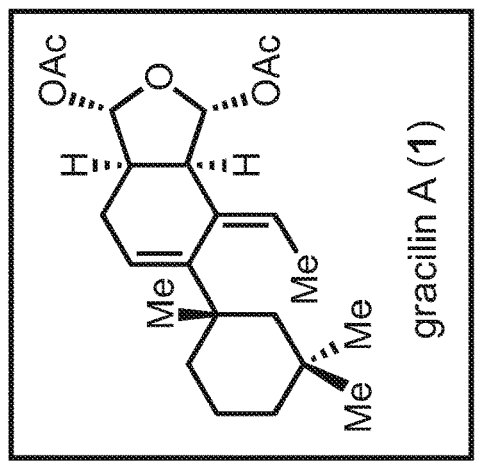
FIGS. 1A-1D illustrate the synthesis of gracilin A derivatives: Stages I-III and Stage IV (SAR profile gap filling).
Figure 1A:
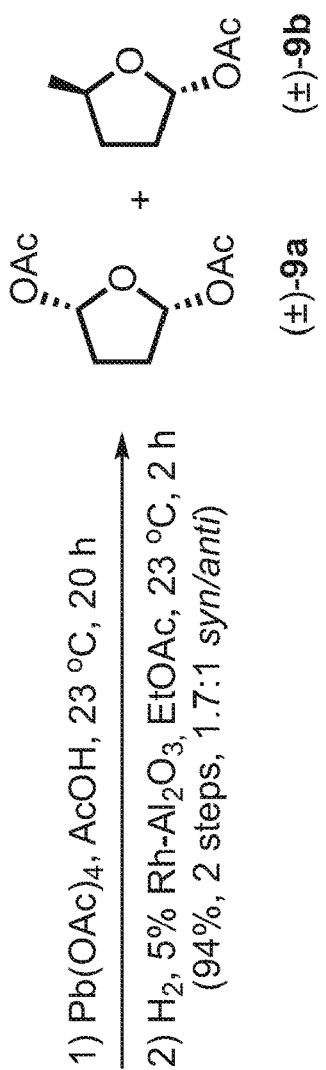
Figure 1A:
Figure 1B:
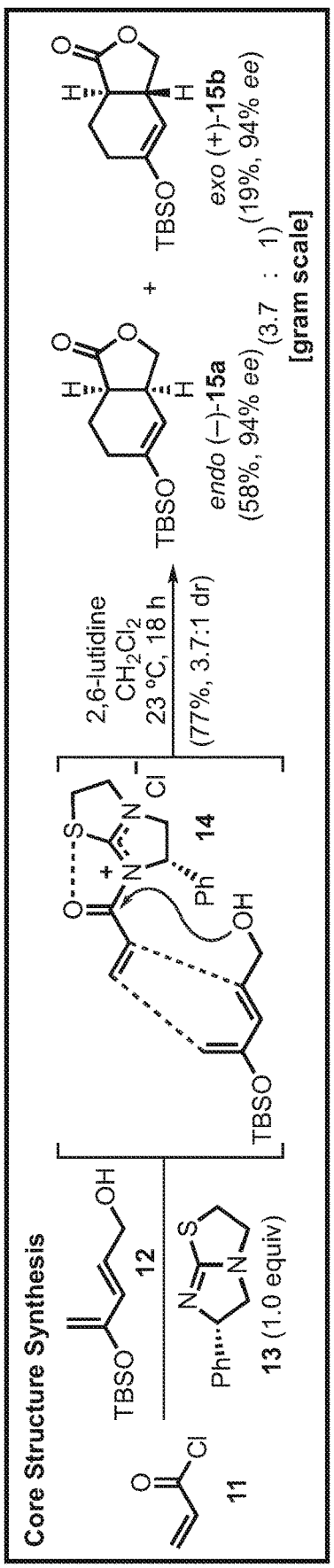
Figure 1B:
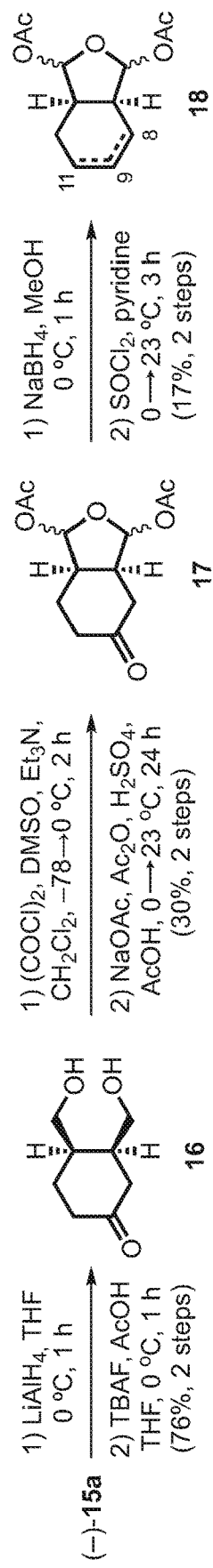
Figure 1C:
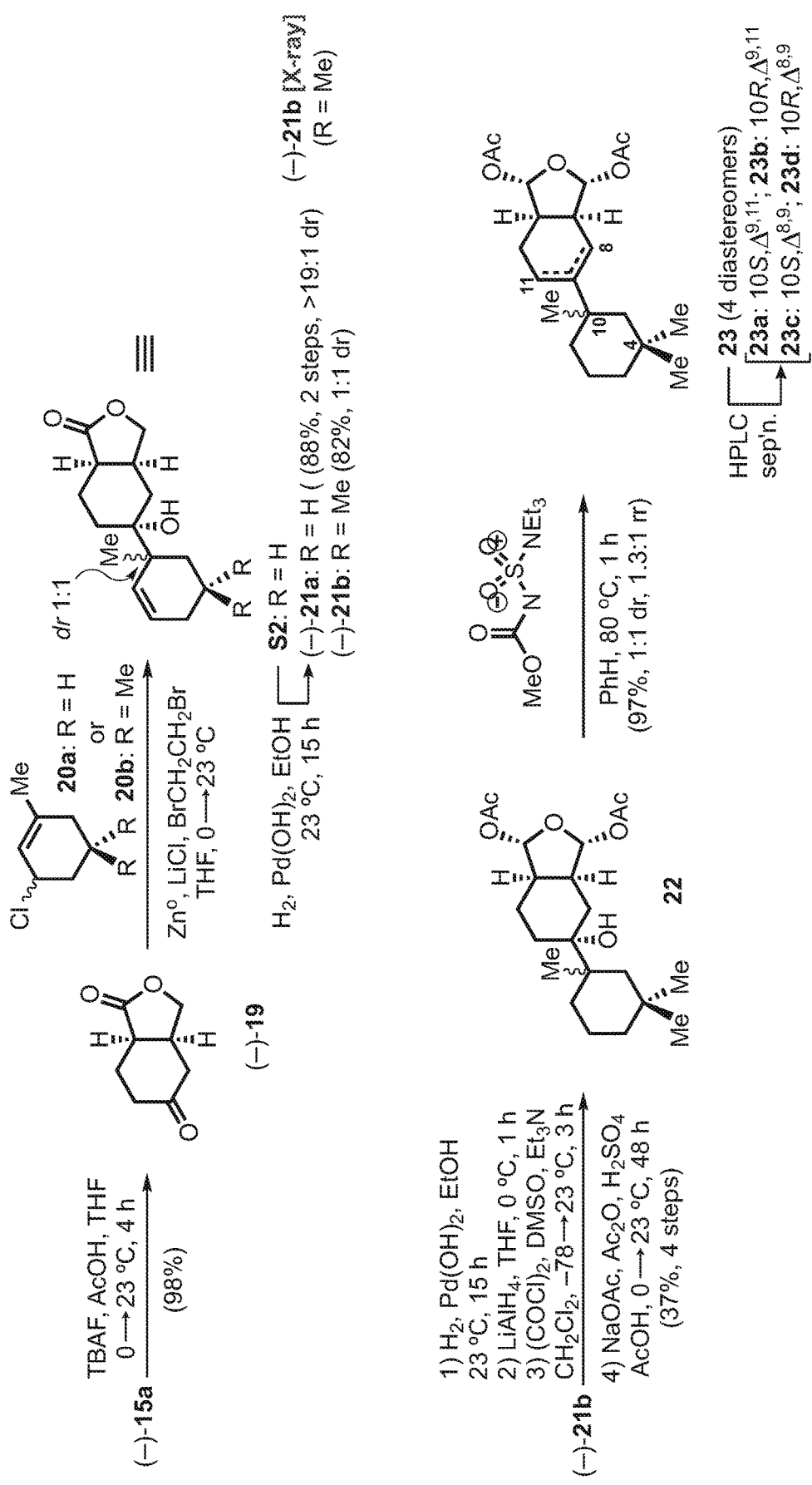

The present invention relates to gracilin A and its congeners and methods for using gracilin A and its congeners as immunosuppressive and neuroprotective agents.

In one aspect, the invention provides gracilin A congeners. As used herein, the term "gracilin A congener" refers to chemical substances related to gracilin A by origin, structure, or function. The terms "gracilin A congener" and "gracilin A derivative" are used interchangeably.

The following is a description of aspects and embodiments of the invention.

In one aspect, the invention provides gracilin A congeners.

In certain embodiments, the invention provides a compound having the formula:

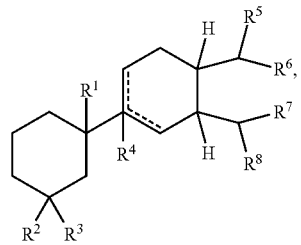

or a stereoisomer or racemate thereof, wherein:

R$^1$, R$^2$, and R$^3$ are independently H or C1-C3 alkyl;

R$^4$ is H, OH, OAc, or absent;

R$^5$ and R$^8$ are independently H or OAc;

R$^6$ and R$^7$ are H or R$^6$ and R$^7$, taken together, are O; and the dashed line denotes a bond or absence of a bond with the proviso that only one dashed line is a bond, and with a further proviso that both dashed lines denote absence of a bond when R$^4$ is H, OH, or OAc.

In certain of these embodiments, the compound is

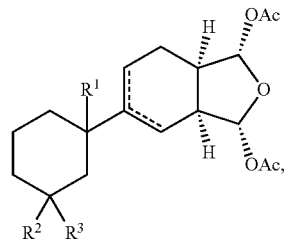

or a stereoisomer or racemate thereof.

In certain of these embodiments, the compound is

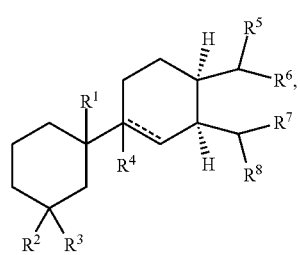

or a stereoisomer or racemate thereof.

Representative gracilin A congeners of the invention include compounds of formulae 22, 23a, 23b, 23c, 23d, 27a, 27b, A1, 29a, A1, A2, and A3:

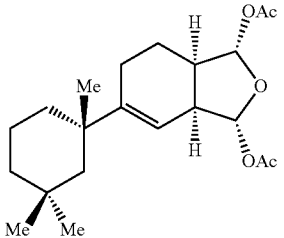
23c

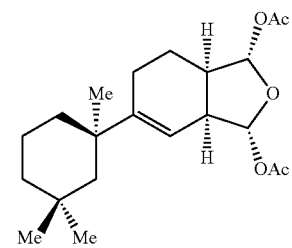
23d

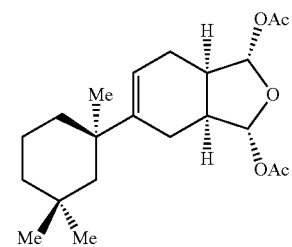
23b

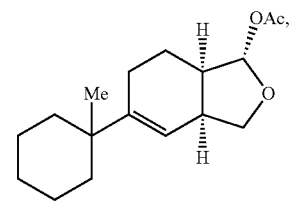
27a

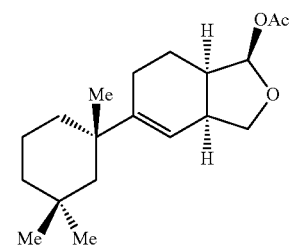
A1

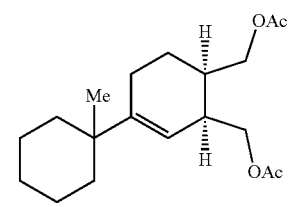
27b

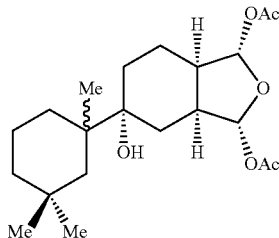
22

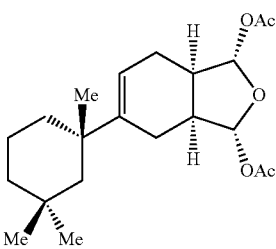
23a

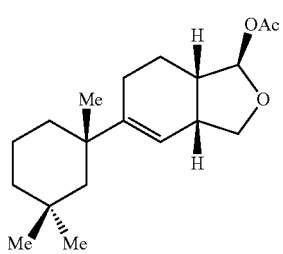
29a

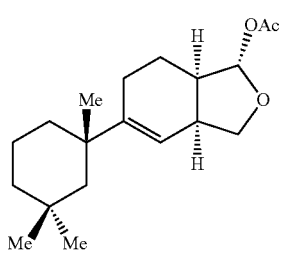
A2

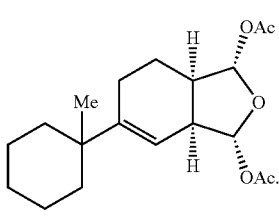
A3

As used herein, the term "stereoisomers" refers to molecules that have the same molecular formula and sequence of bonded atoms but differ in the three-dimensional arrangement of their atoms. Stereoisomers include enantiomers, diastereomers, and mixtures thereof, including racemic mixtures. The term "enantiomers" refers to two stereoisomers that are mirror images of each other and are non-superimposable. Diastereomers are stereoisomers not related through a reflection operation and include meso compounds, cis-trans isomers, E-Z isomers, and non-enantiomeric optical isomers.

All technical and scientific terms used herein have the same meaning as commonly understood by a person of ordinary skill in the art, unless noted otherwise.

In another aspect of the invention, pharmaceutical compositions of gracilin A congeners are provided. In certain embodiments, the compositions include a pharmaceutically acceptable carrier and a gracilin A congener of the invention.

In further aspects, the present invention provides methods for using gracilin A and its congeners as immunosuppressive and neuroprotective agents.

In one further aspect, the invention provides a method for suppressing an immune response in a subject, the method comprising administering to a subject in need thereof an effective amount of a compound having the formula:

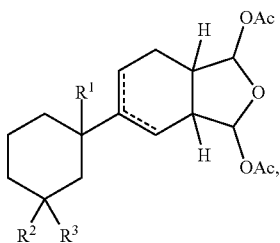

or a stereoisomer or racemate thereof, wherein:

$R^1$, $R^2$, and $R^3$ are independently H or C1-C3 alkyl, and the dashed line denotes a bond or an absence of a bond, with the proviso that only one dashed line is a bond.

In certain embodiments of the method, the compound is:

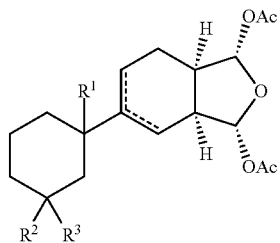

or a stereoisomer or racemate thereof.

Representative compounds useful in the method include:

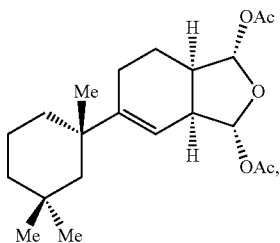

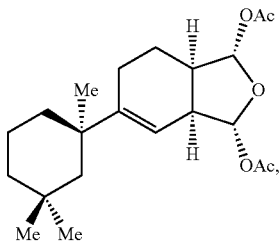

-continued

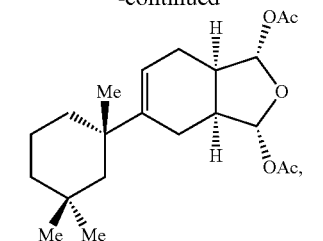

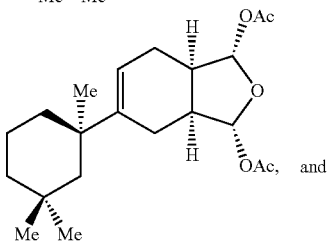

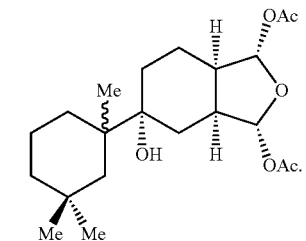

In certain embodiments of the method, the subject has been diagnosed as suffering from an autoimmune disease.

In certain embodiments of the method, the subject has been diagnosed as suffering from an inflammatory disease.

In certain embodiments, the compound inhibits interleukin-2 production. In certain of these embodiments, the interleukin-2 production is inhibited by greater than about 20%.

In certain embodiments, the compound binds to CypA with a $K_D$ of less than about 6 µM.

In certain embodiments, the compound reduces T-cell viability in vitro by less than about 10%.

The anti-inflammatory and immunosuppressive properties of representative gracilin A congeners of the invention are further described below.

In another further aspect, the invention provides gracilin A congeners that exhibit a neuroprotective effect. In certain embodiments, the invention provides a method for treating a neurodegenerative disease in a subject, the method comprising administering to a subject in need thereof an effective amount of a compound having the formula:

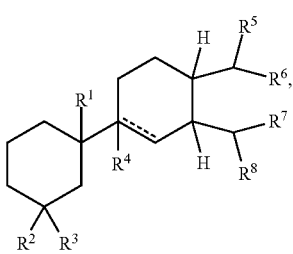

or a stereoisomer or racemate thereof, wherein:
$R^1$, $R^2$, and $R^3$ are independently H or C1-C3 alkyl;
$R^4$ is H, OH, OAc, or absent;
$R^5$ and $R^8$ are independently H or OAc;

$R^6$ and $R^7$ are H or $R^6$ and $R^7$, taken together, are O; and the dashed line denotes a bond when $R^4$ is absent, or absence of a bond when $R^4$ is H, OH, or OAc.

In certain embodiments of the method, the compound is:

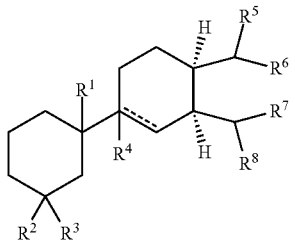

or a stereoisomer or racemate thereof.

Representative compounds useful in the method include:

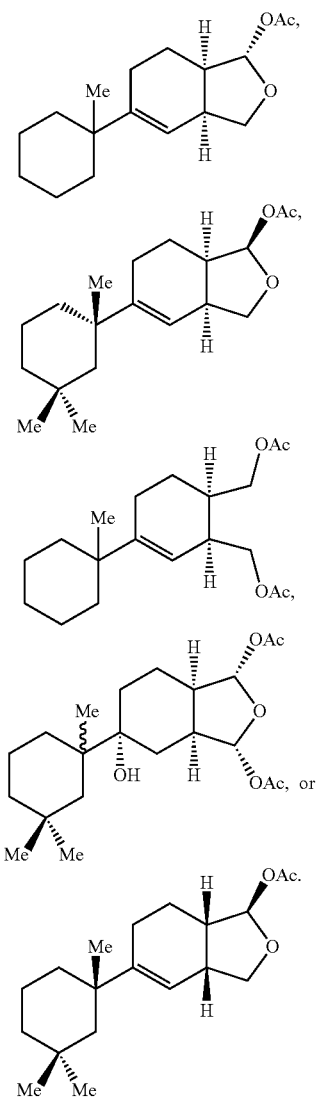

In certain embodiments, the neurodegenerative disease is Alzheimer's disease.

In certain embodiments, the compound inhibits CypD with an $IC_{50}$ of less than about 0.5 μM.

In certain embodiments, the compound inhibits CypA with an $IC_{50}$ of less than about 0.3 μM.

In certain embodiments, the compound inhibits CypD and does not inhibit CypA.

The neuroprotective properties of representative gracilin A congeners of the invention are further described below.

The present disclosure identifies simplified gracilin A congeners that retain potency as immunosuppressive agents through high affinity for CypA with some derivatives displaying significantly higher affinity than gracilin A. In addition, disclosed herein are gracilin A congeners that demonstrate selectivity between CypA and CypD thus leading to potent neuroprotective effects for these congeners devoid of immunosuppressive effects.

The following is a description of the synthetic methodology for preparing the gracilin A congeners of the invention (see FIGS. 1A-1D).

The parent bis-acetoxy furanose 9 was readily obtained through a two-step oxidation/hydrogenation sequence to deliver the syn-substituted acetoxy furanose (±)-9a as a racemate along with the anti-diastereomer (±)-9b.

Derivatives devoid of the cyclohexyl substituent and exocyclic alkene were targeted, namely bicyclic bis-acetoxy furanose 18. This derivative was prepared from a common core 15a that would be employed for all other gracilin A derivatives. A Diels-Alder-Lactonization (DAL) organocascade employing diene 12 and acryloyl chloride 11 with tetramisole as Lewis base catalyst delivered an about 3:1 ratio of diastereomeric cycloadducts endo-15a/exo-15b on gram scale and in 94% ee. The required endo-diastereomer 15a could be isolated in 58% yield and a reduction with $LiAlH_4$ followed by desilylation delivered the ketodiol 16. Swern oxidation led to a dialdehyde which was directly subjected to acid-promoted acetylation and epimerization gave the keto bis-acetoxy furanose 17 as a mixture of syn/anti diastereomers. A subsequent reduction with $NaBH_4$ and dehydration with $SOCl_2$ delivered the inseparable cyclohexenyl-fused, bis-acetoxy furanoses 18 as a mixture of syn/anti diastereomers and regioisomers.

Derivatives devoid of the exocyclic alkene but bearing the cyclohexyl substituent (FIG. 1C) were also targeted. Desilylation of endo-Diels-alder adduct 15a gave bicyclic lactone 19 which was subjected to an allylzinc reagent derived from cyclohexenyl chloride 20a employing the conditions that we previously employed in the synthesis of spongiolactone. This delivered the tricyclic adducts 21a as a 1:1 mixture of diastereomers at the generated quaternary carbon but with high facial selectivity leading to a single epimer at the tertiary alcohol center. Subsequent hydrogenation to reduce the alkene and a similar 3-step process employed previously delivered the hydroxy bis-acetoxy furanose 22 as a 1:1 mixture of diastereomers. Dehydration with Martin's sulfurane gave the alkenes 23 as a mixture of 4 diastereomers due to the alkene regioisomers produced. Purification by HPLC enabled separation of the olefin regioisomers 23a and 23b from 23c and 23d, but not the C10 epimers.

As a preliminary screen for bioactivity of initial gracilin A derivatives, the interaction with CypA of the initially synthesized, highly simplified bis-acetoxy furanose (±)-9 and derivatives 17 and 18 (as a mixture of inseparable olefin regioisomers) devoid of both the cyclohexyl substituent and exocyclic alkene, was analyzed by surface plasmon resonance (SPR) employing cyclosporine A (CsA) and gracilin A as controls.

Figure 2:
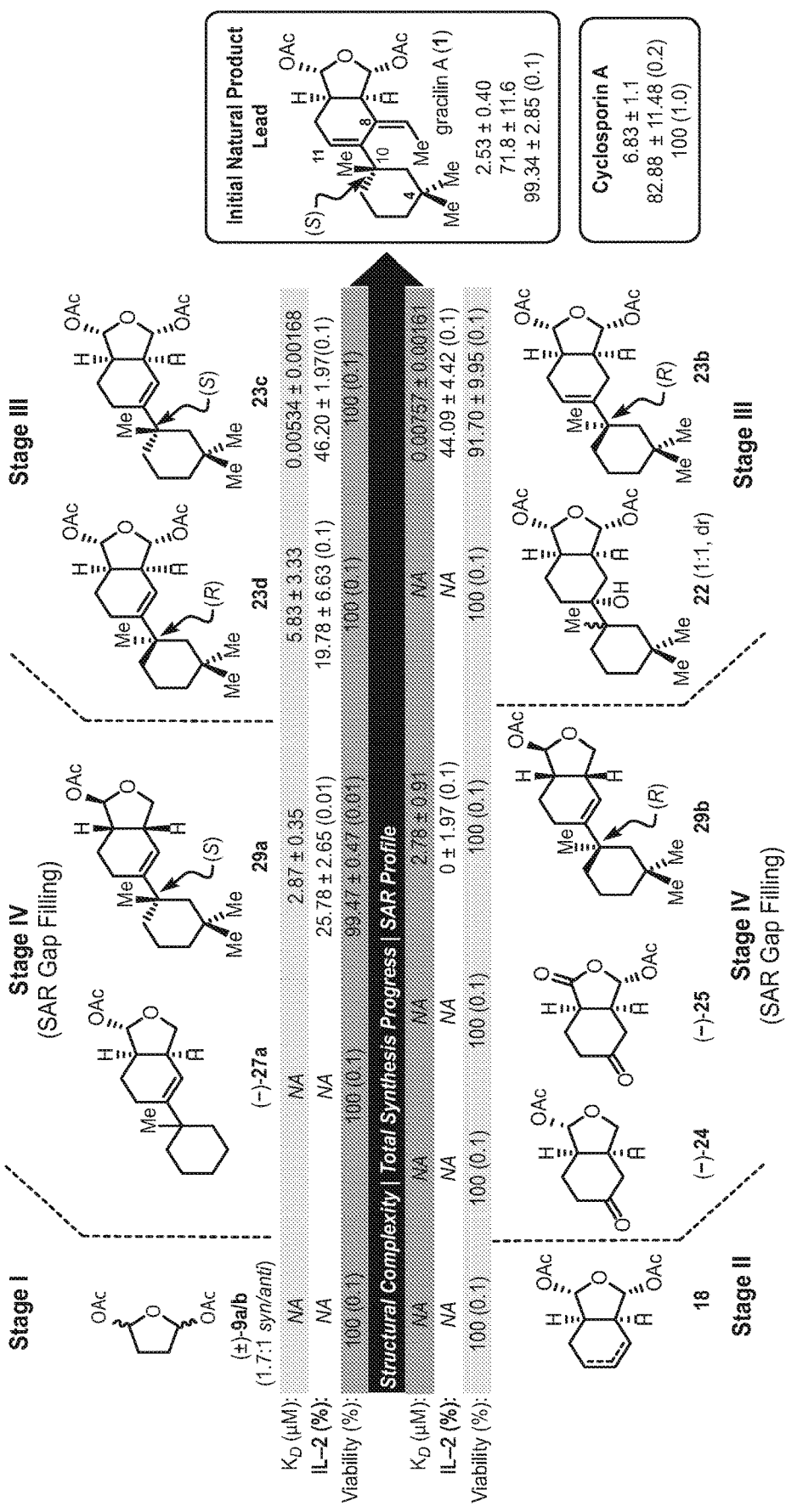
FIG. 2 compares immunosuppressive activity of gracilin A derivatives. Kinetic equilibrium dissociation constants ($K_D$, μM) for binding of gracilin A derivatives to CypA as measured by SPR, interleukin-2 release inhibition (%), and cell viability for human T lymphocytes (% viability, MTT assay). Concentration of each derivative employed in the assays is indicated in parentheses (μM). NA=no activity observed up to 10 μM.

Association curves ($K_D$) were measured at various concentrations compared to gracilin A and the highly simplified derivatives (±)-9, 17, and 18 showed no affinity for CypA (FIG. 2). Upon binding to CypA, CsA and gracilin A modulate interleukin 2 release (IL-2) through the calcineurin pathway, thus the effects of these simplified derivatives on IL-2 production and toxicity to T-cells was measured through determination of % cell viability. As expected, the simplified derivatives (±)-9, 17, and 18 did not inhibit IL-2 production but also did not show signs of cell toxicity at 0.1 µM.

Addition of the trimethyl cyclohexyl moiety to the bicyclic bis-acetoxy furanose core, led to gracilin A derivatives 22-23 with greater bioactivity. The initial diastereomeric mixture of tertiary alcohols 22 derived from cyclohexenyl zinc addition were inactive. However, upon dehydration to introduce the tri-substituted olefins in derivatives 23a-23d, immunosuppressive activity was initially observed with a 2-fold decrease in $K_D$ relative to gracilin A (2.53±0.40 µM) for alkene 23c bearing the 10S configuration (5.83±3.33 µM) with moderate IL-2 inhibition (about 19%). The interplay between the alkene position ($\Delta^{8,9}$ vs. $\Delta^{9,11}$) and the C10 configuration was borne out through derivatives 23a and 23d which exhibited nearly a 1000-fold increase in $K_D$ toward CypA (5.34±1.68 nM and 7.57±1.61 nM, respectively) compared to gracilin A. Inhibition of IL-2 production (about 41-46%) by alkenes 23a, 23d was not at the level of gracilin A (about 71%), however no impact on cell viability was observed for the more potent alkene 23d and ~10% decrease in cell viability was observed for alkene 23a. The absence of the exocyclic methylidene at C8 in derivatives 23a, 23d with concomitant high affinity for CypA suggests that this moiety is not crucial for binding however may impact IL-2 inhibition. See FIG. 2.

These data taken together suggest that the conformational preferences about the C8-C10 bond may play a pivotal role in bioactivity.

Figure 1D:
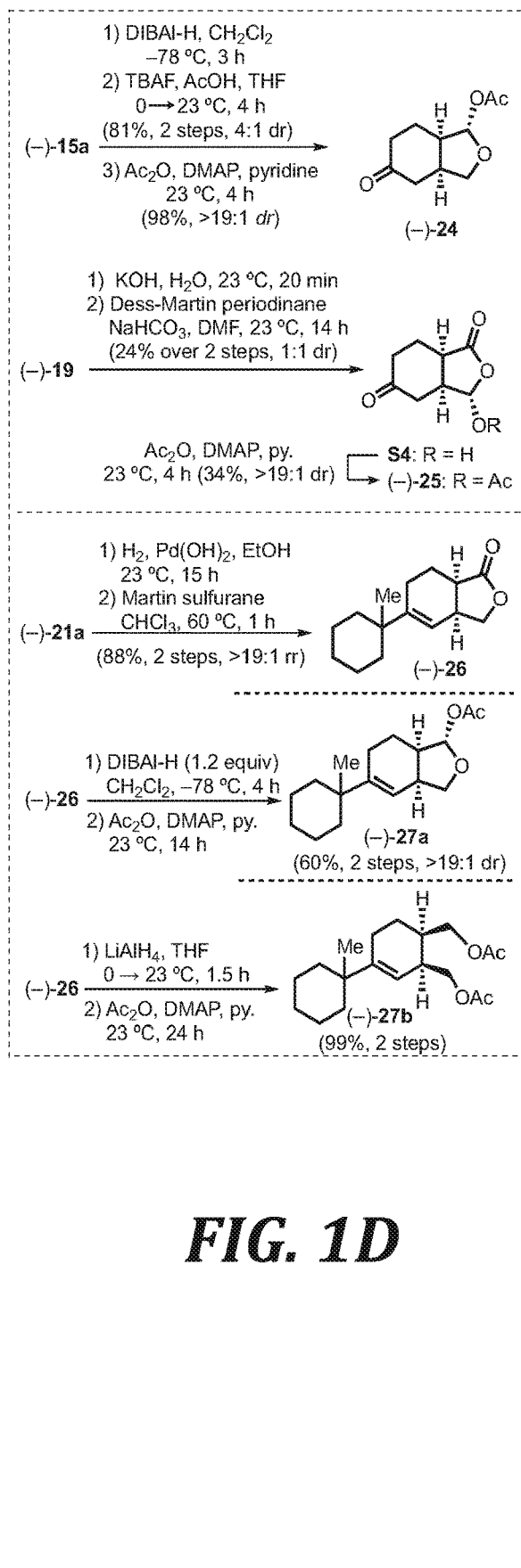

To fill gaps in the structure-activity relationship profile for immunosuppressive activity, changes in the oxidation state of the tetrahydrofuran (i.e., 24, 26) were targeted and the complexity of the cyclohexyl moiety (i.e., 27a,b) using previously accessed intermediates (FIG. 1D). In addition, the enantiomeric series of the bicyclic core (i.e., 29a/29b), available from the diastereomeric lactone exo-15b, was also studied (FIG. 1D). Derivatives with variation in the oxidation state of the tetrahydrofuran were all inactive (24, 26, 27a) supportive of the original hypothesis that the bis-acetoxy furanose is an essential structural feature. α-Epimerization of the diastereomeric Diels-Alder adduct exo-15b enabled study of the enantiomeric series leading to the diastereomeric mono-acetoxy furanoses 29a/29b epimeric at the quaternary C10 center. Affinity to CypA for both diastereomers ($K_D$~3 µM) was comparable to gracilin A, however differential inhibition of IL-2 production (about 26 vs 0%) was observed while both diastereomers remained relatively non-toxic to T-cells. The importance of the quaternary carbon stereochemistry, which directly impacts the conformation about the C9-C10 bond, is highlighted in this series with the natural (S) configuration imparting the greatest bioactivity.

Figure 3:
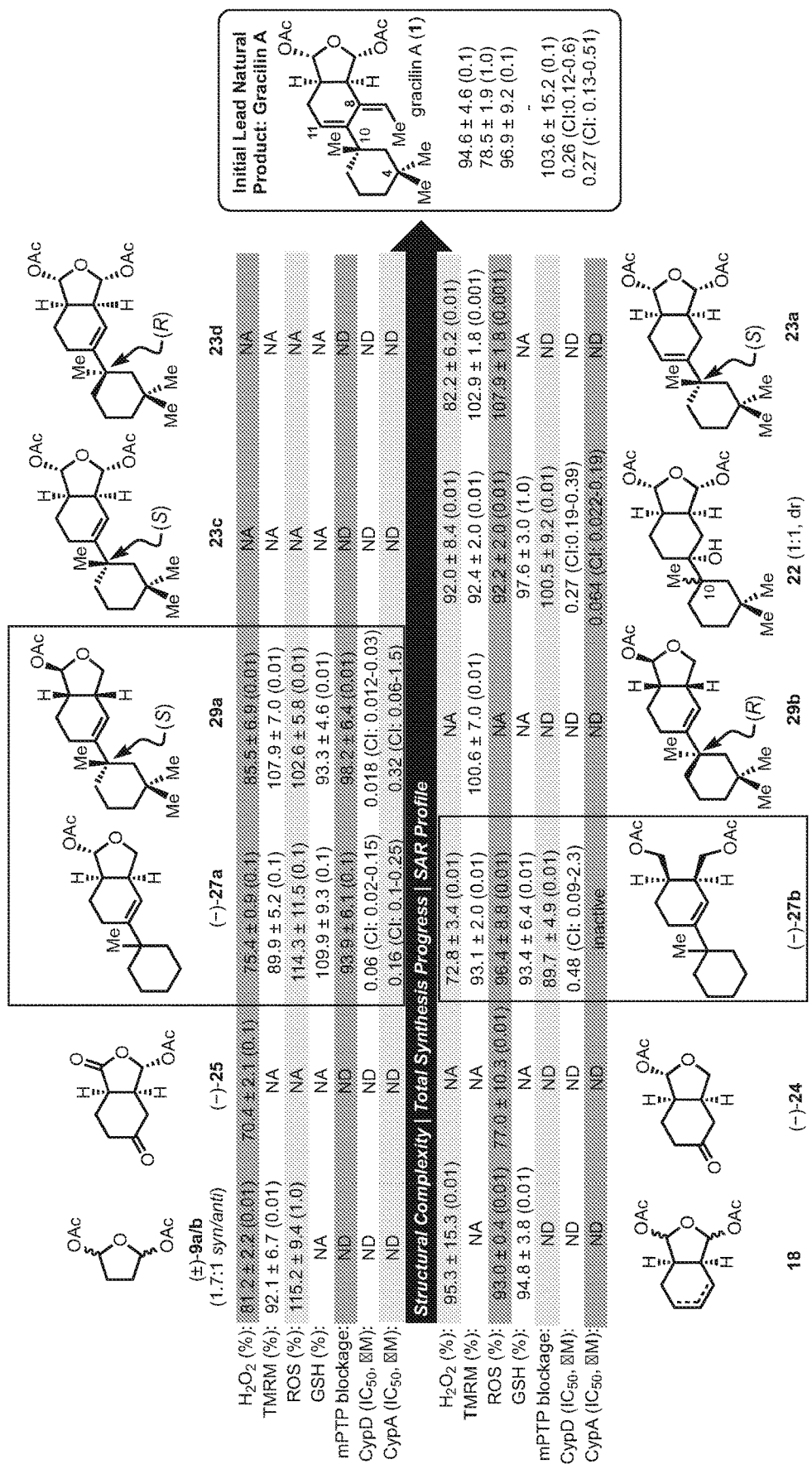
FIG. 3 compares activity of gracilin A derivatives as neuroprotective agents. Cell viability against $H_2O_2$ toxicity, mitochondrial membrane potential restoration (TMRM), % inhibition of reactive oxygen species (ROS) release, % increase cellular glutathione (GSH) levels increase, mPTP blockage, and $IC_{50}$ values for binding to CypD and CypA. Derivative concentration is indicated in parentheses (μM). Values are calculated as percentage of untreated control cells in comparison to $H_2O_2$ treated cells with values: $H_2O_2$ Toxicity 55.6±4.4, TMRM 75.9±3, ROS 140.3±4.4, GSH 82.9±1.6, mPTP blockage: 76.7±2.8. Cyp D and A activity expressed as $IC_{50}$ values (μM). CI (95% confidence interval); $R^2$ values (0.91-0.99) were in acceptable range (see ESI for details); derivatives exhibiting neuroprotective effects while also showing differential activity of CypA vs CypD are highlighted (NA=not active up to 10 μM; ND=not determined).

As described previously, neuroprotective agents can mediate their effects through inhibition of CypD, an isoform of CypA. Given the neuroprotective effects previously observed for gracilin A, the derivatives synthesized through application of BGR were also studied for their neuroprotective effects and their selectivity for CypD versus CypA PPiase activity was determined (FIG. 3). All assays were performed at the indicated concentrations (0.001, 0.01, or 0.1 µM) based on initial cytotoxicity determined with SHSY5Y cells (Table 1). Four parameters were measured to evaluate the neuroprotective effects of the simplified gracilin A derivatives: cell viability, mitochondrial membrane potential (ΔΨm), ROS release, and glutathione (GSH) levels after cellular challenge with $H_2O_2$. Several highly simplified gracilin A derivatives, namely monoacetoxy furanose 27a, the highly simplified diacetate 27b (derived from an intermediate diol in route to 24), the inseparable, diastereomeric alcohols 22, and the monoacetoxy furanose 29a, but not its diastereomer 29b, displayed significant neuroprotective effects based on all five assays. High selectivity for CypD over CypA based on the PPIase activity assay was observed for furanose 27a (about 3-fold) and 29a (about 18-fold) but not alcohols 22 and suggests that their antioxidant effect is mitochondria-related mediated through CypD and thus hold potential as neuroprotective agents devoid of immunosuppressive effects.

Surprisingly, the very simple diacetate 27b displayed the greatest differential CypD ($IC_{50}$=0.48 µM) versus CypA (inactive) affinity while also displaying significant antioxidant activity in all five assays.

Figure 4A:
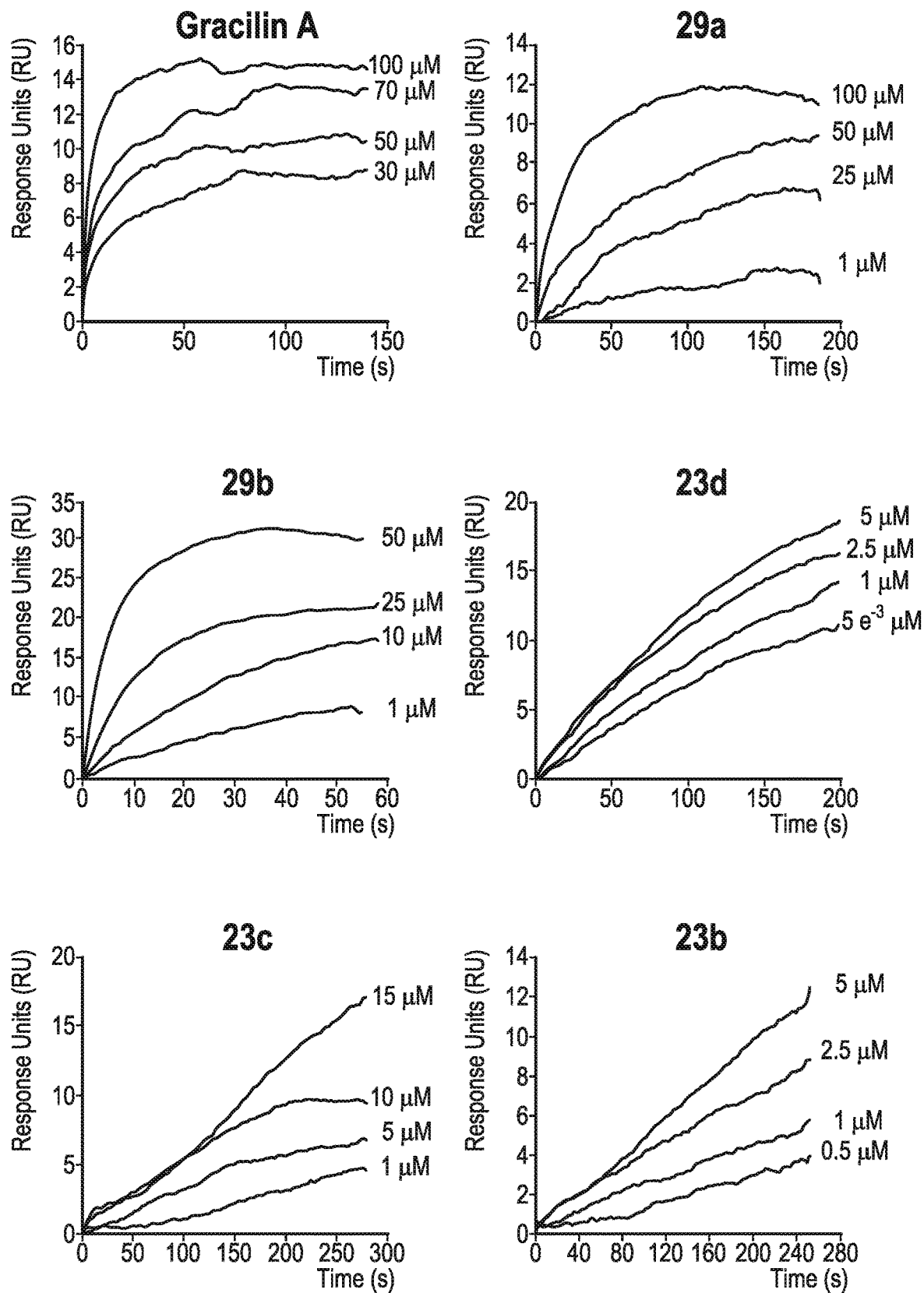
FIGS. 4A-4D illustrate activities of selected gracilin A derivatives in immunosuppressive assays. Binding of gracilin A and selected derivatives to cyclophilin A (CypA) as measured by surface plasmon resonance (SPR) are compared in FIG. 4A. Association curves obtained by addition of compounds over immobilized CypA and subtraction of their respective solvent control. Graphs are from one experiment representative of 4 experiments. Analysis of ligand binding. Kinetic plots of apparent association rate constant $K_{obs}$ ($s^{-1}$) obtained from FIG. 4A are compared in FIG. 4B. Graphs are from one experiment representative of 4 experiments. Effect of gracilin A and selected derivatives on viability of human T lymphocytes are compared in FIG. 4C. Cells were incubated for 48 h with compounds at various concentrations. Data are percentage with respect to control cells, one way ANOVA followed by post hoc Dunnett's test. *p<0.05. Data are mean±SEM of three independent experiments. Effect of gracilin A and selected derivatives on Interleukin-2 (IL-2) production in human T lymphocytes stimulated with Concanavalin A (ConA) are compared in FIG. 4D. Human T lymphocytes were pre-treated for 2 h with compounds and with Con A (50 μg/mL) for 48 h. Values are percentage with respect to control cells, one way ANOVA followed by post hoc Dunnett's test. p<0.01 and *p<0.001. Data are mean±SEM of four independent experiments.
Figure 4B:
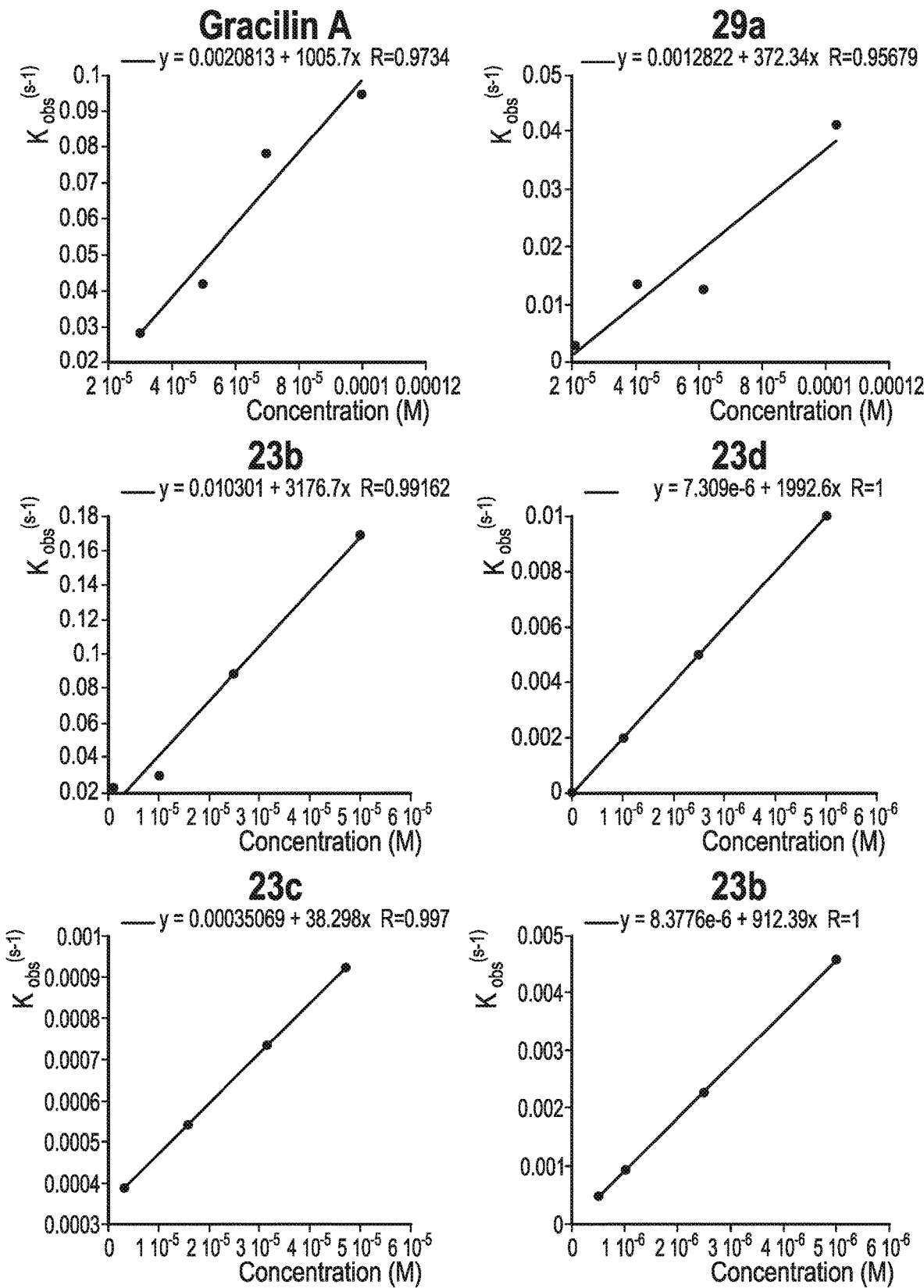

Biological Properties of Representative Gracilin a Derivatives CypA binding was analyzed by surface plasmon resonance (SPR) ((a) Alfonso, A., Pazos, M. J., Femandez-Araujo, A., Tobio, A., Alfonso, C., Vieytes, M. R. and Botana, L. M. Toxins 2014, 6, 96-107; (b) Sanchez, J. A., Alfonso, A., Leiros, M., Alonso, E., Rateb, M. E., Jaspars, M., Houssen, W. E., Ebel, R. and Botana, L. M. Cell Physiol. Biochem., 2015, 37, 779-792). FIG. 4A shows association curves with different concentrations of gracilin A and five synthetic derivatives: 29a, 29b, 23d, 23c and 23b. The $K_D$ association values were found to be similar between CsA, gracilin A and derivatives 29a, 29b, and 23c (~2.8-6.8 µM, FIG. 4B). Compounds 23b and 23d have nanomolar $K_D$ values (7.57±1.61 nM and 5.34±1.68 nM, respectively), hence high CypA affinity.

Figure 4C:
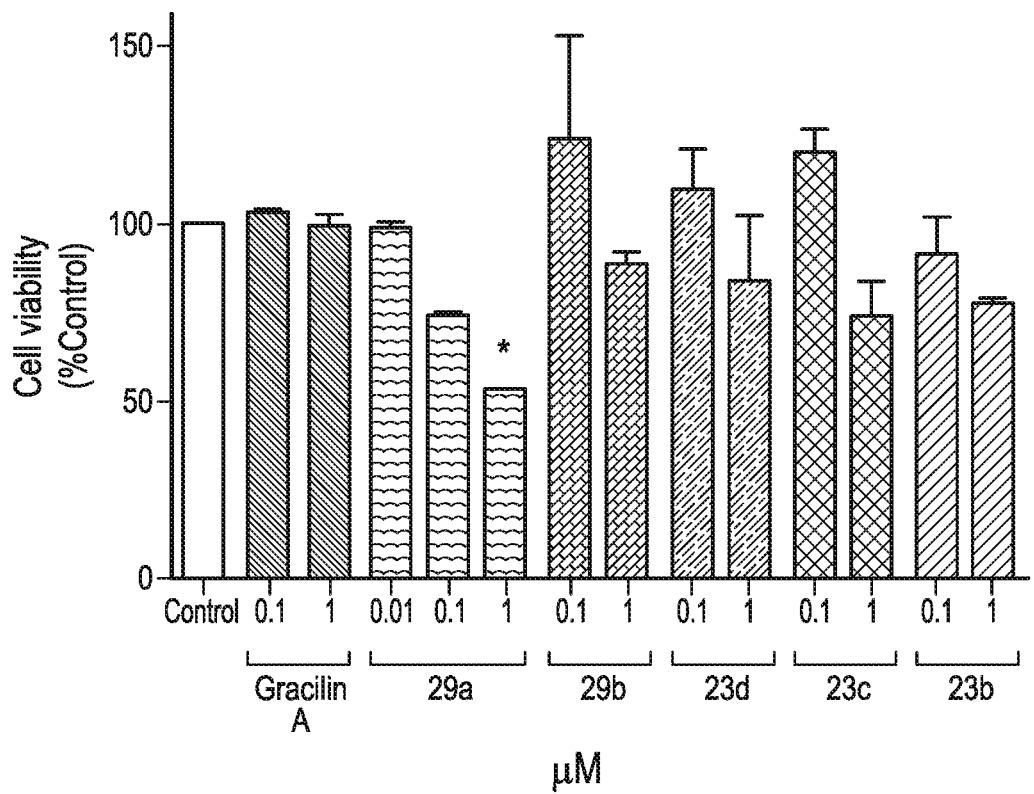
Figure 4D:
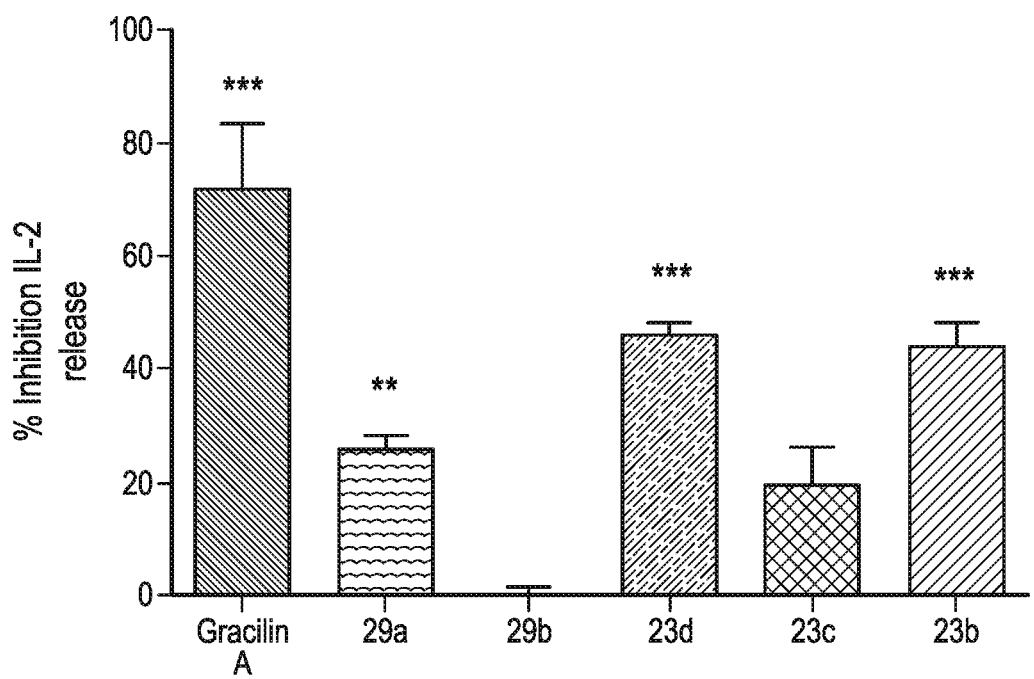

CypA modulates interleukin-2 release (IL-2) through the calcineurin pathway (Zydowsky, L. D., Etzkorn, F. A., Chang, H. Y., Ferguson, S. B., Stolz, L. A., Ho, S. I. and Walsh, C. T. Protein Sci., 1992, 1, 1092-1099). The cytotoxicity (FIG. 4C) and the effect of these five compounds on IL-2 levels. After 48 hours, compounds 29b and 23b-23d showed a 15-25% decrease in cell viability at 1 µM while 29a showed this same decrease at 0.1 µM with no change at lower concentrations. Concanavalin A (Con A) was used to induce IL-2 release in human T lymphocytes (Damsker, J. M., Bukrinsky, M. I. and Constant, S. L. J. Leukoc. Biol., 2007, 82, 613-618) before a 2-hour incubation with non-toxic concentrations of the compounds. CsA was a positive control of IL-2 inhibition. FIG. 4D shows gracilin A and compounds 29a, 23c, 23d, and 23b effect on IL-2 release inhibition. The highest inhibition was obtained by gracilin A (71%), followed by 23b (44%) and 23d (46%), and 29a (26%).

For neuroprotection assays, the compounds cytotoxicity was first assessed toward SH-SY5Y cells (Table 1). Compounds (−)-27a, (−)-27b, 29a, 29b, 22, 23a, 23b, 23c, and 23d led to cell death at the higher concentrations tested after 24 h. Due to the toxicity displayed by compounds 23a and 23d ($IC_{50}$: 1.4 µM), these gracilin derivatives were assayed at lower concentrations (0.001, 0.01 and 0.1 µM) in the neuroprotective tests, whereas the other compounds were tested at 0.01, 0.1 and 1 µM.

Four parameters were monitored to determine the antioxidant potential: cell viability, mitochondrial membrane potential (ΔΨm), ROS release and glutathione (GSH) levels in the presence of the pro-oxidant $H_2O_2$. The known antioxidant vitamin E (VitE) at 25 µM was used as positive control.

Figure 5A:
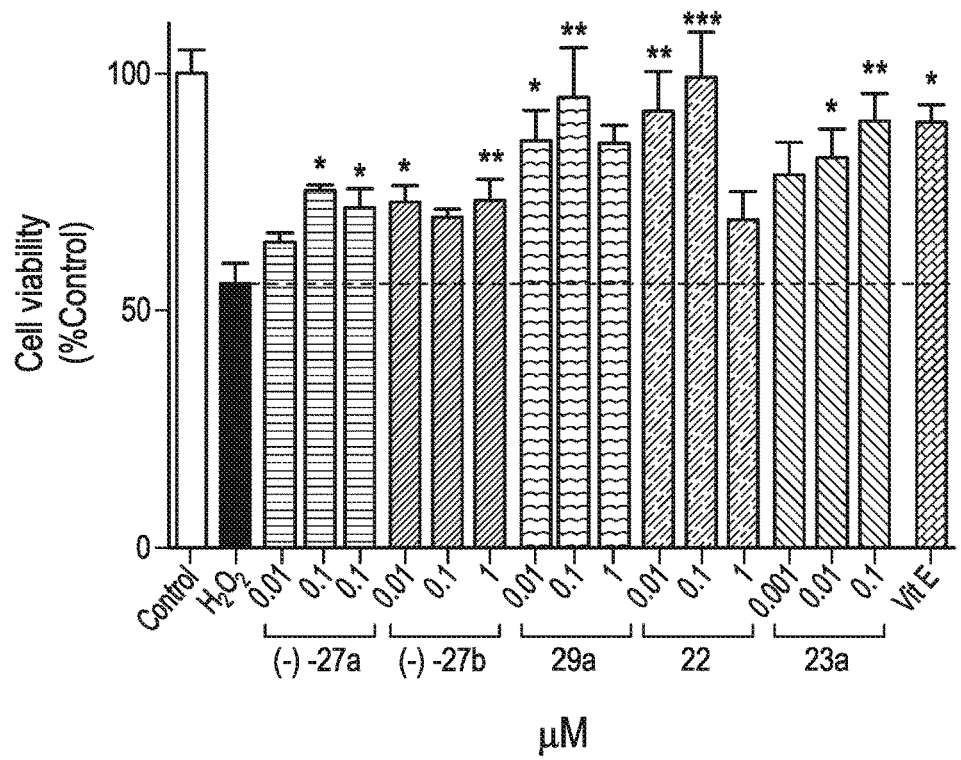
FIGS. 5A-5D illustrate activities of selected gracilin A derivatives in neuroprotective assays. Dotted line indicates levels of cells treated only with 150 μM H$_2$O$_2$. Data are presented as percentage of untreated control cells and compared to cells treated only with 150 μM H$_2$O$_2$ by one way ANOVA and Dunnett's post hoc test. *p<0.05, p<0.01 and *p<0.001. Values are mean±SEM of four independent experiments. Effects of selected gracilin A derivatives on cell viability against H$_2$O$_2$ insult are compared in FIG. 5A. Cell viability was measured by MTT assay. SH-SY5Y cells were treated with 150 μM H$_2$O$_2$ and derivatives for 6 h. Effects of selected gracilin A derivatives on mitochondrial membrane potential (DYm) recovery in FIG. 5B. DYm measured by TMRM assay. Cells were co-treated with 150 μM H$_2$O$_2$ and derivatives for 6 h. Inhibition of reactive oxygen species (ROS) release by selected gracilin A derivatives in FIG. 5C. ROS levels were assessed with 5-(and-6)-carboxy-2',7'-dichlorodihydrofluoresceindiacetate. SH-SY5Y cells were co-incubated with derivatives and 150 μM H$_2$O$_2$ for 6 h. Evaluation of glutathione (GSH) levels in cells treated with selected gracilin A derivatives in FIG. 5D. GSH levels were measured by Thiol Tracker Violet in neuroblastoma cells co-treated with 150 μM H$_2$O$_2$ and derivatives for 6 h.

Neuroprotection against $H_2O_2$ toxicity was evaluated by co-treating cells with 150 µM $H_2O_2$ and the compounds for 6 h. $H_2O_2$ decreased viability by 44.4±4.4% (p=0.00005). Eight gracilin A derivatives were protective at one or more concentrations. (−)-27a, (−)-27b, 29a, 22 and 23a protected cells against $H_2O_2$ insult at almost all concentrations (0.01, 0.1 and 1 µM; FIG. 5A).

Figure 5B:
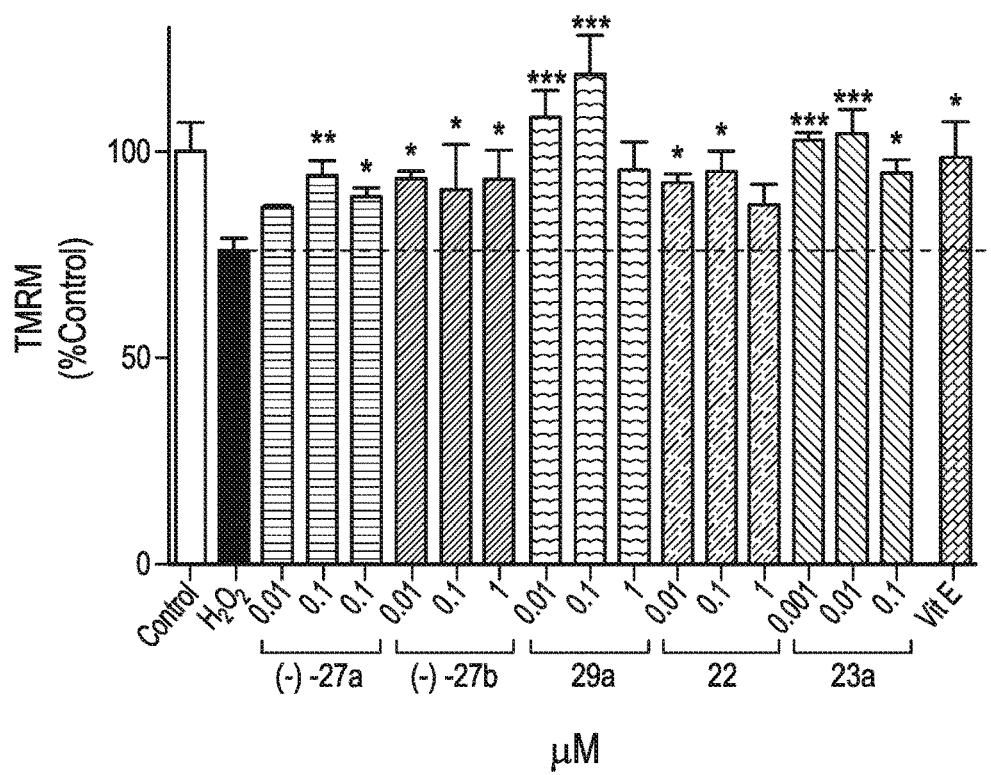

Tetramethylrodamine methyl ester (TMRM) was used to evaluate the ΔΨm. After $H_2O_2$ treatment, cells exhibit a TMRM signal decrease of 24.1±3% (p=0.0032). 29a, 23a, (−)-27a, (−)-27b and 22 recovered ΔΨm compared to $H_2O_2$ control (FIG. 5B).

Figure 5C:
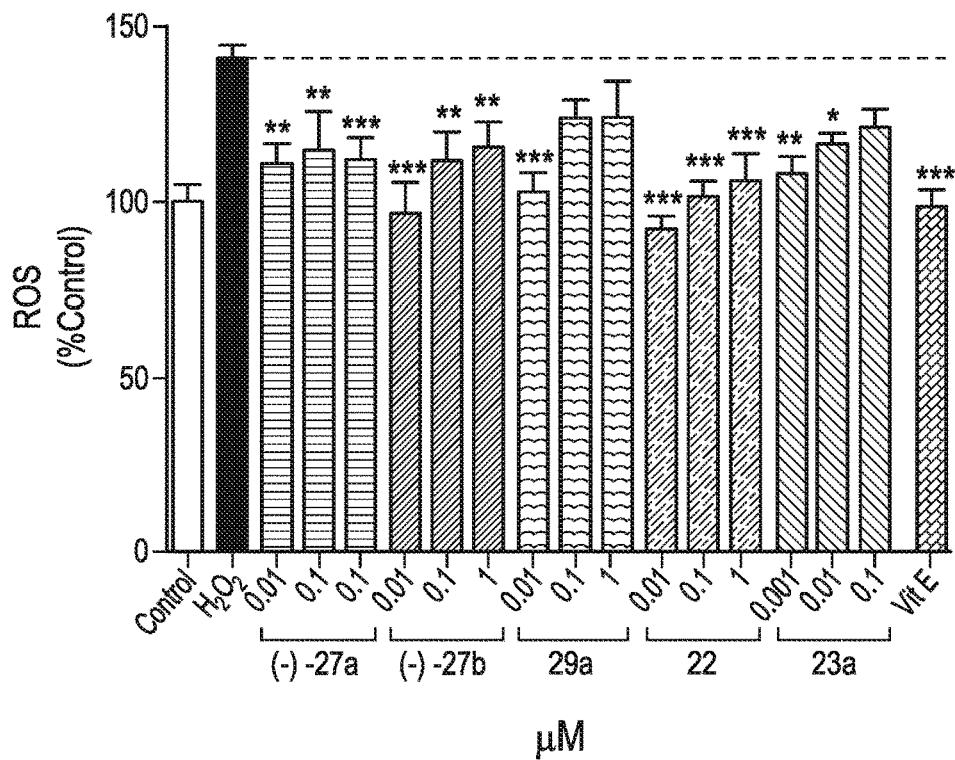

To assess if compounds were acting as ROS scavengers, carboxy-H2DCFDA was used to determine ROS levels. $H_2O_2$-treated cells increased ROS levels by 141.4±4.6% (p=0.00002) versus untreated cells. A decrease was observed after cotreatment with eight compounds, achieving untreated cell levels. Among them, five derivatives showed better results: (−)-27a, (−)-27b, 22, 23a and 23b diminishing ROS at two or three concentrations (FIG. 5C).

Figure 5D:
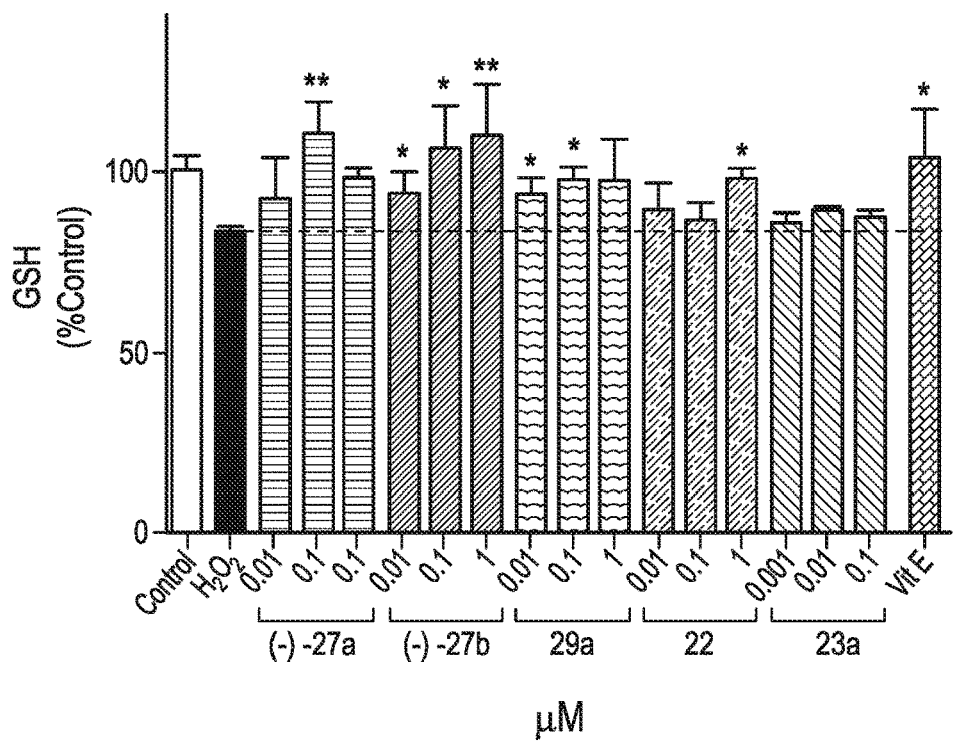

For GSH, the main non-enzymatic antioxidant in cells, neuroblastoma cotreated with $H_2O_2$ and (−)-27a, 22, (−)-27b and 29a recovered GSH levels (FIG. 5D) at two or more concentrations versus $H_2O_2$ control (82.9±1.6%, p=0.027). Since gracilin A's anti-OS effect is related with mPTP opening, the effective concentration of each compound was selected to determine their effect on mPTP.

Figure 6A:
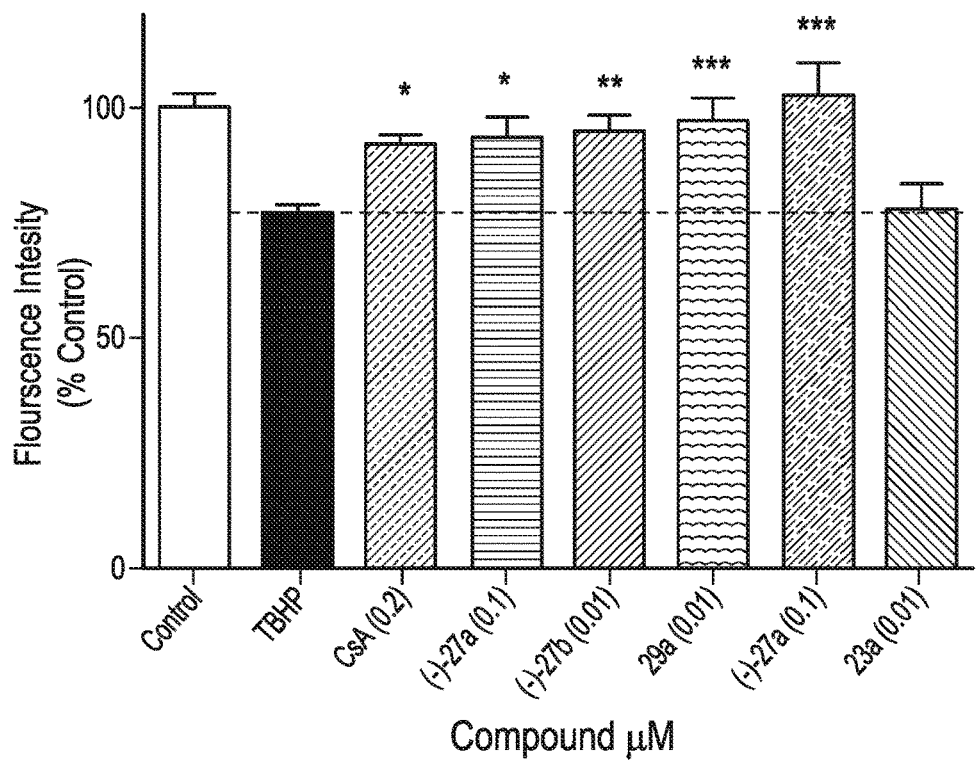
FIGS. 6A-6F illustrate activities of selected gracilin A derivatives on the mitochondrial membrane permeability transition pore (mPTP). SH-SY5Y cells were treated with both 1 mM TBHP and gracilin derivatives and the extent of mPTP opening was evaluated by flow cytometry are compared in FIG. 6A. Values are presented as percentage of untreated control cells and compared to cells treated only with 1 mM TBHP by one way ANOVA test, followed by Dunnett's post hoc test. p<0.01, *p<0.001. Dotted line indicates the level of cells treated with 1 mM TBHP alone. Values are mean±SEM of four independent experiments. Inhibition of CypD and CypA PPIase activity by gracilin A derivatives are compared in FIGS. 6B-6E. Solid line represents inhibition of CypD PPIase activity while dotted lines show inhibition of CypA PPIase activity. CsA was used as a positive control (see FIG. 6F). Data are presented as percentage of the maximal PPIase activity. Values are the mean±SEM of four independent experiments.
Figure 6B:
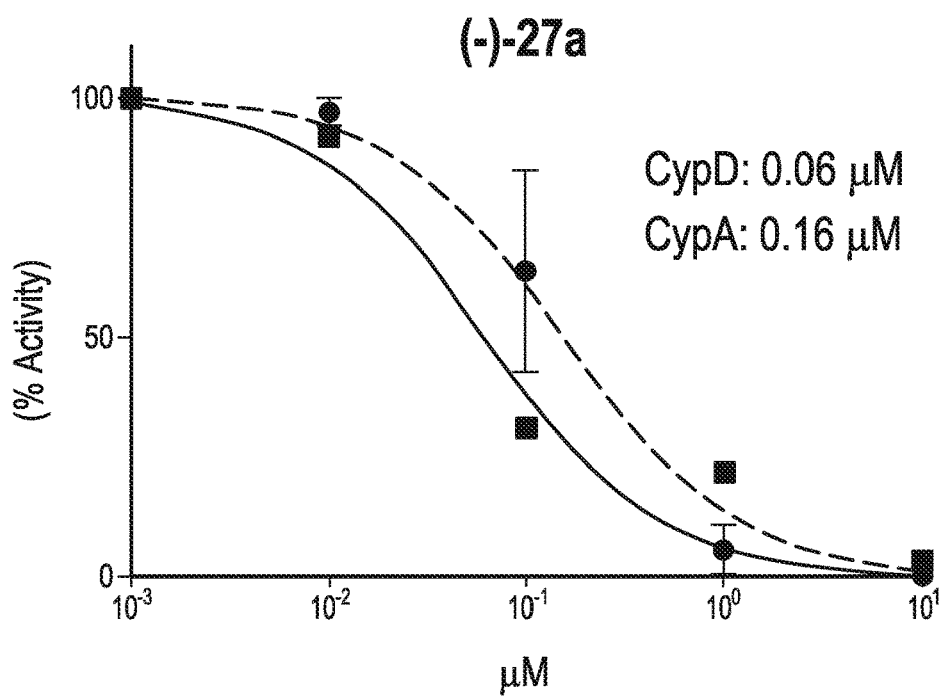
Figure 6C:
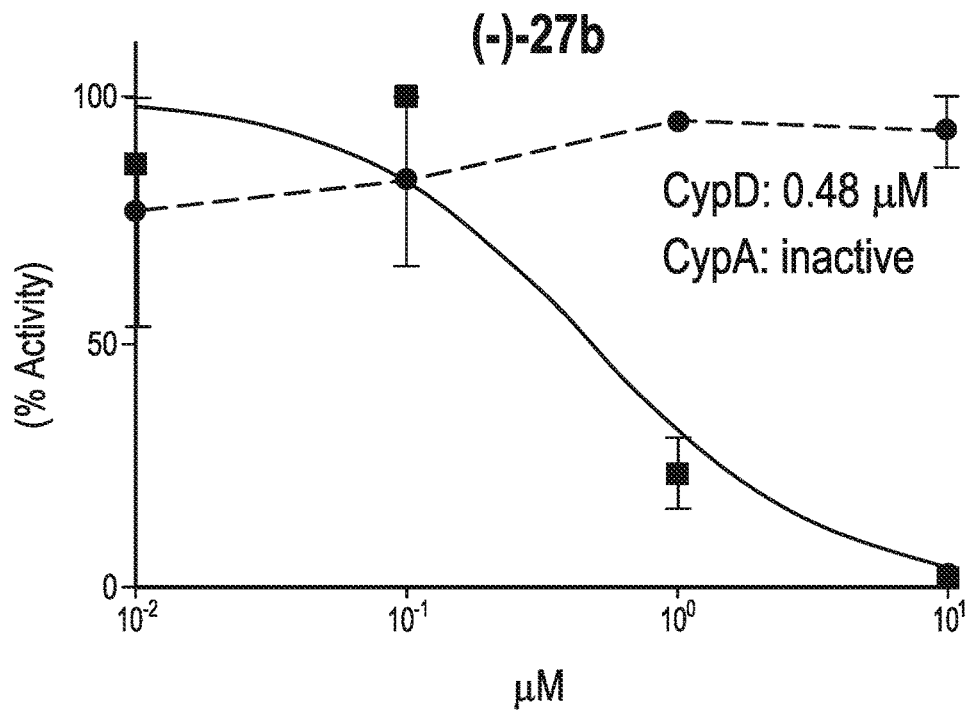
Figure 6D:
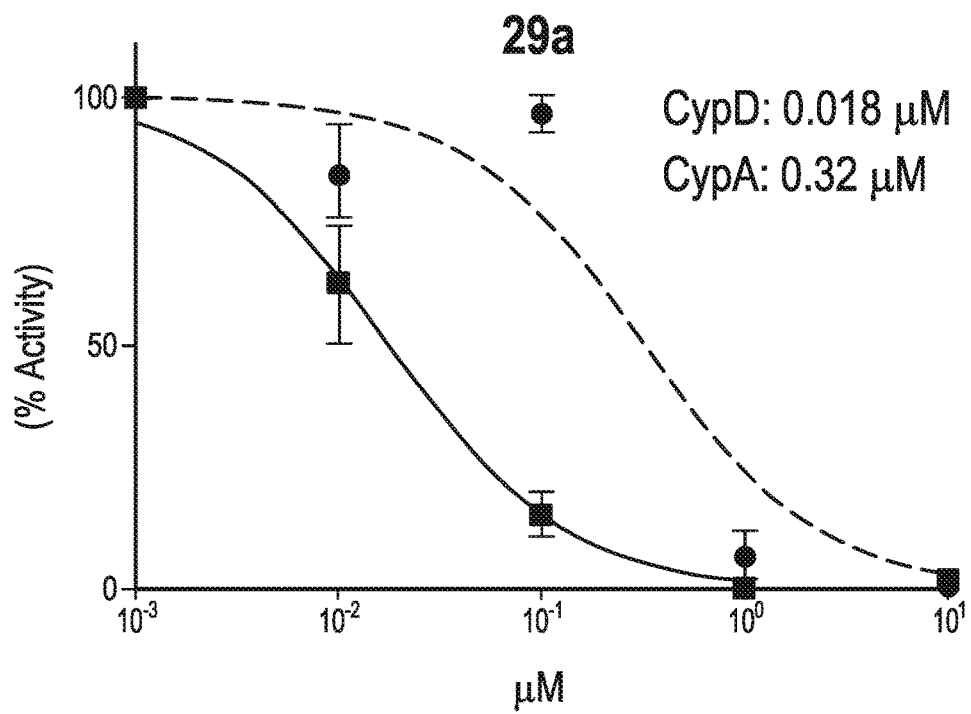
Figure 6E:
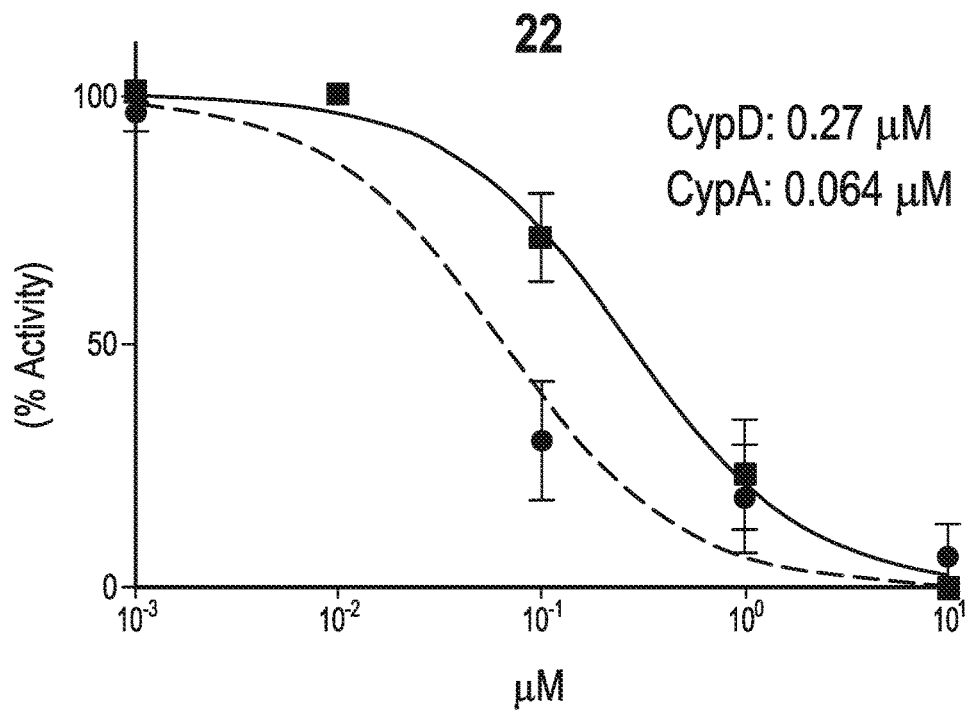
Figure 6F:
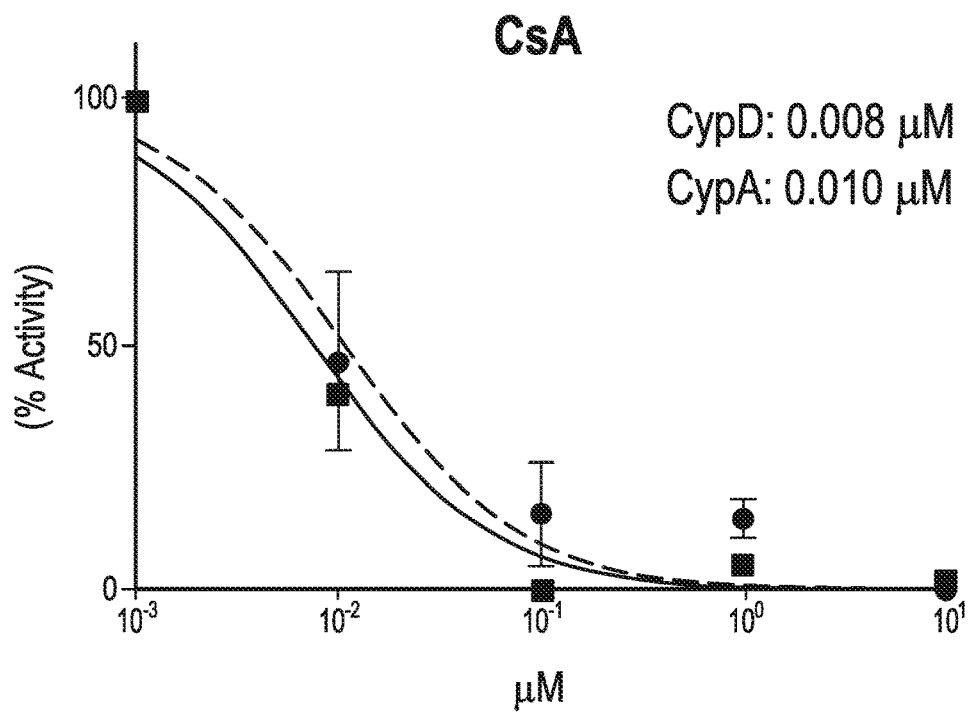
Figure 7A:
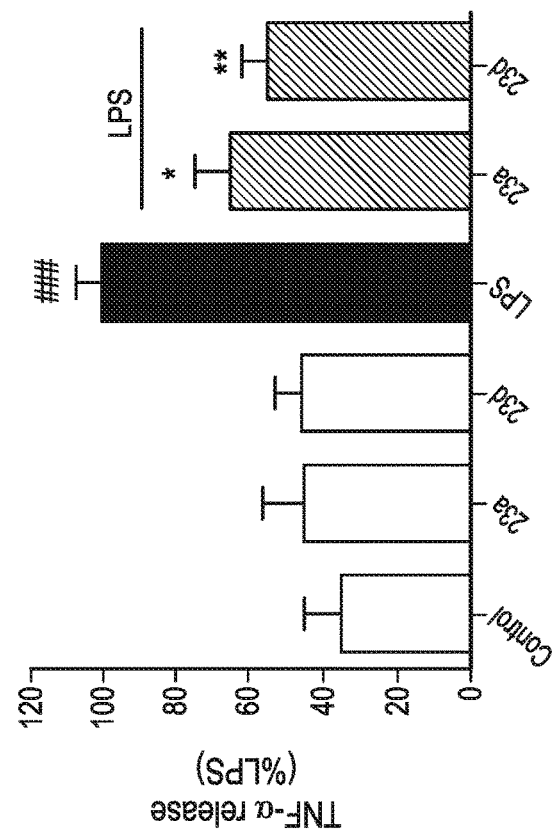
FIGS. 7A-7D compare anti-inflammatory and immunosuppressive effects of representative gracilin A derivatives of the invention. The effects of 23a and 23d on IL-6 (right figure) and TNF-α (left figure) release in BV2 cells are compared in FIG. 7A. The effect of 23a and 23d on the expression of NF-κB p65 (right figure) and Nrf2 (left figure) in BV2 cells are compared in FIG. 7B. The effect of 23a and 23d on the expression of CypA in BV2 cells are compared in FIG. 7C. The effect of 23a and 23d on CypA (right figure), CypB (middle figure) and CypC release (left figure) in activated human T lymphocytes are compared in FIG. 7D.
Figure 7A:
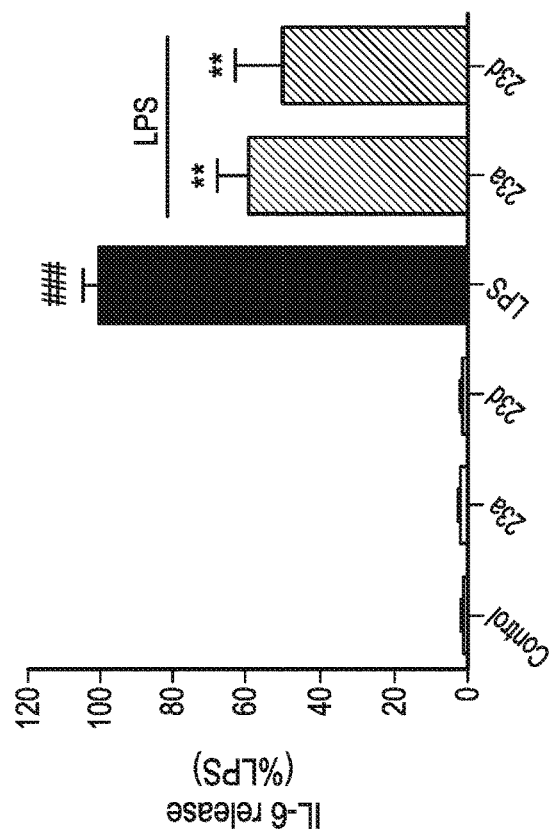
Figure 7B:
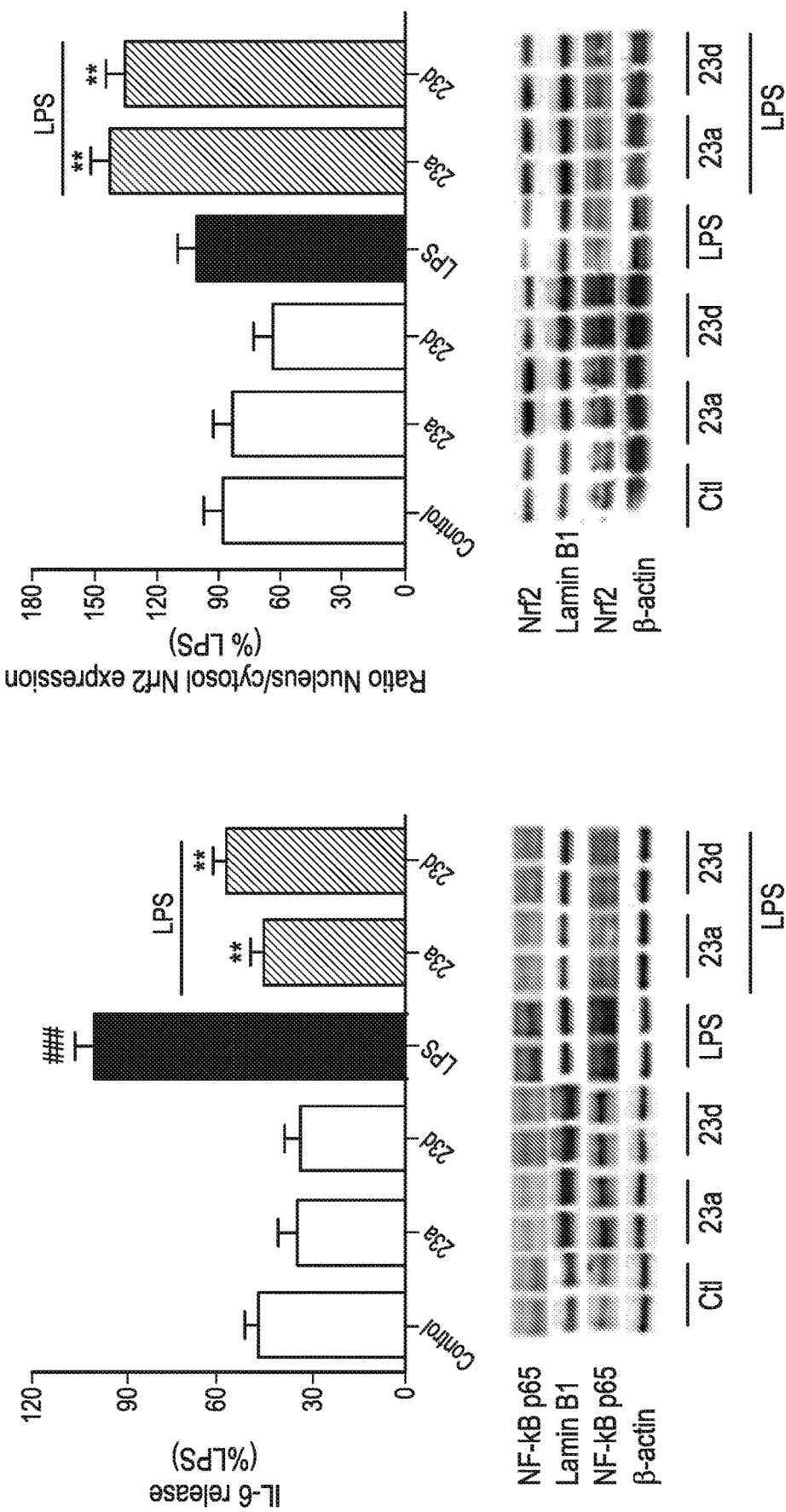
Figure 7C:
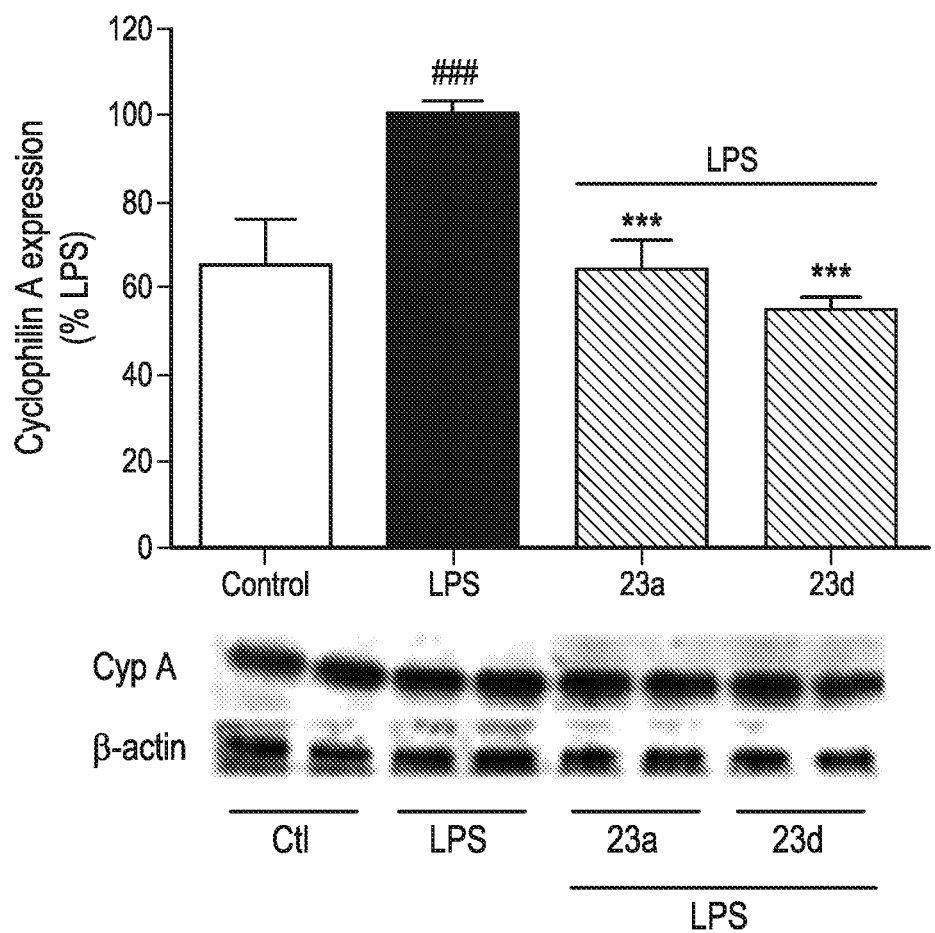
Figure 7D:
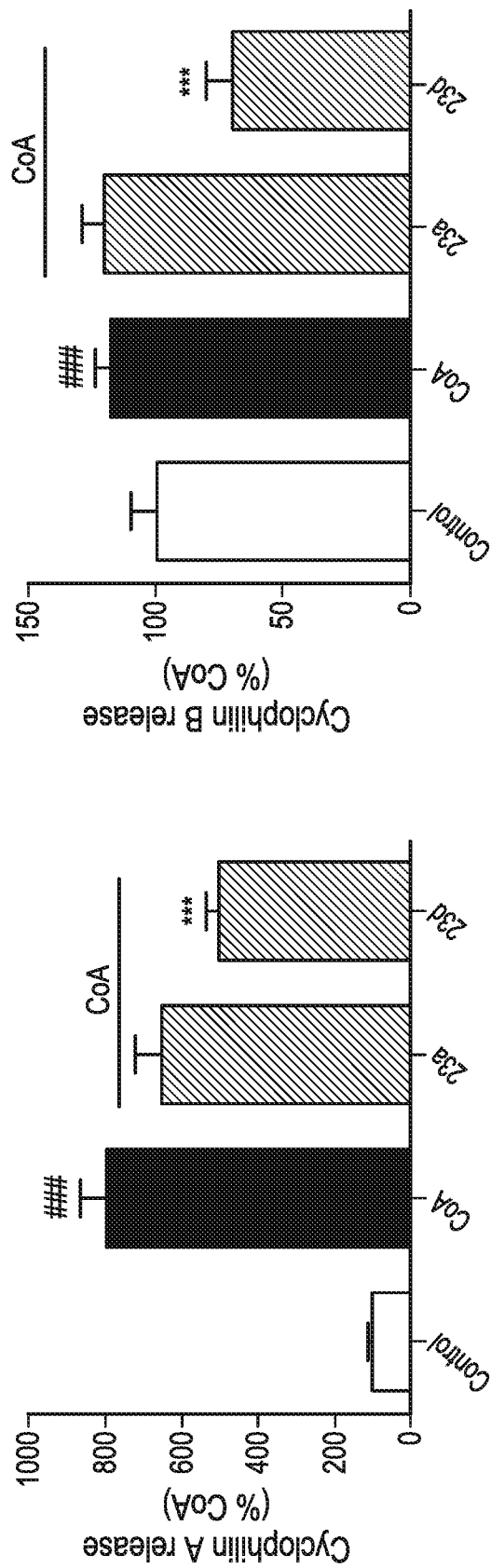
Figure 7D:
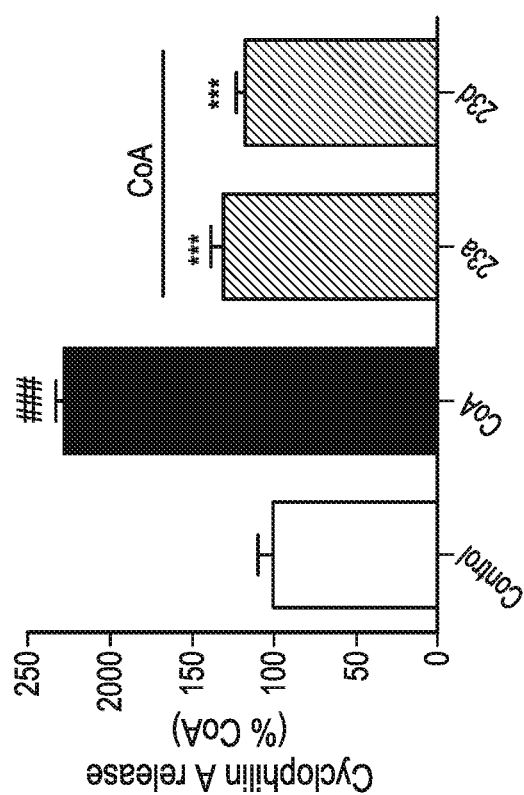

Derivatives 29a, (−)-27a, (−)-27b and 22 prevent TBHP-induced opening (77.13}2.3%, p=0.00002) (FIG. 6A). CsA (0.2 µM) was used as a positive control.

As CypD involvement in mPTP functioning is related with its PPIase activity (Connern, C. P. and Halestrap, A. P. *Biochem. J.*, 1994, 302, 321-324), the modulation of this activity was studied. Compounds 29a, (−)-27a, (−)-27b and 22 inhibited CypD activity at low micromolar concentrations ($IC_{50}$<0.5 µM) (FIG. 6B-6F). To analyze the specificity of these compounds for CypD, the PPIase inhibitory activity of these derivatives toward CypA was studied. Compound (−)-27b was inactive toward CypA (up to 10 µM) showing complete selectivity for CypD with an $IC_{50}$=0.48 (CI: 0.09-2.3) µM. Derivatives (−)-27a and 29a showed higher $IC_{50}$ values for CypA than for CypD indicating some selectivity for CypD, ~3-fold and 18-fold respectively. On the other hand, compound 22 showed greater activity toward CypA vs CypD ($IC_{50}$=0.064 (CI: 0.022-0.19) vs 0.48 (CI: 0.09-2.3) M; 4-fold selectivity for CypA).

TABLE 1

Cellular toxicity elicited by the *spongionella* derivatives in SH-SY5Y cells.

| Compound | IC50 (µM) | 95% Confidence Interval | R2 |
| --- | --- | --- | --- |
| 29a | 16.5 7.1 | 1.9-26.1 | 0.98 |
| 29b | 7.9 | 0.85-74.3 | 0.98 |
| 22 | 6.5 | 0.15-28 | 0.99 |
| 23a | 1.4 | 0.19-10.3 | 0.96 |
| 23b | 4.2 | 0.27-63.9 | 0.96 |
| 23c | 4.2 | 0.66-26.3 | 0.96 |
| 23d | 1.4 | 0.64-3.2 | 0.96 |

$IC_{50}$ obtained after 24 h incubation and calculated with a log(inhibitor) vs. response fitting model of GraphPad Prism 5.0 software. Data of three independent experiments.

Anti-Inflammatory and Immunosuppressive Effects of Representative Gracilin Derivatives Anti-inflammatory and immunosuppressive effects of selected gracilin A derivatives ((+)-23a and (−)-23d) are shown in FIGS. 7A-7D. The effects of 23a and 23d on IL-6 (right figure) and TNF-α (left figure) release in BV2 cells are compared in FIG. 7A. Cells were pre-treated with compounds (1 µM) for one hour and then stimulated with lipopolysaccharide (LPS) 500 ng/mL. IL-6 and TNF-α levels were measured by ELISA. Data are represented as a percentage, being the result of mean±SEM of a minimum of N=3 independent experiments performed by duplicate. The values are shown as the difference between cells treated with LPS alone versus cells treated with compounds in presence of LPS by ANOVA statistical analysis followed by post hoc Dunnet's t-test. *p<0.05 and p<0.01, or cells treated with LPS versus control cells. ###p<0.001. The effect of 23a and 23d on the expression of NF-κB p65 (right figure) and Nrf2 (left figure) in BV2 cells are compared in FIG. 7B. Cells were pre-treated with compounds (1 µM) for one hour and then stimulated with lipopolysaccharide (LPS) 500 ng/mL. The NF-κB p65 subunit and Nrf2 expression was measured in cytosolic and nucleus lysates as well by western blot and represented as nucleus/cytosol ratio. Cytosolic protein levels were normalized with p-actin and nuclear protein levels were normalized with lamin B1. Data are represented as a percentage, being the result of mean absorbance±SEM of a minimum of N=3 independent experiments performed by triplicate. The values are shown as the difference between cells treated with LPS alone versus cells treated with compounds in presence of LPS by ANOVA statistical analysis followed by post hoc Dunnet's t-test. p<0.01, or cells treated with LPS versus control cells. ###p<0.001. The effect of 23a and 23d on the expression of CypA in BV2 cells are compared in FIG. 7C. Cells were pre-treated with compounds (1 µM) for one hour and then stimulated with lipopolysaccharide (LPS) 500 ng/mL. The CypA expression was measured in cytosolic lysates as well by western blot. Protein levels were normalized with p-actin. Data are represented as a percentage, being the result of mean absorbance±SEM of a minimum of N=3 independent experiments performed by triplicate. The values are shown as the difference between cells treated with LPS alone versus cells treated with compounds in presence of LPS by ANOVA statistical analysis followed by post hoc Dunnet's t-test. *p<0.001, or cells treated with LPS versus control cells. ###p<0.001. The effect of 23a and 23d on CypA (right figure), CypB (middle figure) and CypC release (left figure) in activated human T lymphocytes are compared in FIG. 7D. Cells were pre-treated with compounds (0.1 µM) for two hours and then stimulated with concanavalin A (CoA) 50 ng/mL. Cyclophilin levels were measured by ELISA. Data are represented as a percentage, being the result of mean±SEM of a minimum of N=3 independent experiments performed by duplicate. The values are shown as the difference between cells treated with CoA alone versus cells treated with compounds in presence of LPS by ANOVA statistical analysis followed by post hoc Dunnet's t-test. *p<0.001, or cells treated with Concanavalin A versus control cells. ###p<0.001.

Neuroprotective Effects of Representative Gracilin Derivatives

Neuroprotective effects of selected gracilin A derivatives (21a, 27a, 27b, 29a, 21b, 22 and 23c) are compared in FIGS. 8A-8D. Relative expression of the antioxidant enzymes glutathione peroxidase (left panel) and superoxide dismutase 1 (right panel) in SH-SY5Y neuroblastoma cells treated with gracilin A derivatives and H₂O₂ are compared in FIG. 8A. Cells treated with $H_2O_2$ alone were used as calibrator and are represented by x-axes. Data are expressed as mean±SEM of three independent replicates performed by triplicate and compared to $H_2O_2$ control cells by one way ANOVA and Dunnett's tests. $*p<0.05$. $p<0.01$, $*p<0.001$. The effect of gracilin A derivatives on β-secretase (BACE1) activity is compared in FIG. 8B. The ability of compounds to inhibit the enzyme was determined with a fluorescence resonance energy transfer (FRET) assay kit. A statine-derived inhibitor (Inh) was used to check the validity of the assay.

Figure 8A:
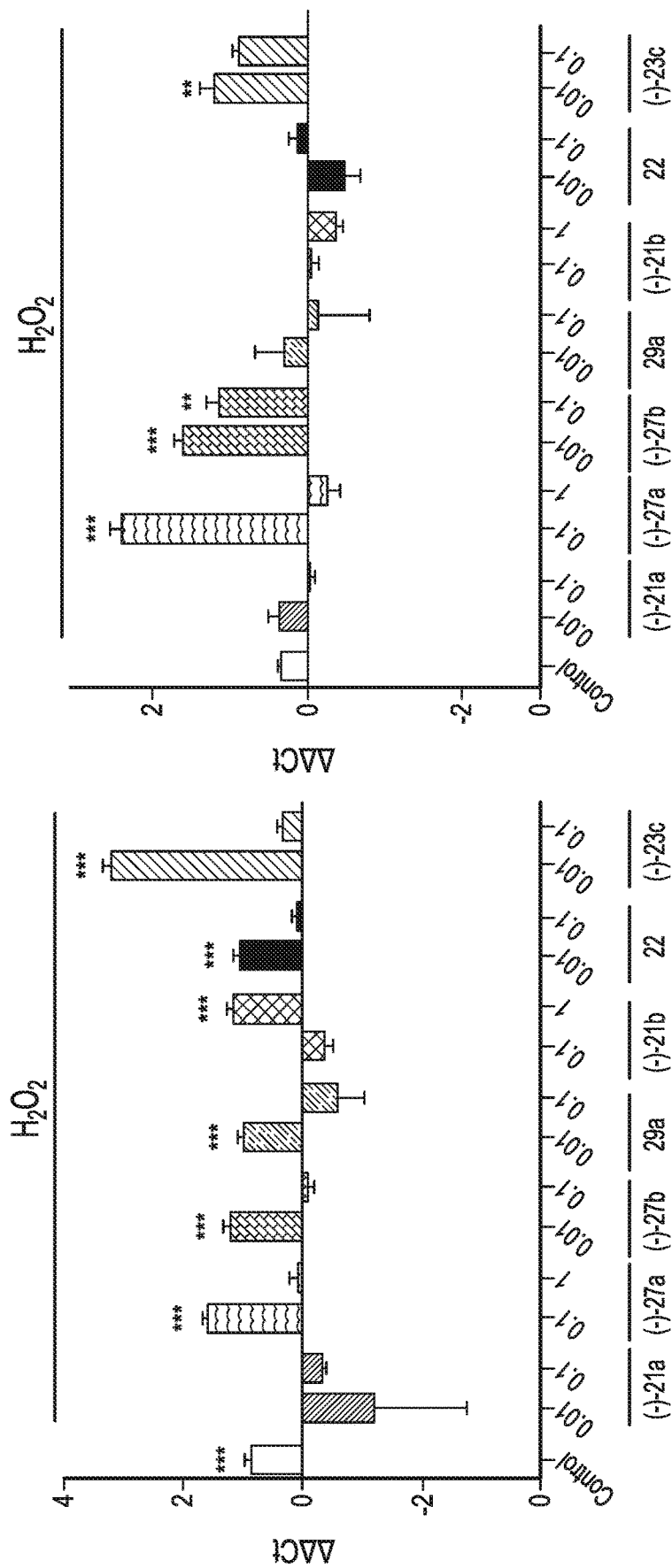
FIGS. 8A-8D compare neuroprotective effects of representative gracilin A derivatives of the invention. Relative expression of the antioxidant enzymes glutathione peroxidase (left panel) and superoxide dismutase 1 (right panel) in SH-SY5Y neuroblastoma cells treated with gracilin A derivatives and H$_2$O$_2$ are compared in FIG. 8A. The effect of gracilin A derivatives on β-secretase (BACE1) activity is compared in FIG. 8B. Nuclear expression of the transcription factors Nrf2 and NFκB-p65 in BV2 microglial cells are compared in FIG. 8C. The cell viability of neuroblastoma was determined as shown in FIG. 8D.
Figure 8B:
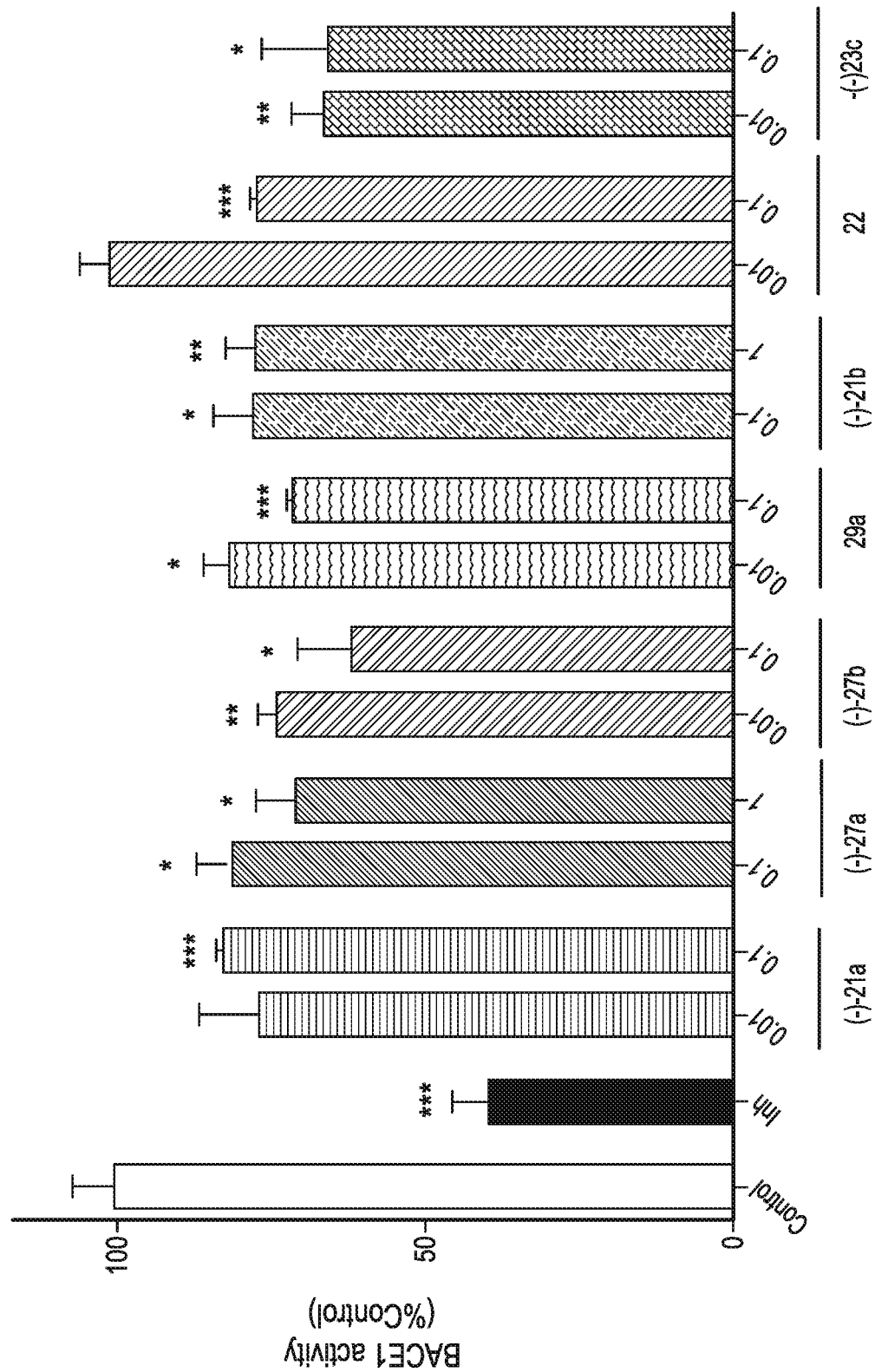
Figure 8C:
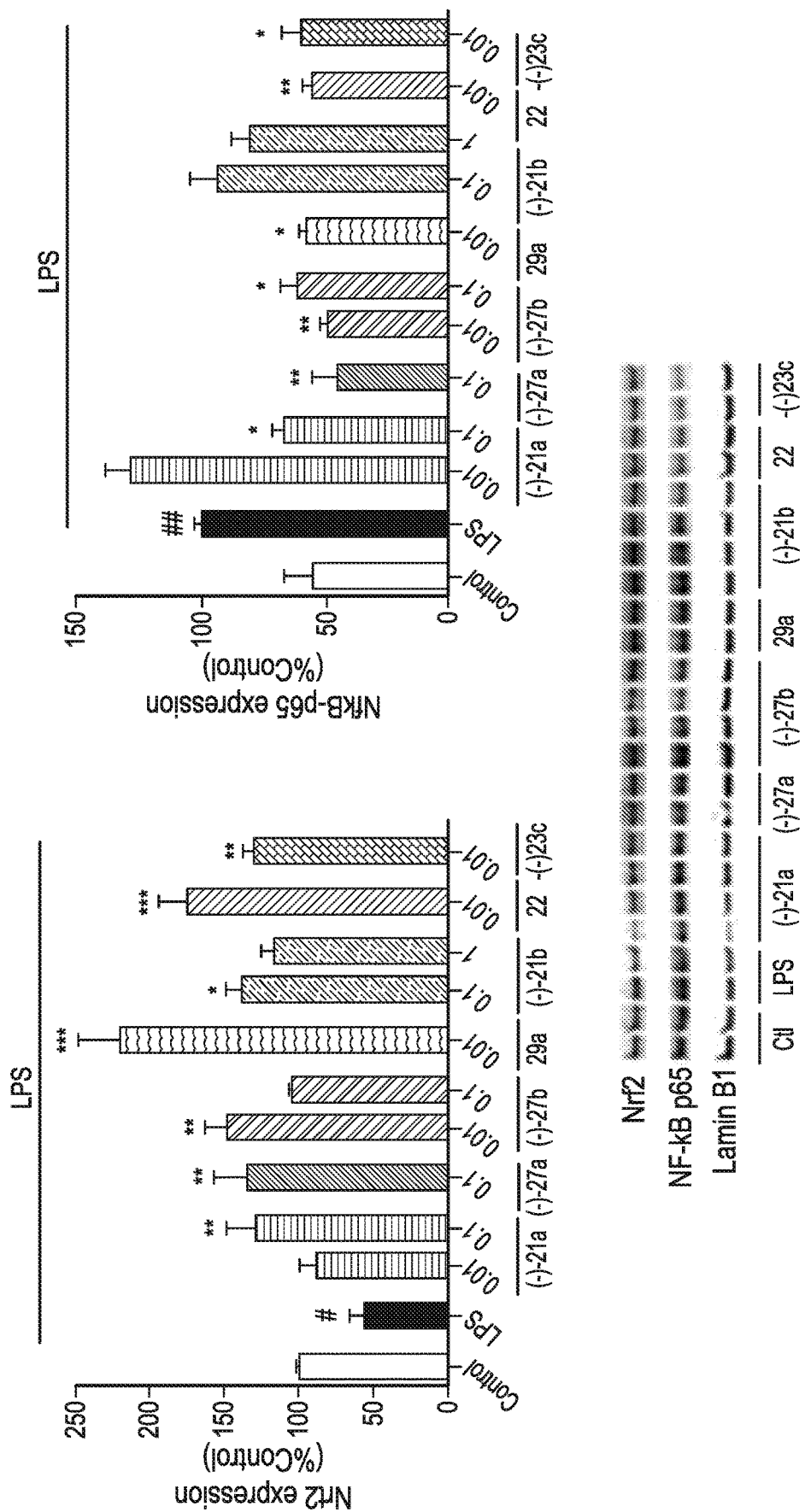
Figure 8D:
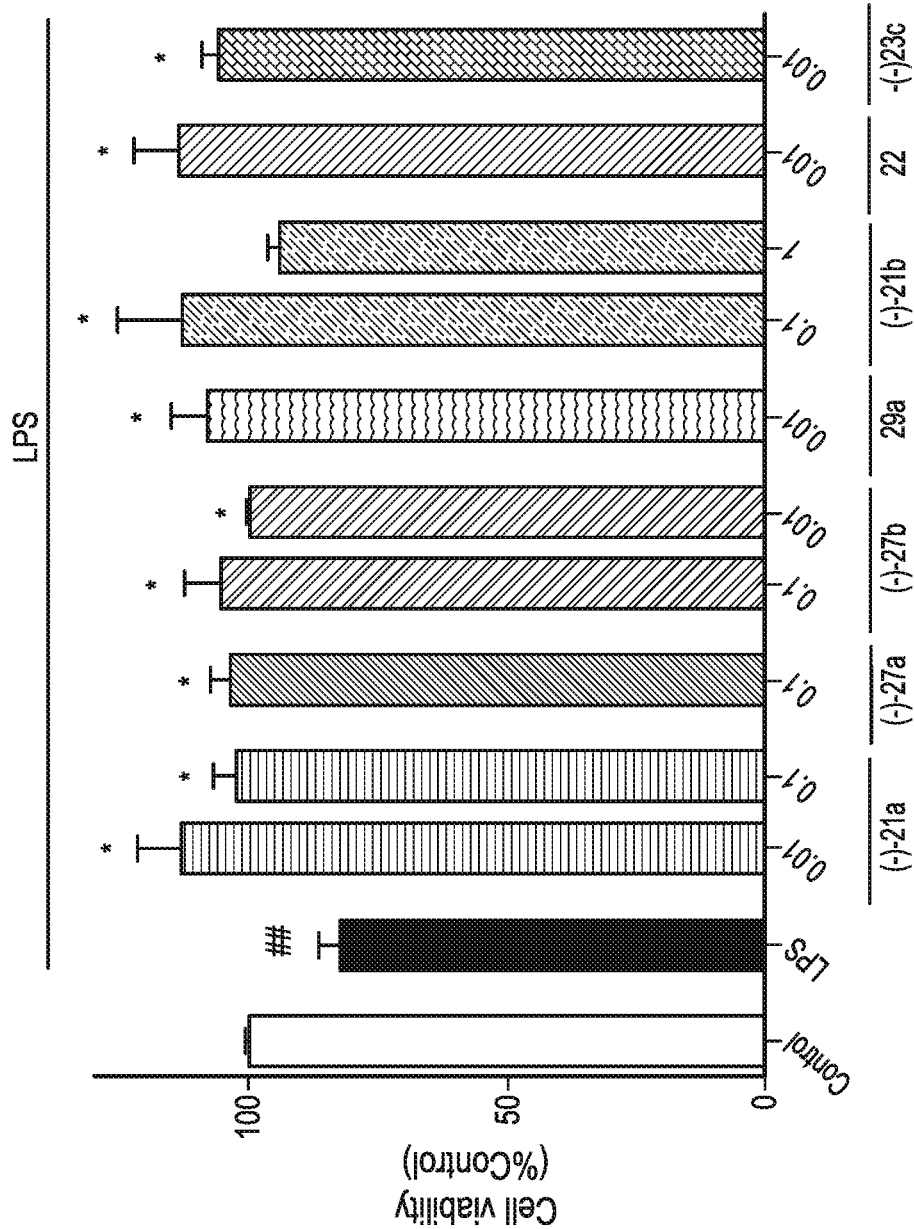

Results are presented as mean±SEM of three replicates performed by triplicate. $*p<0.05$, $p<0.01$, $*p<0.001$. Nuclear expression of the transcription factors Nrf2 and NFκB-p65 in BV2 microglial cells are compared in FIG. 8C. Protein expression levels were normalized with lamin B1. Cells treated with compounds are compared to LPS control cells ($*p<0.05$, $p<0.01$, $*p<0.001$). LPS control cells are compared to inactivated cells ($\#p<0.05$, $\#\#p<0.01$). Gracilin A derivatives protected SH-SY5Y neuroblastoma cells from activated microglia in a trans-well co-culture. BV2 cells were seeded in inserts placed above SH-SY5Y cells and the cell viability of neuroblastoma was determined as shown in FIG. 8D. Results are expressed as percentage of SH-SY5Y cells co-cultured with inactivated microglia (control). One way ANOVA and Dunnett's post hoc tests were used to analyse the statistical differences between treatments and neuroblastoma cells co-cultured with BV2 cells treated with LPS alone (LPS) ($*p<0.05$).

LPS control cells are compared to control cells ($\#\#p<0.01$).

The following examples are provided for the purpose of illustrating, not limiting the invention.

Example A

Synthesis of Representative Gracilin Derivatives

In this example, the synthesis and characterization of representative gracilin derivatives of the invention are described.

General Procedures

All non-aqueous reactions were performed under a nitrogen atmosphere in oven-dried glassware. Dichloromethane ($CH_2Cl_2$), tetrahydrofuran (THF), diethyl ether ($Et_2O$), acetonitrile ($CH_3CN$) and toluene (PhMe) were dried by filtration through activated alumina (solvent purification system). Diisopropylethylamine (EtN($^i$Pr)₂) and triethylamine (Et₃N) were distilled from calcium hydride prior to use. Other solvents and reagents were used as received from commercially available sources. Deuterated solvents were purchased from Cambridge Isotopes and used as received. ¹H NMR spectra were measured at 500 MHz and referenced relative to residual chloroform (7.26 ppm) or benzene (7.16 ppm) and were reported in parts per million. Coupling constants (J) were reported in Hertz (Hz), with multiplicity reported following usual convention: s, singlet; d, doublet; t, triplet; q, quartet; dd, doublet of doublets; dt, doublet of triplets; dq, doublet of quartets; dq, doublet of quartets; td, triplet of doublets; tt, triplet of triplets; ddd, doublet of doublet of doublets; ddt, doublet of doublet of triplets; ddq, doublet of doublet of quartets; dddd, doublet of doublet of doublet of doublets; ddddt, doublet of doublet of doublet of triplets; ddquint, doublet of doublet of quintets; m, multiplet, br s, broad singlet. ¹³C NMR spectra were measured at 125 MHz and referenced relative to chloroform-d signal (77.23 ppm) or benzene (128.06 ppm) and were reported in parts per million (ppm). Flash column chromatography was performed with 60 Å Silica Gel (230-400 mesh) as stationary phase on an automated flash chromatography system (EtOAc/hexanes as eluent unless indicated otherwise). High-resolution mass spectra (ESI) were obtained through the Laboratory for Biological Mass Spectrometry (Texas A&M University). Thin Layer Chromatography (TLC) was performed using glass-backed silica gel F254 (Silicycle, 250 μm thickness). Visualization of developed plates was performed by fluorescence quenching or by treating with Seebach's staining solution. Fourier Transform Infrared (FTIR) spectra were recorded as thin films on NaCl plates. Optical rotations were recorded on a polarimeter at 589 nm employing a 25 mm cell. High Performance Liquid Chromatography (HPLC) was performed on a chromatographic system using various chiral columns (25 cm) as noted. X-ray diffraction was obtained by the X-ray Diffraction Laboratory at Texas A&M University. (S)-(−)-TM.HCl was purchased from TCI chemicals and used as received. All other chemicals were purchased from Sigma-Aldrich or Alfa Aesar and used as received without further purification.

Abbreviation List
EtN($^i$Pr)₂ N,N-Diisopropylethylamine
Et₃N Triethylamine
NaBH₄ Sodium borohydride
(S)-(−)-TM.HCl (S)-(−)-Tetramisole (levamisole) hydrochloride
LiAlH₄ Lithium aluminum hydride
TBAF Tetrabutylammonium fluoride
Me₂S Dimethyl sulfide
(COCl)₂ Oxalyl chloride
DMAP 4-(Dimethylamino)pyridine
Ac₂O Acetic anhydride
DIBAl-H Diisobutylaluminum hydride
DBU 1,8-Diazabicyclo(5.4.0)undec-7-ene Preparation of Compounds (±)-9a, (±)-9b, (−)-15a, (+)-15b, 16, 17, 18, (−)-19, (±)-20a, (−)-21a, (−)-27, (−)-28, (−)-21b, (−)-22, (−)-23a, (−)-23b, (−)-23c, (−)-23d, (−)-24, (−)-26, (−)-27, (−)-28, (+)-15a, (+)-19, S3, (+)-21b, (+)-30, (+)-31a, (+)-31b, (±)-S7

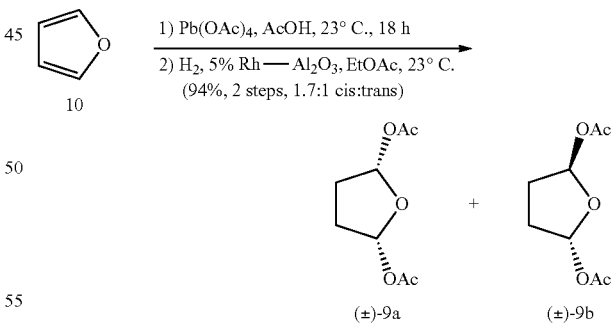

cis- and trans-2,5-tetrahydrofuran-2,5-diyl diacetate ((±)-9a and (±)-9b): To a suspension of Pb(OAc)₄ (2.0 g, 4.54 mmol, 1.1 equiv) in glacial AcOH (10 mL) was added furan 10 (0.30 mL, 4.13 mmol, 1.0 equiv) and the mixture was stirred at 23° C. for 20 h. AcOH was evaporated and Et₂O was added to the residue. The precipitate was filtered, the filtrate was collected, evaporated and the residue was redissolved in anhydrous EtOAc (50 mL). 5% Rhodium on alumina (180 mg) was added and the hydrogenation was carried out under hydrogen atmosphere (1 atm, balloon) for 24 h. The solution was filtered through Celite, the filtrate was concentrated by rotary evaporation and purified by an automated flash chromatography system (5→50% EtOAc/hexanes) providing 721 mg (94% yield, 2 steps) of (±)-9a and (±)-9b as a clear colorless oil and as a mixture of two isomers (ratio 1.7:1 cis:trans, according to 500 MHz H-NMR). IR (thin film): 2921, 2851, 1745 cm$^{-1}$; HRMS (ESI+) m/z calcd for $C_8H_{12}LiO_5$ [M+Li]$^+$: 195.0847, found: 195.0845. Spectral data matched that previously reported (Lee, S., Kaib, P. S. J. and List, B. *J. Am. Chem. Soc.*, 2017, 139, 2156-2159).

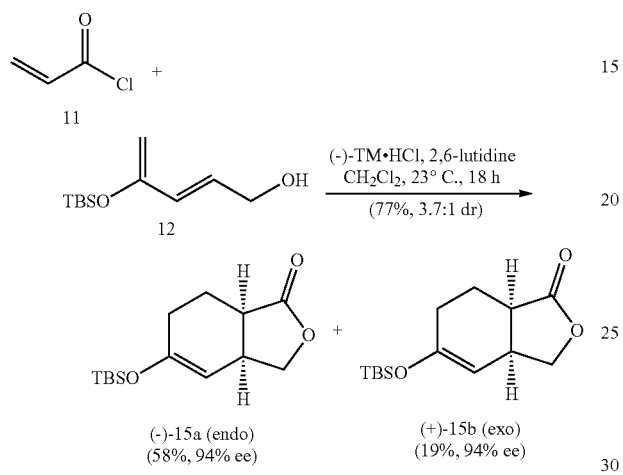

(3aS,7aR)-5-((tert-butyldimethylsilyl)oxy)-3a,6,7,7a-tetrahydroisobenzofuran-1(3H)-one ((−)-15a) and (3aR,7aR)-5-((tert-butyldimethylsilyl)oxy)-3a,6,7,7a-tetrahydroisobenzofuran-1(3H)-one ((+)-15b): To an oven-dried, 250-mL round-bottomed flask equipped with a magnetic stir bar was added silyloxydiene alcohol 12 (Abbasov, M. E., Hudson, B. M., Tantillo, D. J. and Romo, D. *J. Am. Chem. Soc.*, 2014, 136, 4492-4495) (2.14 g, 10.0 mmol, 1.0 equiv), (S)-(−)-TM·HCl (2.40 g, 10.0 mmol, 1.0 equiv), 2,6-lutidine (3.5 mL, 30.0 mmol, 3.0 equiv) and anhydrous $CH_2Cl_2$ (100 mL, to make final concentration of silyloxydiene alcohol 0.1 M) at ambient temperature (23° C.). With vigorous stirring, 11 (1.05 mL, 13.0 mmol, 1.3 equiv) in $CH_2Cl_2$ (9.0 mL) was added over a period of 5 h by syringe pump addition. After stirring for an additional 13 h, the reaction mixture was filtered through a short pad of $SiO_2$ and the filtrate was concentrated by rotary evaporation. Purification by automated flash chromatography (5→50% EtOAc/hexanes) afforded bicyclic γ-lactones (−)-15a (1.55 g, 58% yield, 94% ee) and (+)-15b (0.51 g, 19% yield, 94% ee).

(−)-15a: white crystalline solid; TLC (EtOAc/hexanes, 1:4 v/v), $R_f$=0.45; $[\alpha]_D^{20.1}$=−32.77 (c=0.82, CHCl$_3$); Enantiomeric excess was determined by chiral HPLC analysis in comparison with authentic racemic material using a Chiralcel OD-H column: hexanes:$^i$PrOH=95:05, flow rate 0.5 mL/min, λ=210 nm: $t_{major}$=13.5 min, $t_{minor}$=15.2 min, 94% ee (Figure S1); $^1$H NMR (500 MHz, CDCl$_3$) δ 4.76-4.73 (m, 1H), 4.32 (dd, J=8.8, 5.9 Hz, 1H), 3.98 (dd, J=8.8, 2.0 Hz, 1H), 3.17-3.11 (m, 1H), 2.74 (dt, J=7.8, 4.3 Hz, 1H), 2.19-2.12 (m, 1H), 2.12-2.06 (m, 1H), 1.96-1.89 (m, 1H), 1.86-1.78 (m, 1H), 0.89 (s, 9H), 0.11 (s, 3H), 0.10 (s, 3H); $^{13}$C NMR (126 MHz, CDCl$_3$) δ 178.48, 153.66, 103.01, 73.13, 37.65, 35.50, 26.12, 25.69 (3), 20.58, 18.10, −4.26, −4.44; IR (thin film): 2929, 2857, 1754, 1660 cm$^{-1}$; HRMS (ESI+) m/z calcd for $C_{14}H_{24}NaO_3Si$ [M+Na]$^+$: 291.1392, found: 291.1387.

(+)-15b: clear colorless oil; TLC (EtOAc/hexanes, 1:4 v/v), $R_f$=0.65; $[\alpha]_D^{19.8}$=+23.84 (c=1.12, CHCl$_3$); $^1$H NMR (500 MHz, CDCl$_3$) δ 4.91 (d, J=1.3 Hz, 1H), 4.38 (dd, J=8.0, 6.6 Hz, 1H), 3.81 (dd, J=11.4, 8.0 Hz, 1H), 2.91-2.82 (m, 1H), 2.28-2.17 (m, 3H), 1.70-1.58 (m, 2H), 0.91 (s, 9H), 0.14 (s, 3H), 0.08 (s, 3H); $^{13}$C NMR (126 MHz, CDCl$_3$) δ 176.35, 154.19, 100.93, 71.74, 43.76, 41.00, 30.47, 25.68 (3), 20.87, 18.11, −3.46, −4.39. IR (thin film): 2930, 2857, 1777, 1640 cm$^{-1}$; HRMS (ESI+) m/z calcd for $C_{14}H_{24}NaO_3Si$ [M+Na]$^+$: 291.1392, found: 291.1394.

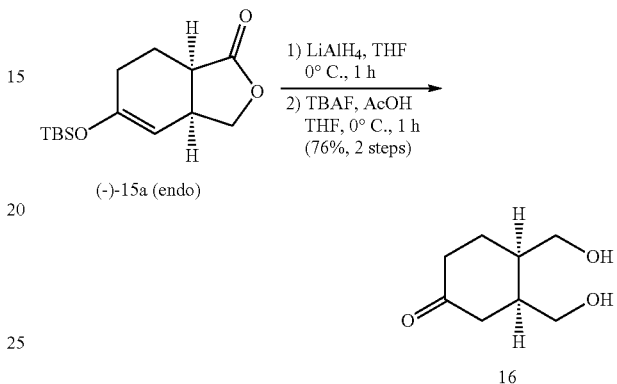

(3S,4R)-3,4-bis(hydroxymethyl)cyclohexan-1-one (16): To a 50 mL, single-necked, oven-dried, pear flask was added (−)-15a (493 mg, 1.85 mmol, 1.0 equiv) and 13.0 mL of THF. The resulting solution was cooled to 0° C. with an ice bath and stirred for 10 min before adding LiAlH$_4$ as a solution in THF (2.4 M, 1.68 mL, 4.04 mmol, 2.2 equiv) dropwise via plastic syringe. After addition was complete, the mixture was allowed to stir for 15 min at 0° C. before quenching by the method of Fieser (Fieser, L. F.; Fieser, M. *Reagents for Organic Synthesis*, 1967, 581-595). After quenching at 0° C. the reaction mixture is allowed to warm to ambient temperature (23° C.) with vigorous stirring over 3 h. MgSO$_4$ is then added to the mixture and the resulting slurry is filtered through Celite and the solvent removed by rotary evaporation, yielding an off-white oil which is used in the next step without purification.

To a 50 mL, single-necked, pear flask charged with the crude diol was added 5.0 mL of THF. The resulting solution was cooled to 0° C. with an ice bath and AcOH was added (0.53 mL, 9.20 mmol, 5.0 equiv) followed by TBAF as a solution in THF (1.0 M, 9.20 mL, 9.20 mmol, 5.0 equiv). The reaction mixture was then stirred for 1 h at 0° C. before removing the ice bath and allowing the mixture to warm to ambient temperature (23° C.) over 1 h. The reaction mixture was then concentrated by rotary evaporation and the resulting crude oil was purified by automated flash column chromatography (0→20% MeOH/EtOAc) to afford ketone diol 16 (220 mg, 76% yield, 2 steps) as a clear oil: TLC, $R_f$=0.51 (MeOH/EtOAc, 1:4 v/v).

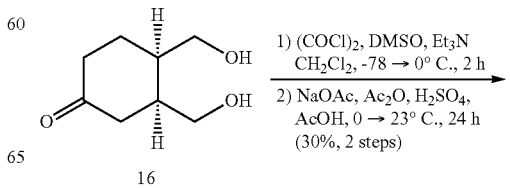

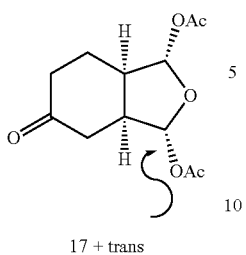

17 + trans

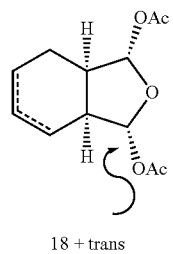

18 + trans (3aR,7aS)-1,3,3a,4,5,7a-hexahydroisobenzofuran-1,3-diyl diacetate (18): To a 50 mL, single-necked, oven-dried, pear flask charged with 17 (105 mg, 0.41 mmol, 1.0 equiv) was added 12.0 mL of THF. The resulting solution was cooled to 0° C. and stirred for 10 min before adding NaBH$_4$ (18 mg, 0.49 mmol, 1.2 equiv) in one portion. The resulting mixture was allowed to stir for 1 h at 0° C. before quenching with AcOH (50 µL, 0.87 mmol, 2.1 equiv) and warming to ambient temperature (23° C.). The mixture was concentrated by rotary evaporation to give a crude pale yellow oil which was used in the next step without purification.

To a 10 mL, single-necked, oven-dried, pear flask charged with crude material was added 3.0 mL of pyridine. The resulting solution was cooled to 0° C. and stirred for 10 min before adding SOCl$_2$ (87 µL, 1.20 mmol, 10.0 equiv). The cooling bath was removed and the mixture was allowed to warm to ambient temperature (23° C.) and stir for 3 h. The reaction mixture was then concentrated by high-vacuum rotary evaporation and the crude residue was purified by flash column chromatography (0→100% EtOAc/hexanes) to afford alkene bicycle 18 (16 mg, 17% yield over 2 steps) as a clear oil and a mixture of regioisomers and diastereomers as indicated in the scheme above. R$_f$=0.39 (EtOAc/hexanes, 1:1 v/v).

(1S,3R,3aS,7aR)-5-oxooctahydroisobenzofuran-1,3-diyl diacetate (17): To a 50 mL, single-necked, oven-dried, pear flask was added 10 mL of CH$_2$Cl$_2$ which was cooled to −78° C. and stirred for 10 min before adding (COCl)$_2$ (596 µL, 6.95 mmol, 5.0 equiv). The solution was then stirred for another 10 min before adding DMSO as a solution in anhydrous CH$_2$Cl$_2$ (2.8 M, 5.0 mL, 13.9 mmol, 10.0 equiv) slowly dropwise via plastic syringe. The resulting solution was stirred for 40 min at −78° C. Then diol 16 was added as a solution in CH$_2$Cl$_2$ (0.15 M, 220 mg, 1.39 mmol, 1.0 equiv) slowly dropwise via plastic syringe and stirred for 1 h. Et$_3$N was then added to the reaction mixture (3.87 mL, 27.8 mmol, 20.0 equiv) slowly dropwise via plastic syringe. The reaction mixture was then stirred for 30 min at −78° C. before replacing cooling bath with a 0° C. ice bath and stirring for 1 h. The reaction mixture was quenched with saturated, aqueous NaHCO$_3$, extracted with CH$_2$Cl$_2$ (3×15 mL), dried over MgSO$_4$, filtered through Celite, and concentrated by rotary evaporation to give a crude oil which was used in the next step without purification.

To a 50 mL, single-necked, pear flask charged with crude material was added 7.0 mL of AcOH and 7.0 mL of Ac$_2$O, followed by NaOAc (1.14 g, 13.9 mmol, 10.0 equiv) and concentrated H$_2$SO$_4$ (74 µL, 1.39 mmol, 1.0 equiv). The reaction mixture was stirred at ambient temperature (23° C.) for 48 h, poured into saturated aqueous NaHCO$_3$ solution (50 mL), and the aqueous layer was extracted with EtOAc (3×50 mL). The combined organic layer was washed with brine (20 mL), dried over MgSO$_4$, filtered through celite, and concentrated under reduced pressure to give a crude oil which was purified by automated flash column chromatography (0→100% EtOAc/hexanes) to afford bis-acetoxy furanose 17 (105 mg, 30% over 2 steps) as a mixture of two diastereomers with the appearance of an amber oil: TLC, R$_f$=0.39 (EtOAc/hexanes, 1:1 v/v).

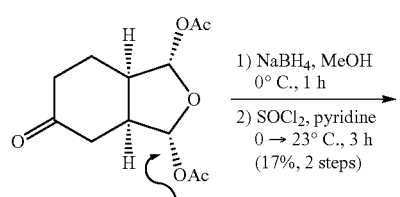

17 + trans

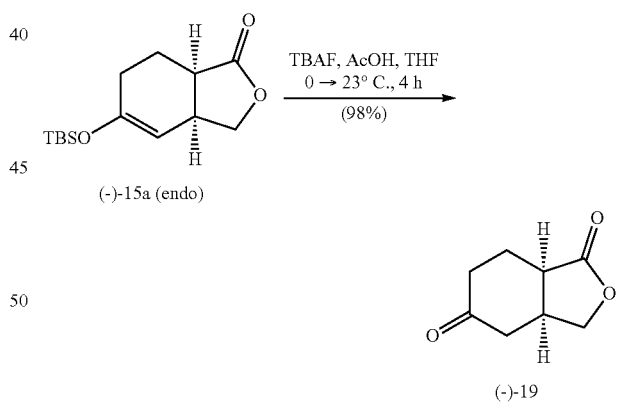

(3aS,7aR)-tetrahydroisobenzofuran-1,5(3H,4H)-dione ((−)-19): To a pre-cooled solution (0° C.) of silylenol ether (−)-15a (495 mg, 1.84 mmol, 1.0 equiv) and glacial AcOH (0.22 mL, 3.69 mmol, 2.0 equiv) in anhydrous THF (18.0 mL) was added TBAF (1.0 M in THF, 3.7 mL, 3.69 mmol, 2.0 equiv) dropwise. The reaction mixture was allowed to warm slowly up to ambient temperature (23° C.) over 4 h, and then concentrated by rotary evaporation. Purification by automated flash chromatography (5→80% EtOAc/hexanes) afforded ketolactone (−)-19 (278 mg, 98% yield).

(−)-19: clear colorless oil; TLC (EtOAc/hexanes, 1:1 v/v), R$_f$=0.23; [α]$_D^{20.0}$=−57.63 (c=0.38. CHCl$_3$); $^1$H NMR (500

MHz, CDCl$_3$) δ 4.39 (dd, J=9.4, 6.1 Hz, 1H), 3.98 (dd, J=9.4, 2.3 Hz, 1H), 3.08-2.98 (m, 1H), 2.94-2.86 (m, 1H), 2.53 (dd, J=15.2, 6.4 Hz, 1H), 2.38-2.26 (m, 4H), 2.21-2.10 (m, 1H); $^{13}$C NMR (126 MHz, CDCl$_3$) δ 209.03, 177.64, 71.67, 41.21, 38.14, 37.34, 35.72, 22.72; IR (thin film): 2934, 2864, 1771, 1712 cm$^{-1}$; HRMS (ESI+) m/z calcd for C$_8$H$_{11}$O$_3$ [M+H]$^+$: 155.0708, found: 155.0711.

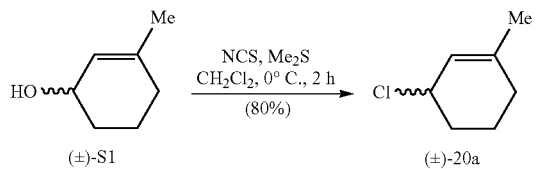 [SMILES: CC1=CC(O)CCC1 ; CC1=CC(Cl)CCC1]

3-Chloro-1-methylcyclohex-1-ene ((±)-20a): N-chlorosuccinimide (2.48 g, 18.6 mmol, 1.1 equiv) was weighed into an oven-dried, round-bottomed flask and suspended in CH$_2$Cl$_2$ (33.0 mL). The slurry was cooled to 0° C. and Me$_2$S (1.61 mL, 21.9 mmol, 1.3 equiv) was added dropwise over ~5 min producing a white solution. 3-methylcyclohex-2-en-1-ol ((±)-S1) (2.0 mL, 16.8 mmol, 1.0 equiv) was added dropwise with vigorous stirring to provide a clear solution. Within ~10 min, a precipitate formed. The reaction was continued at 0° C. for 2 h and concentrated under reduced pressure. Pentane (50 mL) was added leading to immediate formation a white precipitate. The flask was then placed in a freezer for 4 h and the supernatant was decanted. The remaining solid was washed with cold pentane (2×50 mL) and the combined organics were washed with brine (2×50 mL), dried over MgSO$_4$, and concentrated in vacuo. Allyl chloride (±)-20a was isolated as a clear colorless oil, (1.76 g, 80%) and this material was of sufficient purity (>95% as judged by $^1$H-NMR) to be carried directly to the next step without purification. TLC (EtOAc/hexanes, 3:7 v/v), R$_f$=0.79. Spectral data matched that previously reported (Ren, H., Dunet, G., Mayer, P. and Knochel, P. *J. Am. Chem. Soc.*, 2007, 127, 5376-5377).

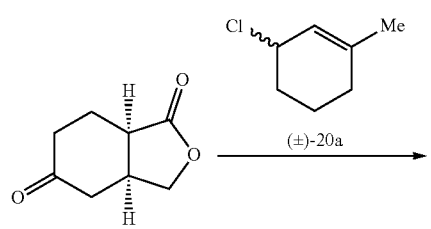

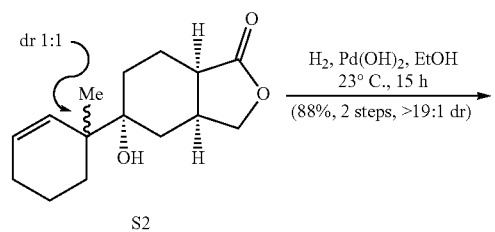

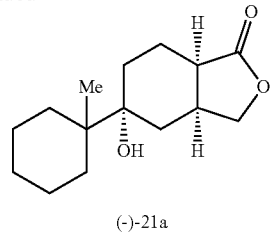

(3aS,5R,7aR)-5-hydroxy-5-(1-methylcyclohexyl)hexahydroisobenzofuran-1(3I)-one ((−)-21a): To an oven-dried round-bottomed flask was added zinc powder (2.3 g, 35.0 mmol, 25 equiv) and LiCl (300 mg, 7.0 mmol, 5.0 equiv) with a large bore vacuum adapter with Teflon lined seal for addition of liquids via syringe. The flask and solids were then carefully flame-dried under high vacuum (using a vacuum/N$_2$ double manifold) by repeated heating and cooling cycles with swirling of the solids to avoid the solids from clumping. After the final cycle of heating, the solids were allowed to cool for 3 min under N$_2$, and then anhydrous THF (20.0 mL) was slowly and carefully added with vigorous stirring. After addition of THF, 1,2-dibromoethane (0.12 mL, 1.4 mmol, 1.0 equiv) was added which sometimes led to an exotherm simultaneous with rapid gas evolution, which needs to be controlled. Pressure fluctuations generated upon addition of 1,2-dibromethane were controlled by momentarily switching the manifold from N$_2$ to vacuum. [Note: If gas evolution was not observed upon addition of 1,2-dibromoethane, a heat gun was employed to initiate gas evolution]. The solution was allowed to cool at ambient temperature over ~5 min before being further cooled to 0° C. A solution of (−)-19 (215 mg, 1.4 mmol, 1.0 equiv) in THF (1.0 mL) was added dropwise by syringe followed by slow addition of (±)-20a (1.65 g, 12.6 mmol, 9.0 equiv) in THF (4.0 mL) via syringe pump at a rate of 1.0 mL/h. During this time, the reaction mixture was allowed to slowly warm to ambient temperature (23° C.). The reaction mixture was then quenched with saturated NH$_4$Cl solution (100 mL). The organic phase was separated and the aqueous phase was further extracted with EtOAc (3×100 mL). The organic layers were combined, washed with brine (200 mL), dried with MgSO$_4$, and concentrated in vacuo to afford cyclohexenol lactone S2 as a crude pale yellow oil and as an inseparable mixture of two diastereomers (1:1 dr, based on $^1$H-NMR analysis of the crude mixture) which was used in the next step without purification.

To a solution of the above crude cyclohexenol lactone S2 (267 mg, 1.07 mmol, 1.0 equiv) in absolute EtOH (25.0 mL) and under an atmosphere of N$_2$ was added Pd(OH)$_2$ on carbon (300 mg, 20 wt %, 2.14 mmol, 2.0 equiv). A H$_2$ balloon was attached to the flask and after three consecutive cycles of evacuation (under high vacuum) and H$_2$ purge, the mixture was stirred for 15 h. An aliquot was removed for H-NMR analysis to ensure complete hydrogenation of the cyclohexene moiety. The reaction mixture was filtered through a pad of Celite, washed with EtOAc and concentrated in vacuo. Purification by automated flash chromatography (5→60% EtOAc/hexanes) afforded cyclohexanol lactone (−)-21a (307 mg, 88% yield over 2 steps) as a single diastereomer (>19:1 dr, based on $^1$H-NMR analysis of the crude mixture).

(−)-21a: colorless crystalline solid; TLC (EtOAc/hexanes, 1:1 v/v), R$_f$=0.43; [α]$_D^{17.0}$=−34.15 (c=0.41, CHCl$_3$); Absolute stereochemistry was assigned by analogy to cyclohexenol lactone (−)-21b; $^1$H NMR (500 MHz, CDCl$_3$) δ 4.23 (ddd, J=8.8, 4.7, 0.7 Hz, 1H), 3.91 (d, J=8.9 Hz, 1H), 2.75 (dq, J=11.9, 6.2 Hz, 1H), 2.63 (t, J=6.4 Hz, 1H), 2.10-1.92 (m, 2H), 1.84 (ddd, J=13.8, 6.0, 2.9 Hz, 1H), 1.66-1.50 (m, 4H), 1.45-1.19 (m, 9H), 1.07-0.95 (m, 1H), 0.88 (s, 3H); $^{13}$C NMR (126 MHz, CDCl$_3$) δ 178.65, 75.45, 72.07, 40.06, 38.94, 33.21, 31.34, 30.43, 30.35, 26.36, 26.27, 22.03 (2), 18.65, 17.22; IR (thin film): 3509, 2966, 2929, 2862, 1747 cm$^{-1}$; HRMS (ESI+) m/z calcd for C$_{15}$H$_{25}$O$_3$ [M+H]$^+$: 253.1804, found: 253.1793.

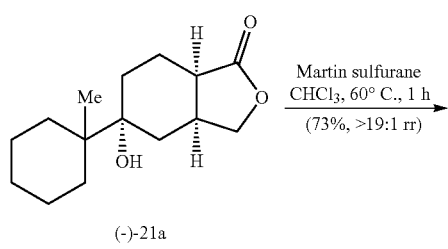

(−)-21a

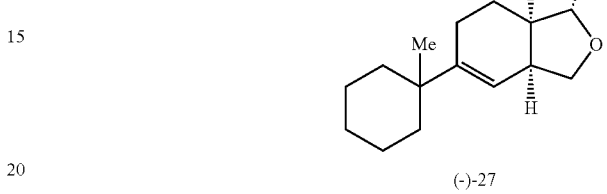

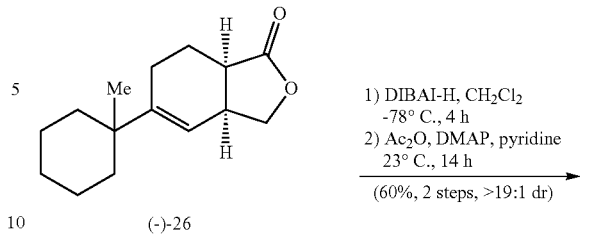

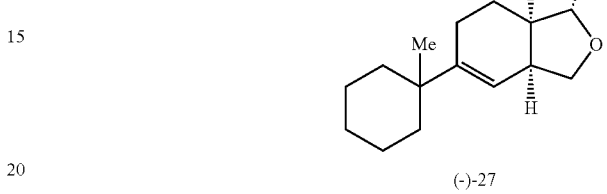

(−)-26

(3aS,7aR)-5-(1-methylcyclohexyl)-3a,6,7,7a-tetrahydroisobenzofuran-1(3H)-one ((−)-26): A glass tube was charged with a solution of (−)-21a (268 mg, 1.07 mmol, 1.0 equiv) in anhydrous CHCl$_3$ (35.0 mL) and Martin Sulfurane dehydrating agent (1.44 g, 2.14 mmol, 2.0 equiv). The tube was sealed and placed in a 60° C. oil bath for 1 h. The reaction mixture was cooled to ambient temperature (23° C.), concentrated under reduced pressure and purified by automated flash chromatography (5→30% EtOAc/hexanes) to afford alkene lactone (−)-26 (182 mg, 73% yield) as a single regioisomer (>19:1 rr, based on $^1$H-NMR analysis of the crude mixture).

(−)-26: clear colorless oil; TLC (EtOAc/hexanes, 1:4 v/v), R$_f$=0.40; [α]$_D^{16.9}$=−72.31 (c=0.26, CHCl$_3$); Absolute stereochemistry was assigned by analogy to cyclohexenol lactone (−)-21b; $^1$H NMR (500 MHz, CDCl$_3$) δ 5.38 (s, 1H), 4.38 (dd, J=8.8, 6.7 Hz, 1H), 4.02 (dd, J=8.8, 3.0 Hz, 1H), 3.10 (dtq, J=8.4, 5.3, 3.1 Hz, 1H), 2.76 (dt, J=8.0, 4.9 Hz, 1H), 2.08 (dt, J=13.3, 4.8 Hz, 1H), 2.02-1.88 (m, 2H), 1.73 (dddd, J=13.1, 10.0, 5.4, 4.7 Hz, 1H), 1.69-1.58 (m, 2H), 1.48-1.17 (m, 8H), 0.92 (s, 3H); $^{13}$C NMR (126 MHz, CDCl$_3$) δ 179.14, 147.95, 117.80, 72.89, 38.86, 37.91, 37.85, 36.08, 35.97, 27.03, 26.43, 22.73, 22.52, 21.35, 20.81; IR (thin film): 2927, 2854, 1771 cm$^{-1}$; HRMS (ESI+) m/z calcd for C$_{15}$H$_{22}$LiO$_2$ [M+Li]$^+$: 241.1780, found: 241.1793.

(1S,3aS,7aR)-5-(1-methylcyclohexyl)-1,3,3a,6,7,7a-hexahydroisobenzofuran-1-yl acetate ((−)-27): To a solution of (−)-26 (30 mg, 0.128 mmol, 1.0 equiv) in CH$_2$Cl$_2$ (2.0 mL) was added DIBAl-H (1.0 M solution in CH$_2$Cl$_2$, 154 µL, 0.154 mmol, 1.2 equiv) dropwise at −78° C. The reaction mixture was stirred at −78° C. for 4 h and carefully quenched in sequence with 6 µL H$_2$O, 11 µL 15% aqueous NaOH, and 16 µL H$_2$O. The dry-ice bath was removed and the mixture was allowed slowly warm to ambient temperature (23° C.). Subsequently, anhydrous MgSO$_4$ was added and the reaction mixture was vigorously stirred for 30 min, filtered through a pad of Celite and concentrated by rotary evaporation. The crude lactol was of sufficient purity (>95% as judged by $^1$H-NMR) to be carried on directly to the next step.

To a solution of the above crude lactol in anhydrous pyridine (1.0 mL) was added DMAP (2.0 mg, 0.012 mmol, 0.1 equiv) and Ac$_2$O (120 µL, 1.28 mmol, 10.0 equiv). The reaction mixture was stirred at ambient temperature (23° C.) for 14 h, poured into saturated aqueous NaHCO$_3$ solution (10 mL), and the aqueous layer was extracted with CH$_2$Cl$_2$ (3×10 mL). The combined organic layer was washed with brine (10 mL), dried over MgSO$_4$, filtered, and concentrated under reduced pressure. Purification by automated flash chromatography (0→30% EtOAc/hexanes) afforded acetyl lactol (−)-27 (21 mg, 60% yield over 2 steps) as a single diastereomer (>19:1 dr, based on H-NMR analysis of the crude mixture).

(−)-27: clear colorless oil; TLC (EtOAc/hexanes, 1:4 v/v), R$_f$=0.49; [α]$_D^{19.1}$=−53.33 (c=0.15, CHCl$_3$); Absolute stereochemistry was assigned by analogy to cyclohexenol lactone (−)-21b; $^1$H NMR (500 MHz, CDCl$_3$) δ 6.04 (s, 1H), 5.44 (dd, J=4.3, 1.6 Hz, 1H), 4.28 (t, J=8.2 Hz, 1H), 3.65 (t, J=7.8 Hz, 1H), 3.00 (q, J=7.5 Hz, 1H), 2.30 (ddd, J=11.6, 7.3, 4.4 Hz, 1H), 2.13-2.08 (m, 1H), 2.07 (s, 3H), 1.96-1.87 (m, 1H), 1.84 (dq, J=13.5, 4.5 Hz, 1H), 1.71-1.62 (m, 3H), 1.52-1.22 (m, 8H), 0.95 (s, 3H); $^{13}$C NMR (126 MHz, CDCl$_3$) δ 170.77, 145.87, 117.56, 103.91, 74.92, 43.14, 38.68, 36.56, 36.26, 36.03, 27.10, 26.54, 22.86, 22.79, 22.69, 22.54, 21.53; IR (thin film): 2931, 2857, 1746 cm$^{-1}$; HRMS (ESI+) m/z calcd for C$_{17}$H$_{26}$LiO$_3$ [M+Li]$^+$: 285.2042, found: 285.2052.

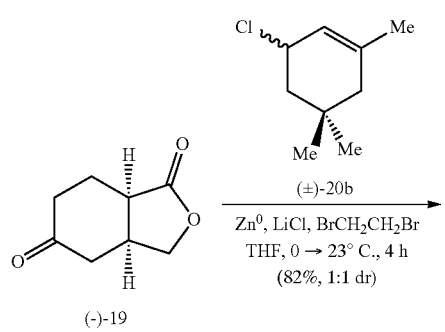

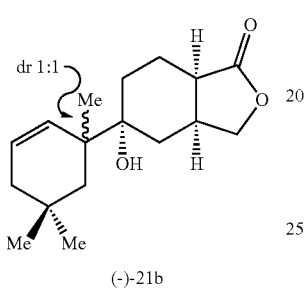

(3aS,5R,7aR)-5-hydroxy-5-(1,5,5-trimethylcyclohex-2-en-1-yl)hexahydroisobenzo-furan-1(3H)-one ((−)-21b): To an oven-dried round-bottomed flask was added zinc powder (2.3 g, 35.0 mmol, 25 equiv) and LiCl (300 mg, 7.0 mmol, 5.0 equiv) with a large bore vacuum adapter with Teflon lined seal for addition of liquids via syringe. The flask and solids were then carefully flame-dried under high vacuum (using a vacuum/$N_2$ double manifold) by repeated heating and cooling cycles with swirling of the solids to avoid the solids from clumping. After the final cycle of heating, the solids were allowed to cool for 3 min under $N_2$, and then anhydrous THF (20.0 mL) was slowly and carefully added with vigorous stirring. After addition of THF, 1,2-dibromoethane (0.12 mL, 1.4 mmol, 1.0 equiv) was added which sometimes led to an exotherm simultaneous with rapid gas evolution, which needs to be controlled. Pressure fluctuations generated upon addition of 1,2-dibromoethane were controlled by momentarily switching the manifold from $N_2$ to vacuum. [Note: If gas evolution was not observed upon addition of 1,2-dibromoethane, a heat gun was employed to initiate gas evolution]. The solution was allowed to cool at ambient temperature over ~5 min before being further cooled to 0° C. A solution of keto lactone (−)-19 (215 mg, 1.4 mmol, 1.0 equiv) in THF (1.0 mL) was added dropwise by syringe followed by slow addition of allyl chloride (±)-20b (Harvey, N. L., Krysiak, J., Chamni, S., Cho, S. W., Sieber, S. A. and Romo, D. *Chem. Eur. J.,* 2015, 21, 1425-1428) (2.22 g, 14.0 mmol, 10 equiv) in THF (4.0 mL) via syringe pump at a rate of 1.0 mL/h. During this time, the reaction mixture was allowed to slowly warm to ambient temperature (23° C.). The reaction mixture was then quenched with saturated $NH_4Cl$ solution (100 mL). The organic phase was separated and the aqueous phase was further extracted with EtOAc (3×100 mL). The organic layers were combined, washed with brine (200 mL), dried with $MgSO_4$, and concentrated under reduced pressure. Purification by automated flash chromatography (5→60% EtOAc/hexanes) afforded dimethyl cyclohexenol lactone (−)-21b (318 mg, 82% yield) as an inseparable mixture of two diastereomers (1:1 dr, based on $^1$H-NMR analysis of the crude mixture).

(−)-21b: white crystalline solid, m.p. 161.2-163.7° C. (recrystallized from pentane); TLC (EtOAc/hexanes, 1:1 v/v), $R_f$=0.44; $[\alpha]_D^{17.3}$=−28.89 (c=0.18, $CHCl_3$); Absolute stereochemistry was assigned based on X-ray analysis using anomalous dispersion. $^1$H NMR (500 MHz, $CDCl_3$) δ 5.89 (ddd, J=9.9, 6.3, 2.1 Hz, 1H), 5.52 (dd, J=10.2, 1.8 Hz, 1H), 4.24 (dt, J=9.0, 4.5 Hz, 1H), 3.93 (dd, J=8.9, 4.3 Hz, 1H), 2.75 (tt, J=12.0, 6.1 Hz, 1H), 2.64 (q, J=5.5 Hz, 1H), 2.14-2.02 (m, 1H), 2.05-1.92 (m, 1H), 1.86-1.64 (m, 4H), 1.63-1.50 (m, 1H), 1.45-1.21 (m, 3H), 1.10 (dtd, J=13.6, 2.7, 1.3 Hz, 1H), 1.02 (s, 3H), 0.97 (s, 3H), 0.94 (s, 3H); $^{13}$C NMR (126 MHz, $CDCl_3$) δ 178.63, 130.27 (2), 75.44, 71.97, 43.43, 42.90, 39.05, 38.26, 33.22, 32.34, 30.92, 30.59, 27.20, 25.98, 22.16, 18.69; IR (thin film): 3518, 2951, 2867, 1766 cm$^{-1}$; HRMS (ESI+) m/z calcd for $C_{17}H27O3$ [M+H]*: 279.1960, found: 279.1963.

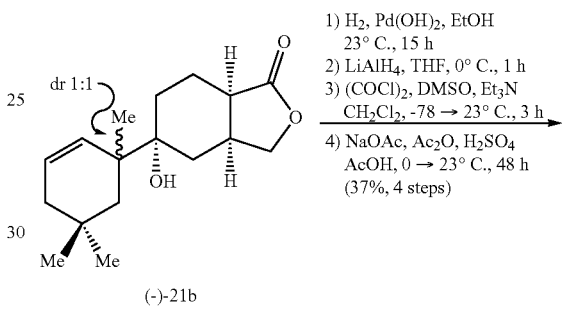

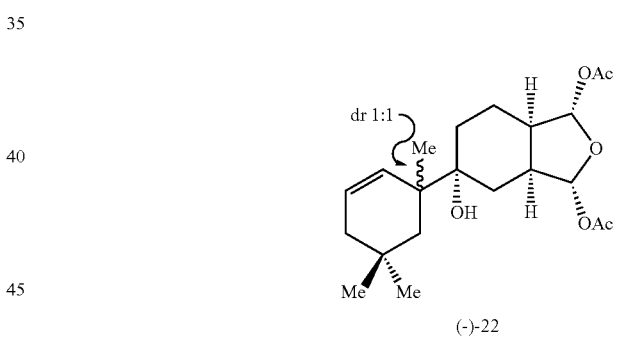

(1S,3R,3aS,5R,7aR)-5-hydroxy-5-(1,3,3-trimethylcyclohexyl)octahydroisobenzo-furan-1,3-diyl diacetate ((−)-22): To a solution of cyclohexenol lactone (−)-21b (281 mg, 1.01 mmol, 1.0 equiv) in absolute EtOH (20.0 mL) and under an atmosphere of $N_2$ was added $Pd(OH)_2$ on carbon (284 mg, 20 wt %, 2.02 mmol, 2.0 equiv). A $H_2$ balloon was attached to the flask and after three consecutive cycles of evacuation (under high vacuum) and $H_2$ purge, the mixture was stirred for 18 h. An aliquot was removed for $^1$H-NMR analysis to ensure complete hydrogenation of the cyclohexene moiety. The reaction mixture was filtered through a pad of Celite, washed with EtOAc, concentrated in vacuo, and taken on directly to the next step without purification.

To a solution of the above crude lactone in anhydrous THF (9.0 mL) was added $LiAlH_4$ (2.0 M solution in THF, 0.60 mL, 1.2 mmol, 2.7 equiv) dropwise at 0° C. After stirring for 20 min, the ice bath was removed and the mixture was allowed to slowly warm to ambient temperature (23° C.) over 40 min. Upon consumption of the starting material (as judged by TLC), the reaction mixture was cooled to 0° C. and carefully quenched in sequence with 50 μL H₂O, 85 μL 15% aqueous NaOH, and 120 μL H₂O. The ice bath was removed and the mixture was allowed to slowly warm to ambient temperature (23° C.). Subsequently, anhydrous MgSO₄ was added and the reaction mixture was vigorously stirred for 30 min, filtered through a pad of Celite and concentrated by rotary evaporation. The crude diol was of sufficient purity (>95% as judged by ¹H-NMR) to be carried on directly to the next step.

To a solution of (COCl)₂ (0.19 mL, 2.2 mmol, 10.0 equiv) in CH₂Cl₂ (15.0 mL) was added DMSO (0.31 mL, 4.4 mmol, 20.0 equiv) followed by a solution of the above crude diol in CH₂Cl₂ (5.0 mL) via syringe pump over 1 h at −78° C. To the reaction mixture was added Et₃N (0.92 mL, 6.6 mmol, 30.0 equiv) and the reaction mixture was stirred at −78° C. for 1 h, and then at ambient temperature (23° C.) for 1 h. The mixture was quenched with 2 N HCl (10 mL) and the aqueous layer was extracted with CH₂Cl₂ (3×50 mL). The combined organic layer was washed with brine (10 mL), dried over MgSO₄, filtered, and concentrated under reduced pressure. The crude dialdehyde was taken on directly to the next step without purification.

To a solution of the above crude dialdehyde in AcOH/Ac₂O (1.5:1, 4.5/3.0 mL) was added NaOAc (180 mg, 2.2 mmol, 10.0 equiv) and concentrated H₂SO₄ (11 μL, 0.22 mmol, 1.0 equiv) successively at 0° C. The reaction mixture was stirred at ambient temperature (23° C.) for 48 h, poured into saturated aqueous NaHCO₃ solution (10 mL), and the aqueous layer was extracted with EtOAc (3×50 mL). The combined organic layer was washed with brine (20 mL), dried over MgSO₄, filtered, and concentrated under reduced pressure. Purification by automated flash chromatography (0→20% EtOAc/hexanes) afforded cyclohaxanol diacetate (−)-22 (142 mg, 37% yield over 4 steps) as an inseparable mixture of two diastereomers (1:1 dr, based on ¹H-NMR analysis of the crude mixture).

(−)-22: white solid; TLC (EtOAc/hexanes, 1:4 v/v), $R_f$=0.10; $[\alpha]_D^{19.1}$=−10.53 (c=0.19, CHCl₃); Absolute stereochemistry was assigned by analogy to cyclohexenol lactone (−)-21b; ¹H NMR (500 MHz, CDCl₃) δ 6.17 (d, J=6.6 Hz, 1H), 5.94 (d, J=2.1 Hz, 1H), 2.65-2.57 (m, 1H), 2.59-2.49 (m, 1H), 2.12 (s, 3H), 2.08 (s, 3H), 2.02-1.77 (m, 2H), 1.70-1.47 (m, 5H), 1.42-1.21 (m, 7H), 1.15-1.09 (m, 1H), 1.01 (s, 3H), 1.00 (s, 3H), 0.91 (s, 3H); ¹³C NMR (126 MHz, CDCl₃) δ 170.93, 170.12, 103.22, 100.78, 75.72, 43.29, 41.48, 40.91, 39.15, 38.92, 36.16, 30.79 (2), 30.10, 28.82, 27.80, 25.45, 21.42, 20.51, 18.98, 18.54; IR (thin film): 3527, 2948, 2865, 1748 cm⁻¹; HRMS (ESI−) m/z calcd for C₂₁H₃₄ClO₆ [M+Cl]⁻: 417.2044, found: 417.2062.

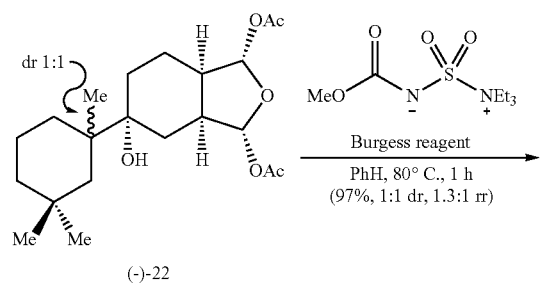

(−)-22

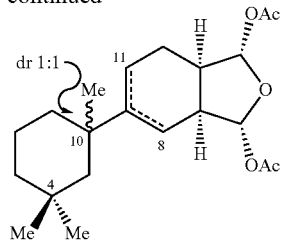

HPLC sep'n. 
(−)-23 (4 disastereomers)
[(−)-23a: 10 S, Δ⁹,¹¹; (−)-23b:10R, Δ⁹,¹¹
(−)-23c: 10S, Δ⁸,⁹;(−)-23d: 10 R, Δ⁸,⁹]

(1S,3R,3aS,7aR)-5-((S)-1,3,3-trimethylcyclohexyl)-1,3,3a,4,7,7a-hexahydroisoben-zofuran-1,3-diyl diacetate ((−)-23a), (1S,3R,3aS,7aR)-5-((R)-1,3,3-trimethylcyclo-hexyl)-1,3,3a,4,7,7a-hexahydroisobenzofuran-1,3-diyl diacetate ((−)-23b), (1R,3S,3aR,7aS)-6-((S)-1,3,3-trimethylcyclo-hexyl)-1,3,3a,4,5,7a-hexahydroisobenzofuran-1,3-diyl diacetate ((−)-23c), and (0R,3S,3aR,7aS)-6-((R)-1,3,3-trimethyl-ethyl-cyclohexyl)-1,3,3a,4,5,7a-hexahydroisobenzofuran-1,3-diyl diacetate ((−)-23)): A glass tube was charged with cyclohaxanol diacetate (−)-22 (20 mg, 0.052 mmol, 1.0 equiv) and methyl N-(triethylammoniosulfonyl)carbamate (Burgess reagent, 25 mg, 0.10 mmol, 2.0 equiv) in PhH (2.0 mL). The tube was sealed and placed in an 80° C. oil bath for 1 h. The reaction mixture was cooled to ambient temperature (23° C.) and concentrated under reduced pressure. Purification by automated flash chromatography (0→20% EtOAc/hexanes) afforded cyclohexenyl diacetate (−)-23 (18 mg, 97% yield) as a clear colorless oil and as an inseparable mixture of four diastereomers (1:1 dr, 1.3:1 rr, based on ¹H-NMR analysis of the crude mixture). TLC (EtOAc/hexanes, 1:4 v/v), $R_f$=0.32; $[\alpha]_D^{20.2}$=−280.1 (c=0.011, CHCl₃); Absolute stereochemistry was assigned by analogy to cyclohexenol lactone (−)-21b; IR (thin film): 2924, 2864, 1750 cm⁻¹; HRMS (ESI+) m/z calcd for C₂₁H₃₂NaO₅ [M+Na]⁺: 387.2147, found: 387.2151. This diastereomeric mixture was then subjected to a chiral HPLC purification using a Chiralcel OJ-H column: hexanes:ⁱPrOH=96:04, flow rate 0.4 mL/min, λ=210 nm: $t_{(−)-23a}$=11.4-13.5 min, $t_{(−)-23b}$=13.6-15.4 min, $t_{(−)-23c}$=15.5-17.5 min, $t_{(−)-23d}$=17.6-20.8 min.

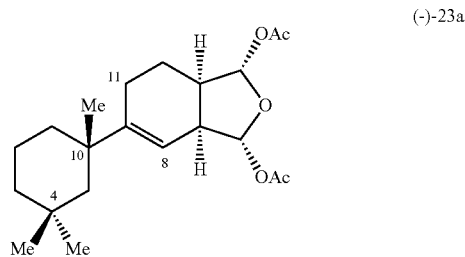

(−)-23a (−)-23a: ¹H NMR (500 MHz, CDCl₃) δ 6.11 (d, J=2.1 Hz, 1H), 6.03 (d, J=3.0 Hz, 1H), 5.50 (d, J=4.1 Hz, 1H), 2.96-2.92 (m, 1H), 2.52 (dddd, J=9.4, 7.3, 4.5, 2.2 Hz, 1H), 2.11 (s, 3H), 2.09 (s, 3H), 1.98-1.88 (m, 2H), 1.81-1.70 (m, 1H), 1.67-1.56 (m, 3H), 1.49-1.38 (m, 1H), 1.33-1.23 (m, 2H), 1.18-1.08 (m, 2H), 1.06-0.99 (m, 1H), 0.91 (s, 3H), 0.86 (s, 3H), 0.81 (s, 3H); ¹³C NMR (126 MHz, CDCl₃) δ 170.47, 170.33, 147.93, 114.39, 103.69, 103.10, 48.24, 44.10, 41.73, 40.41, 39.02, 36.32, 33.30, 31.55, 31.46, 26.71, 22.64, 21.79, 21.52, 21.49, 19.59.

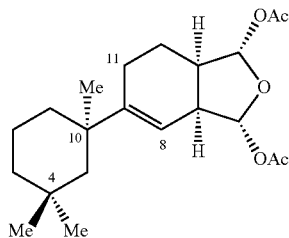

(−)-23b (−)-23b: 1H NMR (500 MHz, CDCl$_3$) δ 6.09 (d, J=1.5 Hz, 1H), 6.00 (d, J=3.6 Hz, 1H), 5.50 (d, J=4.3 Hz, 1H), 3.01-2.94 (m, 1H), 2.47 (dddd, J=9.7, 7.5, 4.6, 1.6 Hz, 1H), 2.11 (s, 3H), 2.09 (s, 3H), 2.00-1.90 (m, 2H), 1.86-1.80 (m, 1H), 1.66-1.52 (m, 2H), 1.48-1.36 (m, 2H), 1.33-1.23 (m, 2H), 1.19-1.08 (m, 2H), 1.04-0.98 (m, 1H), 0.91 (s, 3H), 0.86 (s, 3H), 0.81 (s, 3H); $^{13}$C NMR (126 MHz, CDCl$_3$) δ 170.37, 170.21, 147.82, 114.13, 104.02, 103.07, 47.67, 43.43, 41.99, 40.34, 38.88, 36.06, 35.10, 33.15, 31.40, 26.78, 24.62, 23.01, 22.53, 21.36, 19.38.

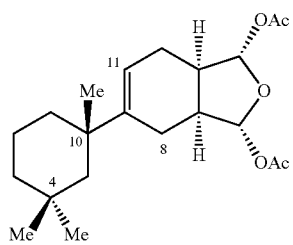

(−)-23c (−)-23c: 1H NMR (500 MHz, CDCl$_3$) δ 6.01 (d, J=2.5 Hz, 1H), 5.97 (d, J=2.7 Hz, 1H), 5.57 (t, J=4.4 Hz, 1H), 2.65-2.53 (m, 2H), 2.36-2.22 (m, 2H), 2.10 (s, 3H), 2.09 (s, 3H), 2.07-1.95 (m, 2H), 1.93-1.87 (m, 1H), 1.63-1.53 (m, 2H), 1.48-1.38 (m, 20 1H), 1.31-1.23 (m, 1H), 1.18-1.10 (m, 2H), 1.03 (d, J=14.0 Hz, 1H), 0.92 (s, 3H), 0.86 (s, 3H), 0.79 (s, 3H); $^{13}$C NMR (126 MHz, CDCl$_3$) δ 170.41, 170.34, 143.99, 116.76, 104.27, 104.05, 48.17, 42.11, 40.65, 40.35, 38.53, 36.19, 33.20, 31.40, 31.28, 27.10, 24.35, 23.66, 21.49 (2), 19.54.

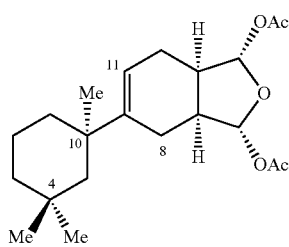

(−)-23d (−)-23d: $^1$H NMR (500 MHz, CDCl$_3$) δ 6.06 (d, J=1.8 Hz, 1H), 6.01 (d, J=3.1 Hz, 1H), 5.57 (dt, J=5.5, 2.8 Hz, 1H), 2.50 (ddt, J=10.2, 7.3, 3.1 Hz, 1H), 2.46-2.35 (m, 2H), 2.09 (s, 3H), 2.09 (s, 3H), 2.00-1.76 (m, 3H), 1.57 (d, J=13.7 Hz, 1H), 1.49-1.38 (m, 1H), 1.31-1.22 (m, 2H), 1.14 (ddd, J=13.8, 11.5, 3.6 Hz, 2H), 1.03 (d, J=13.9 Hz, 1H), 0.91 (s, 3H), 0.86 (s, 3H), 0.78 (s, 3H); $^{13}$C NMR (126 MHz, CDCl$_3$) δ 170.38, 170.30, 144.90, 116.91, 104.09, 103.66, 48.27, 43.18, 41.11, 40.27, 38.67, 36.07, 33.01, 31.40, 30.94, 27.17, 24.58, 24.52, 21.49, 21.47, 19.53.

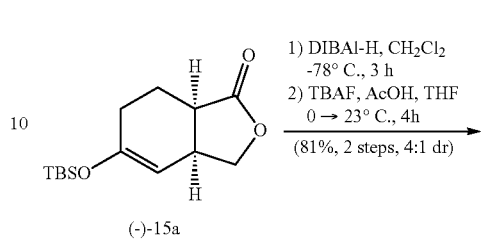

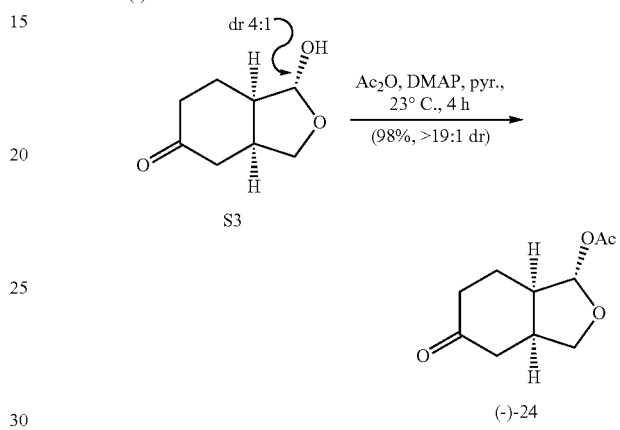

(1S,3aS,7aR)-5-oxooctahydroisobenzofuran-1-yl acetate ((−)-24): To a solution of lactone (−)-15a (72 mg, 0.268 mmol, 1.0 equiv) in CH$_2$Cl$_2$ (2.7 mL) was added DIBAl-H (1.0 M solution in CH$_2$Cl$_2$, 321 μL, 0.321 mmol, 1.2 equiv) dropwise at −78° C. The reaction mixture was stirred at −78° C. for 4 h and carefully quenched in sequence with 12 μL of H$_2$O, 12 μL of 20% aqueous NaOH, and 32 μL of H$_2$O. The dry-ice bath was removed and the mixture was allowed to slowly warm to ambient temperature (23° C.). Subsequently, anhydrous MgSO$_4$ was added and the reaction mixture was vigorously stirred for 30 min, filtered through a pad of Celite and concentrated under reduced pressure. The crude silyl enol ether lactol was of sufficient purity (>95% as judged by $^1$H-NMR) to be carried on directly to the next step.

To a pre-cooled solution (0° C.) of the above crude silyl enol ether lactol and glacial AcOH (31 μL, 0.536 mmol, 2.0 equiv) in anhydrous THF (2.7 mL) was added TBAF (1.0 M in THF, 0.54 mL, 0.536 mmol, 2.0 equiv) dropwise. The reaction mixture was allowed to slowly warm to ambient temperature (23° C.) over 4 h, and then concentrated under reduced pressure. Purification by automated flash chromatography (5→80% EtOAc/hexanes) afforded ketolactol S3 (42 mg, 81% yield over 2 steps) as a mixture of two diastereomers (4:1 dr, based on $^1$H-NMR analysis of the crude mixture).

S3: clear colorless oil; TLC (EtOAc/hexanes, 4:1 v/v), R$_f$=0.23; (NMR data is provided for the major diastereomer) $^1$H NMR (500 MHz, C$_6$D$_6$) δ 5.08 (s, 1H), 3.94 (dd, J=8.6, 7.4 Hz, 1H), 3.27 (dd, J=8.6, 5.6 Hz, 1H), 2.40 (q, J=7.0 Hz, 1H), 2.15-1.85 (m, 5H), 1.76 (ddd, J=16.4, 11.2, 5.2 Hz, 1H), 1.50-1.38 (m, 1H), 1.36-1.23 (m, 1H); $^{13}$C NMR (126 MHz, C$_6$D$_6$) δ 209.93, 103.43, 71.70, 44.13, 40.38, 37.76, 36.50, 23.83; IR (thin film): 3383, 2924, 1710 cm$^{-1}$; HRMS (ESI+) m/z calcd for C$_8$H$_{12}$LiO$_3$ [M+Li]$^+$: 163.0941, found: 163.0949.

To a solution of ketolactol S3 (20 mg, 0.128 mmol, 1.0 equiv) in anhydrous pyridine (1.0 mL) was added DMAP (2.0 mg, 0.012 mmol, 0.1 equiv) and Ac$_2$O (120 µL, 1.28 mmol, 10.0 equiv). The reaction mixture was stirred at ambient temperature (23° C.) for 18 h, poured into saturated aqueous NaHCO$_3$ solution (10 mL), and the aqueous layer was extracted with CH$_2$Cl$_2$ (3×10 mL). The combined organic layer was washed with brine (10 mL), dried over MgSO$_4$, filtered, and concentrated under reduced pressure. Purification by automated flash chromatography (0→40% EtOAc/hexanes) afforded acetyl ketolactol (−)-24 (24 mg, 98% yield) as a single diastereomer (>19:1 dr, based on $^1$H-NMR analysis of the crude mixture).

(−)-24: clear colorless oil; TLC (EtOAc/hexanes, 4:1 v/v), R$_f$=0.49; [α]$_D^{19.7}$=−21.08 (c=0.13, CHCl$_3$); $^1$H NMR (500 MHz, C$_6$D$_6$) δ 6.05 (s, 1H), 3.76 (dd, J=8.9, 7.7 Hz, 1H), 3.23 (dd, J=8.8, 5.8 Hz, 1H), 2.19-2.09 (m, 1H), 1.96-1.83 (m, 3H), 1.70-1.60 (m, 4H), 1.46-1.33 (m, 2H), 1.26-1.10 (m, 1H); $^{13}$C NMR (126 MHz, C$_6$D$_6$) δ 208.12, 169.37, 103.35, 73.17, 43.34, 39.90, 37.57, 35.88, 23.42, 20.89; IR (thin film): 2957, 2923, 2853, 1712 cm$^{-1}$; HRMS (ESI+) m/z calcd for C$_{10}$H$_{14}$LiO$_4$ [M+Li]$^+$: 205.1047, found: 205.1052.

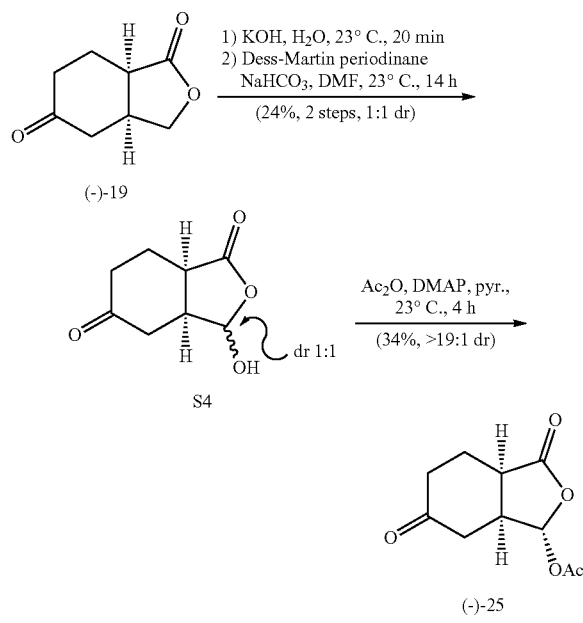

(1S,3aR,7aS)-3,6-dioxooctahydroisobenzofuran-1-yl acetate ((−)-25): To a stirred solution of ketolactone (−)-19 (21 mg, 0.134 mmol, 1.0 equiv) in H$_2$O (1.0 mL, 0.13 M) was added KOH (11 mg, 0.201 mmol, 1.5 equiv) at ambient temperature (23° C.) and stirred for 20 min. The solvent was removed under reduced pressure and azeotroped with PhMe (3×10 mL) to provide corresponding ketoacid as an amorphous solid.

To a pre-cooled solution (0° C.) of the above crude ketoacid in DMF (5.0 mL) was added Dess-Martin periodinane (292 mg, 0.688 mmol, 5.0 equiv) and NaHCO$_3$ (224 mg, 2.67 mmol, 20 equiv). The reaction mixture was allowed to slowly warm to ambient temperature (23° C.) and stirred for 20 h. The reaction mixture was then quenched with H$_2$O (20 mL) and extracted with EtOAc (2×20 mL). The combined organic layer was washed with brine (10 mL), dried over MgSO$_4$, filtered, and concentrated under reduced pressure. Purification by automated flash chromatography (5→80% EtOAc/hexanes) afforded hydroxy ketolactone S4 (5.5 mg, 24% yield over 2 steps) as an amorphous white solid and as a mixture of two diastereomers (1:1 dr, based on H-NMR analysis of the crude mixture). TLC (EtOAc/hexanes, 4:1 v/v), R$_f$=0.24.

To a stirred solution of hydroxyl ketolactone S4 (5.0 mg, 0.0294 mmol, 1.0 equiv) in pyridine (1.0 mL, 0.03 M) was added Ac$_2$O (28 µL, 0.294 mmol, 10 equiv) and DMAP (3.6 mg, 0.0294 mmol, 1.0 equiv) at ambient temperature (23° C.). The reaction mixture was stirred for 4 h at 23° C. and then concentrated under reduced pressure. The crude reaction mixture was subjected to purification by automated flash column chromatography (0→100% EtOAc/hexanes) to afford acetoxy ketolactone (−)-25 (2.1 mg, 34% yield) as a single diastereomer (>19:1 dr, based on H-NMR analysis of the crude mixture).

(−)-25: white solid; TLC (EtOAc/hexanes, 4:1 v/v), R$_f$=0.45; [α]$_D^{20.1}$=−11.53 (c=0.021, CHCl$_3$); $^1$H NMR (500 MHz, CDCl$_3$) δ 6.69 (d, J=6.2 Hz, 1H), 3.33 (dtd, J=10.4, 6.6, 4.2 Hz, 1H), 3.02 (dt, J=10.0, 6.7 Hz, 1H), 2.54-2.39 (m, 4H), 2.39-2.20 (m, 2H), 2.07 (s, 3H); $^{13}$C NMR (126 MHz, CDCl$_3$) δ 207.85, 176.43, 168.69, 94.73, 37.51, 36.47, 31.97, 23.53, 20.71, 17.32.

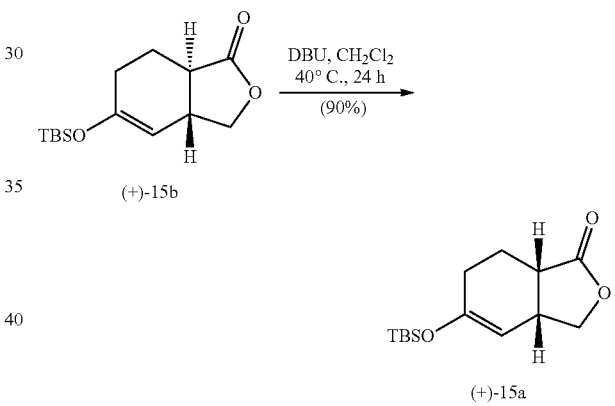

(3aR,7aS)-5-((tert-butyldimethylsilyl)oxy)-3a,6,7,7a-tetrahydroisobenzofuran-1(3H)-one ((+)-15a): To a glass tube containing a solution of trans-fused bicyclic γ-lactone (+)-15b (202 mg, 0.752 mmol, 1.0 equiv) in CH$_2$Cl$_2$ (7.5 mL, 0.1 M) was added DBU (0.34 mL, 2.25 mmol, 3.0 equiv). The glass tube was sealed and placed in a 40° C. oil bath for 24 h. The reaction mixture was cooled to ambient temperature (23° C.), filtered through a short pad of SiO$_2$ and the filtrate was concentrated by rotary evaporation. Purification by automated flash chromatography (5→50% EtOAc/hexanes) afforded cis-fused bicyclic γ-lactone (+)-15a (182 mg, 90% yield, 94% ee).

(+)-15a: white crystalline solid; TLC (EtOAc/hexanes, 1:4 v/v), R$_f$=0.45; [α]$_D^{19.9}$=+52.18 (c=0.77, CHCl$_3$); Enantiomeric excess was determined by chiral HPLC analysis in comparison with authentic racemic material using a Chiralcel OD-H column: hexanes: $^i$PrOH=95:05, flow rate 0.5 mL/min, λ=210 nm: t$_{minor}$=13.5 min, t$_{major}$=15.0 min, 94% ee; Absolute stereochemistry was assigned by analogy to bicyclic γ-lactone (+)-3c'; all spectral data matched that reported for cis-fused bicyclic γ-lactone (−)-15a.

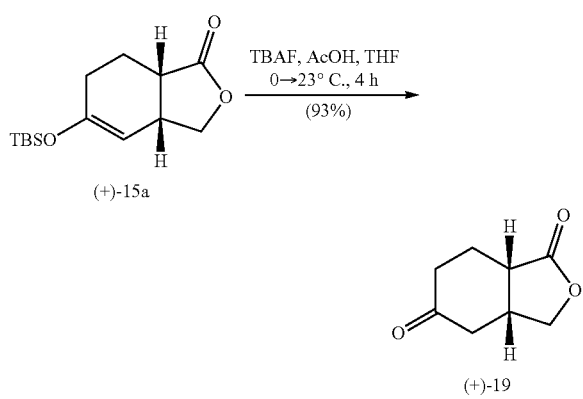

(3aR,7aS)-tetrahydroisobenzofuran-1,5(3H,4H)-dione ((+)-19): To a pre-cooled solution (0° C.) of bicyclic γ-lactone (+)-15a (72 mg, 0.268 mmol, 1.0 equiv) and glacial AcOH (31 μL, 0.536 mmol, 2.0 equiv) in anhydrous THF (2.7 mL, 0.1 M) was added TBAF (1.0 M in THF, 0.54 mL, 0.536 mmol, 2.0 equiv) dropwise. The reaction mixture was allowed to slowly warm to ambient temperature (23° C.) over 4 h, and then concentrated under reduced pressure. Purification by automated flash chromatography (5→80% EtOAc/hexanes) afforded ketolactone (+)-19 (38 mg, 93% yield).

(+)-19: clear colorless oil; TLC (EtOAc/hexanes, 1:1 v/v), $R_f$=0.23; $[α]_D^{20.0}$=+24.35 (c=0.11. CHCl$_3$); Absolute stereochemistry was assigned by analogy to bicyclic γ-lactone (+)-3c'; all spectral data matched that reported for ketolactone (+)-19.

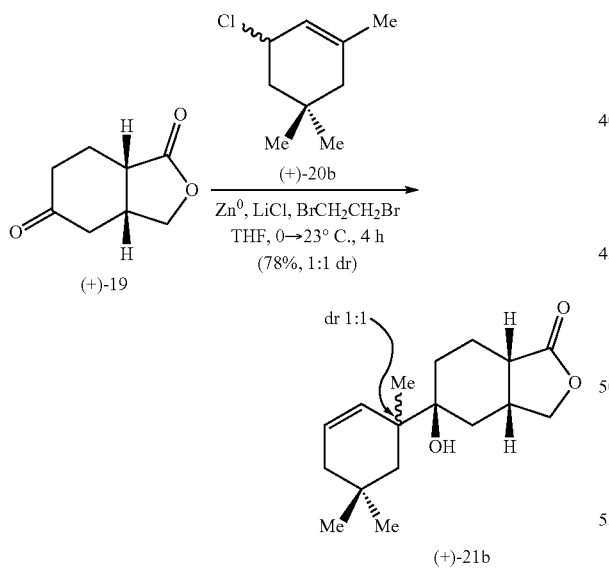

(3aR,5S,7aS)-5-hydroxy-5-(1,5,5-trimethylcyclohex-2-en-1-yl)hexahydroisobenzo-furan-1(3H)-one ((+)-21b): To an oven-dried round-bottomed flask was added zinc powder (766 mg, 11.6 mmol, 25 equiv) and LiCl (100 mg, 2.33 mmol, 5.0 equiv) with a large bore vacuum adapter with Teflon lined seal for addition of liquids via syringe. The flask and solids were then carefully flame-dried under high vacuum (using a vacuum/N$_2$ double manifold) by repeated heating and cooling cycles with swirling of the solids to avoid the solids from clumping. After the final cycle of heating, the solids were allowed to cool for 3 min under N$_2$, and then anhydrous THF (6.7 mL) was slowly and carefully added with vigorous stirring. After addition of THF, 1,2-dibromoethane (40 μL, 0.46 mmol, 1.0 equiv) was added which sometimes led to an exotherm simultaneous with rapid gas evolution, which needs to be controlled. Pressure fluctuations generated upon addition of 1,2-dibromoethane were controlled by momentarily switching the manifold from N$_2$ to vacuum. [Note: If gas evolution was not observed upon addition of 1,2-dibromoethane, a heat gun was employed to initiate gas evolution]. The solution was allowed to cool at ambient temperature over ~5 min before being further cooled to 0° C. A solution of ketolactone (+)-19 (71 mg, 0.46 mmol, 1.0 equiv) in THF (0.33 mL) was added dropwise by syringe followed by slow addition of allyl chloride(±)-20b (740 mg, 4.6 mmol, 10 equiv) in THF (1.3 mL) via syringe pump at a rate of 1.0 mL/h. During this time, the reaction mixture was allowed slowly warm to ambient temperature (23° C.). The reaction mixture was then quenched with saturated NH$_4$Cl solution (30 mL). The organic phase was separated and the aqueous phase was further extracted with EtOAc (3×30 mL). The organic layers were combined, washed with brine (10 mL), dried with MgSO$_4$, and concentrated under reduced pressure. Purification by automated flash chromatography (5→60% EtOAc/hexanes) afforded dimethyl cyclohexenol lactone (+)-21b (98 mg, 78% yield) as an inseparable mixture of two diastereomers (1:1 dr, based on $^1$H-NMR analysis of the crude mixture).

(+)-21b: white crystalline solid; TLC (EtOAc/hexanes, 1:1 v/v), $R_f$=0.44; $[α]_D^{19.8}$=+31.44 (c=0.23, CHCl$_3$); Absolute stereochemistry was assigned by analogy to dimethyl cyclohexenol lactone (−)-21b; All spectral data matched that reported for dimethyl cyclohexenol lactone (−)-21b.

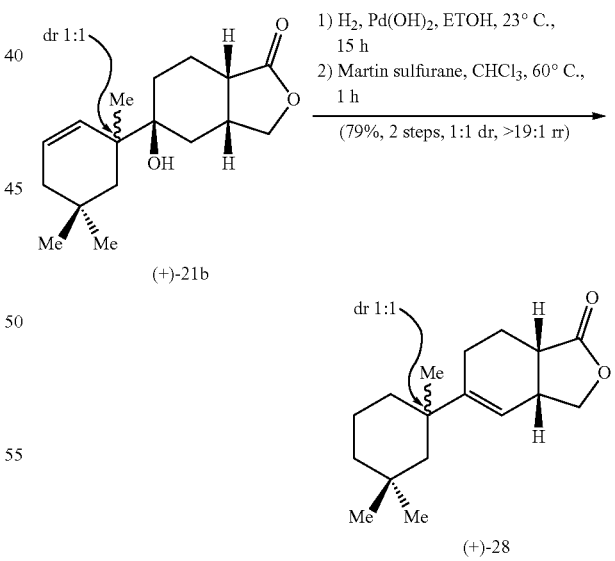

(3aR,7aS)-5-(1,3,3-trimethylcyclohexyl)-3a,6,7,7a-tetrahydroisobenzofuran-1(3H)-one ((+)-28): To a solution of dimethyl cyclohexenol lactone (+)-21b (93 mg, 0.33 mmol, 1.0 equiv) in absolute EtOH (6.6 mL) and under an atmosphere of N$_2$ was added Pd(OH)$_2$ on carbon (94 mg, 20 wt %, 0.67 mmol, 2.0 equiv). A H$_2$ balloon was attached to the flask and after three consecutive cycles of evacuation (under high vacuum) and H₂ purge, the mixture was stirred for 15 h. An aliquot was removed for ¹H-NMR analysis to ensure complete hydrogenation of the cyclohexene moiety. The reaction mixture was filtered through a pad of Celite, washed with EtOAc, concentrated under reduced pressure, and taken on directly to the next step without purification.

A glass tube was charged with the above crude alcohol (89 mg, 0.33 mmol, 1.0 equiv) in anhydrous CHCl₃ (11.6 mL, 0.02 M) and Martin Sulfurane dehydrating agent (478 mg, 0.67 mmol, 2.0 equiv). The tube was sealed and placed in a 60° C. oil bath for 1 h. The reaction mixture was cooled to ambient temperature (23° C.), concentrated under reduced pressure and purified by automated flash chromatography (5→30% EtOAc/hexanes) to afford cyclohexene lactone (+)-28 (69 mg, 79% yield over 2 steps) as a single regioisomer (>19:1 rr, based on ¹H-NMR analysis of the crude mixture).

(+)-28: clear colorless oil; TLC (EtOAc/hexanes, 1:4 v/v), $R_f$=0.41; $[\alpha]_D^{20.3}$=+66.91 (c=0.17, CHCl₃); Absolute stereochemistry was assigned by analogy to cyclohexenol lactone (−)-21b; (NMR data is provided for two diastereomers) ¹H NMR (500 MHz, CDCl₃) δ 5.40 (s, 2H), 4.43-4.33 (m, 2H), 4.08-3.96 (m, 2H), 3.15-3.02 (m, 2H), 2.82-2.69 (m, 2H), 2.16-1.85 (m, 9H), 1.80-1.49 (m, 7H), 1.47-1.38 (m, 2H), 1.31-1.23 (m, 2H), 1.20-1.05 (m, 4H), 0.91 (s, 3H), 0.88 (s, 3H), 0.86 (s, 3H), 0.82 (s, 3H), 0.79 (s, 3H), 0.77 (s, 3H); ¹³C NMR (126 MHz, CDCl₃) δ 179.24, 179.19, 148.16, 148.03, 116.76, 116.67, 72.81, 72.79, 48.02, 47.72, 40.46, 40.37, 39.00, 38.95, 37.83, 37.82, 36.26, 36.23, 35.97, 35.93, 33.38, 33.18, 31.66, 31.64, 31.46, 31.39, 21.58, 21.57, 21.18, 20.98, 19.61, 19.46; IR (thin film): 2932, 2860, 1769 cm⁻¹; HRMS (ESI+) m/z calcd for $C_{17}H_{26}LiO_2$ [M+Li]⁺: 269.2093, found: 269.2107.

MeOH and saturated aqueous Rochelle's salt (2.6 mL). The dry-ice bath was removed and the mixture was allowed to slowly warm to ambient temperature (23° C.). Subsequently, the reaction mixture was filtered through a pad of Celite, extracted with CH₂Cl₂ (3×10 mL), washed with brine (10 mL), and concentrated under reduced pressure. The crude lactol was of sufficient purity (>95% as judged by ¹H-NMR) to be carried on directly to the next step.

To a solution of the above crude lactol in anhydrous pyridine (0.8 mL) was added DMAP (2.0 mg, 0.015 mmol, 0.2 equiv) and Ac₂O (36 µL, 0.38 mmol, 5.0 equiv). The reaction mixture was stirred at ambient temperature (23° C.) for 14 h, poured into saturated aqueous NaHCO₃ solution (10 mL), and the aqueous layer was extracted with CH₂Cl₂ (3×10 mL). The combined organic layer was washed with brine (10 mL), dried over MgSO₄, filtered, and concentrated under reduced pressure. Purification by automated flash chromatography (0→30% EtOAc/hexanes) afforded acetyl lactol (+)-29 (14 mg, 62% yield over 2 steps) as a clear colorless oil and as a single diastereomer (>19:1 dr, based on ¹H-NMR analysis of the crude mixture). TLC (EtOAc/hexanes, 1:4 v/v), $R_f$=0.51; $[\alpha]_D^{20.3}$=+50.91 (c=0.11, CHCl₃); IR (thin film): 2939, 2861, 1744 cm⁻¹; HRMS (ESI+) m/z calcd for $C_{19}H_{30}LiO_3$ [M+Li]⁺: 313.2355, found: 313.2367. Absolute stereochemistry was assigned by analogy to cyclohexenol lactone (−)-21b; The diastereomeric mixture was further separated by semi-preparative reverse-phase HPLC (100×21.20 mm, 5 µm; linear gradient, 5→95% CH₃CN/H₂O with 0.1% of NH₄HCO₃ over 20 min, 10 mL/min) to yield (+)-29a ($T_R$=5.7 min) and (+)-29b ($T_R$=6.8 min).

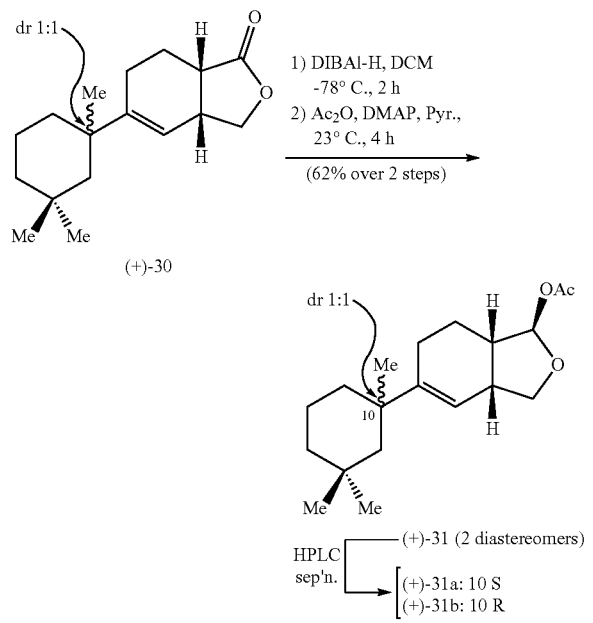

(+)-30

(+)-31 (2 diastereomers)
HPLC sep'n.
(+)-31a: 10 S
(+)-31b: 10 R (1R,3aR,7aS)-5-(1,3,3-trimethylcyclohexyl)-1,3,3a,6,7,7a-hexahydroisobenzofuran-1-yl acetate ((+)-29): To a solution of cyclohexene lactone (+)-28 (20 mg, 0.076 mmol, 1.0 equiv) in CH₂Cl₂ (1.3 mL, 0.06 M) was added DIBAl-H (1.0 M solution in CH₂Cl₂, 92 µL, 0.092 mmol, 1.2 equiv) dropwise at −78° C. The reaction mixture was stirred at −78° C. for 4 h and carefully quenched in sequence with 92 µL

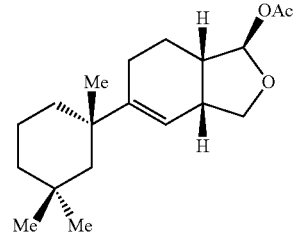

(+)-29a: ¹H NMR (500 MHz, CDCl₃) δ 6.03 (s, 1H), 5.46 (dd, J=4.6, 1.9 Hz, 1H), 4.27 (t, J=8.2 Hz, 1H), 3.70 (t, J=7.6 Hz, 1H), 2.96 (p, J=7.3 Hz, 1H), 2.35-2.27 (m, 1H), 2.19-2.12 (m, 1H), 2.06 (s, 3H), 1.99-1.90 (m, 1H), 1.80 (dt, J=12.9, 4.7 Hz, 1H), 1.73-1.67 (m, 1H), 1.66-1.24 (m, 5H), 1.21-1.07 (m, 1H), 1.03 (d, J=14.0 Hz, 1H), 0.92 (s, 3H), 0.87 (s, 3H), 0.82 (s, 3H); ¹³C NMR (126 MHz, CDCl₃) δ 170.48, 145.36, 117.37, 103.60, 74.63, 47.76, 40.20, 38.75, 37.58, 36.00, 35.72, 33.13, 31.38, 31.20, 26.77, 25.97, 21.33, 20.93, 19.36.

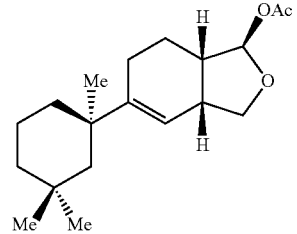

(+)-29b: $^1$H NMR (500 MHz, CDCl$_3$) δ 6.01 (s, 1H), 5.43 (dd, J=4.5, 2.0 Hz, 1H), 4.26 (t, J=8.3 Hz, 1H), 3.61 (t, J=7.9 Hz, 1H), 2.98 (dt, J=13.4, 7.3 Hz, 1H), 2.26 (td, J=7.4, 3.7 Hz, 1H), 2.09 (dt, J=16.9, 4.5 Hz, 1H), 2.05 (s, 3H), 2.01-1.79 (m, 2H), 1.67-1.52 (m, 2H), 1.46-1.23 (m, 4H), 1.18-1.06 (m, 2H), 0.99 (d, J=13.9 Hz, 1H), 0.91 (s, 3H), 0.86 (s, 3H), 0.84 (s, 3H); $^{13}$C NMR (126 MHz, CDCl$_3$) δ 170.51, 145.39, 117.40, 103.75, 74.65, 47.47, 40.12, 38.69, 37.57, 35.97, 35.68, 32.93, 31.38, 31.14, 26.76, 25.97, 21.32, 20.73, 19.21.

hexanes) afforded cyclohexene diacetate (+)-27b (37 mg, 99% yield over 2 steps) as a single diastereomer (>19:1 dr, based on $^1$H-NMR analysis of the crude mixture). (+)-27b: clear colorless oil; TLC (EtOAc/hexanes, 1:4 v/v), R$_f$=0.53; [α]$_D^{18.5}$=+31.52 (c=0.33, CHCl$_3$); Absolute stereochemistry was assigned by analogy to cyclohexenol lactone (−)-21b; $^1$H NMR (500 MHz, CDCl$_3$) δ 5.34 (dt, J=4.0, 1.6 Hz, 1H), 4.13-3.96 (m, 4H), 2.70-2.61 (m, 1H), 2.17-2.08 (m, 1H), 2.05 (s, 3H), 2.03 (s, 3H), 2.00-1.92 (m, 1H), 1.70-1.62 (m, 4H), 1.63-1.52 (m, 1H), 1.49-1.38 (m, 3H), 1.38-1.29 (m, 3H), 1.28-1.18 (m, 2H), 0.92 (s, 3H); $^{13}$C NMR (126 MHz, CDCl$_3$) δ 171.25, 171.15, 146.01, 118.56, 65.48, 65.11, 38.70, 36.59, 36.41, 36.30, 34.56, 26.47, 23.29, 23.02, 22.72, 21.13, 21.11; IR (thin film): 2930, 2856, 1742, 1235 cm$^{-1}$; HRMS (ESI+) m/z calcd for C$_{19}$H$_{31}$O$_4$ [M+H]$^+$: 323.2222, found: 323.2232.

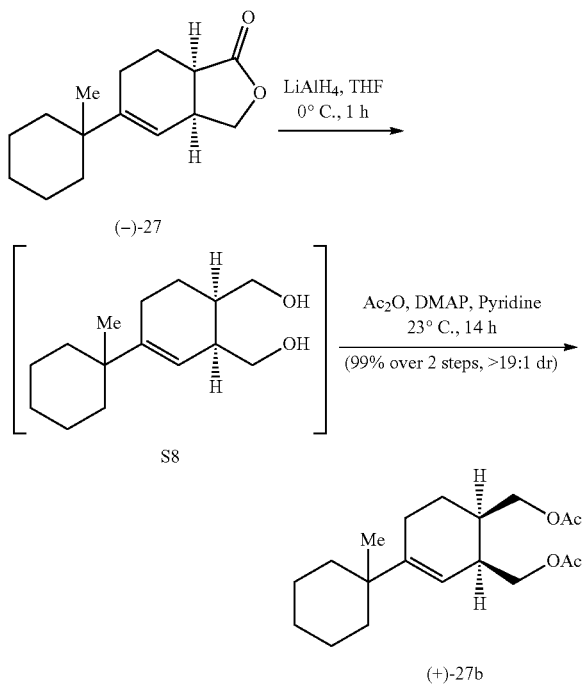

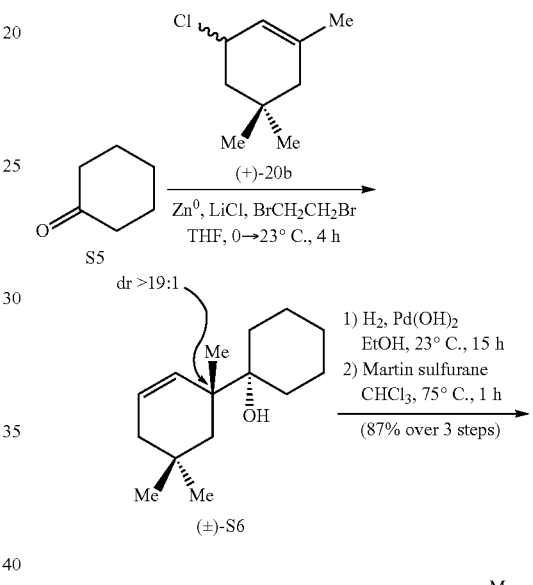

((3S,4R)-1'-methyl-[1,1'-bi(cyclohexan)]-1-ene-3,4-diyl) bis(methylene) diacetate (+)-S6: To a solution of the cyclohexene lactone (−)-26 (27 mg, 0.12 mmol, 1.0 equiv) in anhydrous THF (1.5 mL, 0.08 M) was added LiAlH$_4$ (2.0 M solution in THF, 0.15 mL, 0.30 mmol, 2.5 equiv) dropwise at 0° C. After stirring for 1 h, the ice bath was removed and the mixture was allowed to warm slowly to ambient temperature (23° C.) over 30 min. Upon consumption of starting material (as judged by TLC), the reaction mixture was cooled to 0° C. and carefully quenched in sequence with 12 μL H$_2$O, 12 μL 25% aqueous NaOH, and 30 μL H$_2$O. The ice bath was removed and the mixture was allowed to warm slowly to ambient temperature (23° C.). Subsequently, anhydrous MgSO$_4$ was added and the reaction mixture was vigorously stirred for 30 min, filtered through a pad of Celite and concentrated by rotary evaporation. The crude diol was of sufficient purity (>95% as judged by $^1$H-NMR) to be carried on directly to the next step.

To a solution of the above crude diol in anhydrous pyridine (1.0 mL, 0.1 M) was added DMAP (2.0 mg, 0.012 mmol, 0.1 equiv) and Ac$_2$O (120 μL, 1.28 mmol, 10.0 equiv). The reaction mixture was stirred at ambient temperature (23° C.) for 24 h, poured into saturated aqueous NaHCO$_3$ solution (10 mL), and the aqueous layer was extracted with CH$_2$Cl$_2$ (3×10 mL). The combined organic layer was washed with brine (10 mL), dried over MgSO$_4$, filtered, and concentrated under reduced pressure. Purification by automated flash chromatography (0→30% EtOAc/

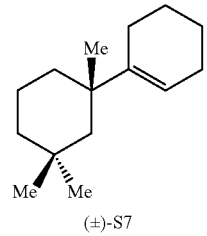

1',3',3'-trimethyl-[1,1'-bi(cyclohexan)]-1-ene ((±)-S7): To an oven-dried round-bottomed flask was added zinc powder (3.5 g, 53.5 mmol, 25 equiv) and LiCl (900 mg, 21.4 mmol, 10.0 equiv) with a large bore vacuum adapter with Teflon lined seal for addition of liquids via syringe. The flask and solids were then carefully flame-dried under high vacuum (using a vacuum/N$_2$ double manifold) by repeated heating and cooling cycles with swirling of the solids to avoid the solids from clumping. After the final cycle of heating, the solids were allowed to cool for 3 min under N$_2$, and then anhydrous THF (40.0 mL, 0.05 M) was slowly and carefully added with vigorous stirring. After addition of THF, 1,2-dibromoethane (0.4 mL, 4.28 mmol, 2.0 equiv) was added which sometimes led to an exotherm simultaneous with rapid gas evolution, which needs to be controlled. Pressure fluctuations generated upon addition of 1,2-dibromoethane were controlled by momentarily switching the manifold from N$_2$ to vacuum. [Note: If gas evolution was not observed upon addition of 1,2-dibromoethane, a heat gun was employed to initiate gas evolution]. The solution was allowed to cool at ambient temperature over ~5 min before being further cooled to 0° C. A solution of cyclohexanone S5 (0.22 mL, 2.14 mmol, 1.0 equiv) in THF (1.0 mL) was added dropwise by syringe followed by slow addition of allyl chloride (±)-20b (1.7 g, 10.7 mmol, 5.0 equiv) in THF (2.4 mL) via syringe pump at a rate of 1.0 mL/h. During this time, the reaction mixture was allowed to slowly warm to ambient temperature (23° C.). The reaction mixture was then quenched with saturated NH$_4$Cl solution (60 mL). The organic phase was separated and the aqueous phase was further extracted with EtOAc (3×60 mL). The organic layers were combined, washed with brine (20 mL), dried with MgSO$_4$, and concentrated under reduced pressure to afford dimethyl cyclohexenol (±)-S6 as a single diastereomer (>19:1 dr, based on H-NMR analysis of the crude mixture). This material was of sufficient purity (>95% as judged by $^1$H-NMR) to be carried directly to the next step without purification.

To a solution of (±)-S6 (600 mg, 2.7 mmol, 1.0 equiv) in absolute EtOH (55.0 mL, 0.05M) and under an atmosphere of N$_2$ was added Pd(OH)$_2$ on carbon (758 mg, 20 wt %, 5.4 mmol, 2.0 equiv). A H$_2$ balloon was attached to the flask and after three consecutive cycles of evacuation (under high vacuum) and H$_2$ purge, the mixture was stirred for 15 h. An aliquot was removed for H-NMR analysis to ensure complete hydrogenation of the cyclohexene moiety. The reaction mixture was filtered through a pad of Celite, washed with EtOAc, concentrated under reduced pressure, and taken on directly to the next step without purification.

A glass tube was charged with the above crude alcohol (45 mg, 0.20 mmol, 1.0 equiv) in anhydrous CHCl$_3$ (5.0 mL, 0.04 M) and Martin Sulfurane dehydrating agent (202 mg, 0.30 mmol, 1.5 equiv). The tube was sealed and placed in a 60° C. oil bath for 1 h. The reaction mixture was cooled to ambient temperature (23° C.), concentrated under reduced pressure and purified by automated flash chromatography using isocratic elution with HPLC grade n-hexane to afford cyclohexene (±)-S7 (41 mg, 87% yield over 3 steps).

(±)-S7: clear colorless oil; TLC (Hexanes), R$_f$=0.94; $^1$H NMR (500 MHz, CDCl$_3$) δ 5.47 (dt, J=3.7, 2.3 Hz, 1H), 2.10-1.86 (m, 5H), 1.69-1.49 (m, 6H), 1.44-1.37 (m, 1H), 1.33-1.22 (m, 1H), 1.18-1.04 (m, 2H), 0.98 (d, J=13.9 Hz, 1H), 0.92 (s, 3H), 0.87 (s, 3H), 0.86 (s, 3H); $^{13}$C NMR (126 MHz, CDCl$_3$) δ 143.86, 118.08, 48.11, 40.82, 38.71, 36.60, 33.32, 31.82, 31.60, 27.07, 25.92, 24.92, 23.74, 22.79, 19.76; IR (thin film): 2978, 2951, 2866 cm$^{-1}$; A satisfactory high-resolution mass spectrum of the parent ion could not be obtained for this compound.

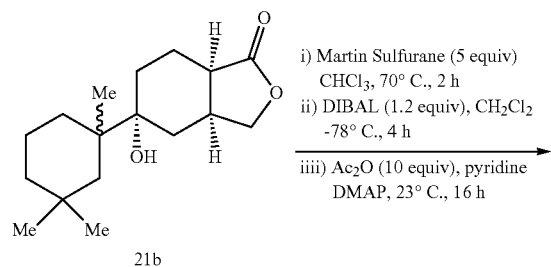

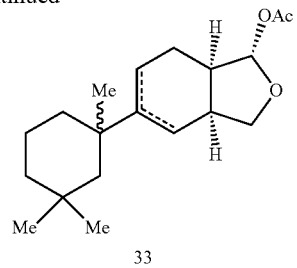

5-(1,3,3-Trimethylcyclohexyl)hexahydroisobenzofuran-1-yl acetate (33): Martin sulfurane (1.20 g, 1.78 mmol, 5.00 equiv) was weighed out to a flame dried RB flask in a N$_2$ filled glovebox. The flask was sealed with a septum and removed from the glovebox. A solution of the crude alcohol 21b (100 mg, 1.78 mmol, 1.00 equiv) in dry CHCl$_3$ (7.00 mL) was added to the reaction flask and the resulting mixture heated to 70° C. for 2 hours. After complete reaction, the mixture was concentrated, filtered through a short pad of silica (30% EtOAc:Hexanes), concentrated, and used crude in the next step.

The lactone (20 mg of crude) was taken up in CH$_2$Cl$_2$ (1.3 mL) and cooled to −78° C. DIBAL (16.0 mL, 91.0 mmol, 1.20 equiv) was added dropwise at this temperature and the reaction stirred for 4 hours. Upon completion, the mixture was successively quenched with H$_2$O (4 mL), NaOH (15% aqueous, 4 mL) and H$_2$O (10 mL). The mixture was stirred for 30 minutes then a spatula tip of MgSO$_4$ was added and stirred for an additional 30 minutes. The resulting heterogeneous mixture was filtered through Celite and concentrated. Material was used without further purification.

The crude lactol was dissolved in pyridine (1.00 mL) and DMAP (1.00 mg, 8.00 mmol, 0.10 equiv) was added. Ac$_2$O (71.8 mL, 0.76 mmol, 10.0 equiv) was added dropwise and the reaction allowed to stir overnight at room temperature. The mixture was quenched with NaHCO$_3$ (sat. aqueous) and extracted with CH$_2$C$_2$. The combined organics were washed with brine, dried over MgSO4, filtered, and concentrated. Purification of the resulting residue by silica gel chromatography (10-40% Et$_2$O:Hexanes) provided 23.4 mg (28% yield, 5 steps) of the title compound 33 as a mixture of diastereomers as a clear colorless oil. Due to spectral complexity, integrations are not corrected and are listed for all diastereomers. R$_f$=0.51 (20% EtOAc:Hexanes). IR (film) 2945 (s) 2864 (m), 2361 (w), 1745 (s), 1462 (w), 1364 (m), 1236 (s), 1103 (m), 1007 (m), 964 (m), 930 (m), 905 (m) cm 1. $^1$H NMR (600 MHz, CDCl$_3$) δ 6.01 (s, 2H), 5.46-5.41 (m, 2H), 4.26 (td, J=8.3, 2.1 Hz, 2H), 3.68 (t, J=7.6 Hz, 1H), 3.61 (t, J=7.9 Hz, 1H), 3.01-2.91 (m, 2H), 2.34-2.22 (m, 3H), 2.17-2.02 (m, 10H), 2.00-1.87 (m, 6H), 1.87-1.74 (m, 3H), 1.72-1.53 (m, 10H), 1.53-1.24 (m, 5H), 1.18-1.07 (m, 8H), 1.05-0.97 (m, 7H), 0.91 (d, J=1.7 Hz, 3H), 0.86 (d, J=1.6 Hz, 3H), 0.84 (s, 2H), 0.81 (s, 2H). $^{13}$C NMR (150 MHz, CDCl$_3$) δ 170.79, 170.77, 146.0, 116.5, 116.4, 104.0, 103.9, 75.0, 74.4, 48.5, 47.7, 43.23, 43.17, 40.6, 40.5, 38.83, 38.82, 36.8, 36.5, 36.3, 33.4, 31.6, 31.5, 23.8, 23.1, 22.64, 22.62, 21.6, 19.7, 19.5. HRMS (ESI): Calcd for C$_{19}$H$_{30}$O$_3$Na$_1$ [M+Na]$^+$: 329.2087, Found: 329.2093.

43

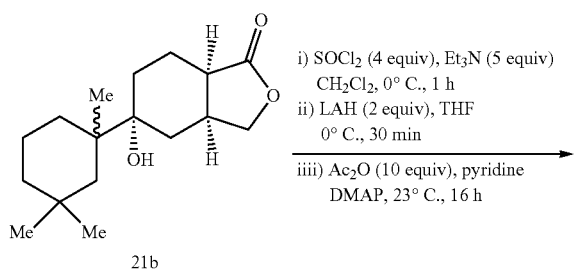

21b

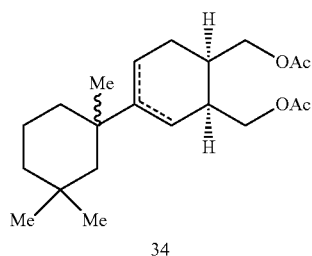

34

Compound 34: The tertiary alcohol 21b (76.0 mg, 0.27 mmol, 1.00 equiv) was added to a flame dried reaction flask and dissolved in $CH_2Cl_2$ (1.00 mL). The resulting solution was cooled to 0° C. and $Et_3N$ (190 mL, 1.36 mmol, 5.00 equiv) was added. $SOCl_2$ (78.9 mL, 1.08 mmol, 4.00 equiv) was added dropwise and the reaction was stirred for 1 hour at 0° C. Upon complete reaction, as judged by TLC, the mixture was concentrated. The residue was taken up in 30% $Et_2O$:Hexanes and passed through a short pad of silica (30% $Et_2O$:Hexanes) and concentrated. The resulting yellow oil was used in the next step without further purification.

The residue (20.4 mg, 78.0 mmol, 1.00 equiv) was taken up in THF (1.00 mL) and cooled to 0° C. LAH (2 M in THF, 78.0 mL, 156 mmol) was added and the reaction stirred for 30 minutes at 0° C. The mixture was sequentially quenched with 6 mL $H_2O$, 6 mL NaOH (15% aqueous), and 18 mL $H_2O$ then stirred for 30 minutes while warming to r.t. A spatula tip of $MgSO_4$ was added and the mixture stirred an additional 30 minutes. The heterogeneous mixture was filtered through Celite, concentrated, and used in the next step without purification.

The crude diol was dissolved in pyridine (1.00 mL) and DMAP (1.00 mg, 7.80 mmol, 0.10 equiv) was added. $Ac_2O$ (74.0 mL, 0.78 mmol, 10.0 equiv) was added and the reaction stirred overnight at r.t. The mixture was then quenched with $NaHCO_3$ (sat. aqueous) and extracted with $CH_2Cl_2$ (3×1 mL). The combined organics were washed with brine, dried, filtered and concentrated. Purification by silica gel chromatography provided 16.3 mg (27% yield, 3 steps) of the bisacetate 34 as a mixture of four isomers. Rf=0.49 (30% $Et_2O$:Hexanes, PAA). IR (film) 2947 (m), 2919 (m), 2865 (m), 1740 (s), 1462 (w), 1451 (w), 1366 (m), 1230 (s), 1034 (m). $^1H$ NMR (400 MHz, $CDCl_3$) δ 5.53-5.33 (m, 1H), 4.15-3.91 (m, 4H), 2.74-2.48 (m, 1H), 2.30-2.09 (m, 2H), 2.05 (s, 3H), 2.03 (s, 3H), 1.99-1.76 (m, 1H), 1.74-1.60 (m, 1H), 1.60-1.48 (m, 2H), 1.48-1.35 (m, 1H), 1.28 (m, 1H), 1.18-1.05 (m, 2H), 1.05-0.95 (m, 1H), 0.95-0.71 (m, 9H). HRMS (ESI): Calcd for $C_{21}H_{34}O_4Na_1$ $[M+Na]^+$: 373.2349, Found: 373.2344.

Example B

Methods for Synthesizing Gracilin Cores

In this example, methods for synthesizing gracilin cores and representative gracilin derivatives of the invention are described.

44

Synthesis of Starting Materials

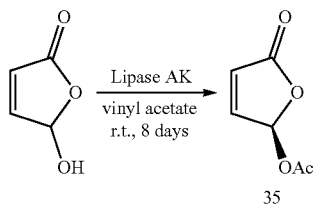 [SMILES: O=C1C=CC(O)O1 ; CC(=O)O[C@H]1C=CC(=O)O1]

35

(R)-5-oxo-2,5-dihydrofuran-2-yl acetate (35): Synthesized according to known literature procedure (Tao, D. J.; Slutskyy, Y.; Overman, L. E. *J. Am. Chem. Soc.* 2016, 138, 2186). 5-Hydroxyfuran-2(5H)-one (Moradei, O. M. and Paquette, L. A. *Org. Synth.* 2003, 80, 66) (7.97 g, 89.9 mmol) was added to a flame dried reaction flask under $N_2$ and suspended in vinyl acetate (82.0 mL). Lipase AK (5.50 g) was added and the reaction mixture stirred for 8 days at room temperature. Upon complete reaction, the mixture was filtered through Celite and the filtrate concentrated. The residue was purified by silica gel chromatography to yield 10.9 grams (96% yield, 93:7 er) of the title compound as a pale yellow liquid. Spectroscopic data was in agreement with previously reported data. The enantiomeric purity was determined by HPLC analysis using a chiral column (Chiralpak AD-H column, 22° C., 1.0 mL/min, 90:10 Hexanes: Isopropanol, 254 nm, $t_{minor}$=12.273 min, $t_{major}$=13.853 min).

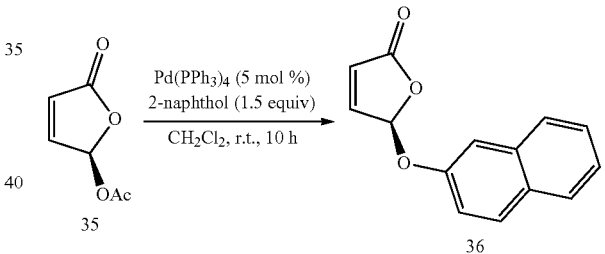

(R)-5-(naphthalen-2-yloxy)furan-2(5H)-one (36): Procedure was adapted from known literature procedure (Tao, D. J.; Slutskyy, Y.; Overman, L. E. *J. Am. Chem. Soc.* 2016, 138, 2186). $Pd(PPh_3)_4$ (3.23 g, 2.79 mmol, 0.05 equiv) was weighed out to a flamed dried round bottom flask in an $N_2$ filled glovebox. The flask was capped with a septum and removed from the glovebox. The yellow solid was dissolved in $CH_2Cl_2$ (475 mL) at room temperature. 2-naphthol (12.1 g, 83.8 mmol, 1.50 equiv) was added to the reaction flask followed by (R)-5-oxo-2,5-dihydrofuran-2-yl acetate 35 (7.94 g, 55.9 mmol, 1.00 equiv). The resulting solution was allowed to stir for 10 hours at room temperature over which time the reaction underwent several color changes from yellow to orange, and finally dark garnet. The reaction mixture was concentrated and purified directly by silica gel chromatography (10-100% EtOAc:Hexanes) to yield the 7.58 grams (60% yield, 94:6 er) of the title compound as a white solid. This material could be recrystallized from $CH_2Cl_2$:Hexanes to a single enantiomer if desired. Spectroscopic data was in agreement with previously reported data. $^1H$ NMR (600 MHz, $CDCl_3$) δ 7.83 (app t, J=9.0 Hz, 3H), 7.59 (d, J=1.9 Hz, 1H), 7.52 (t, J=7.5 Hz, 1H), 7.49-7.41 (m, 2H), 7.28 (dd, J=8.7, 2.3 Hz, 1H), 6.56 (s, 1H), 6.39 (d, J=5.7 Hz, 1H). $^{13}$C NMR (150 MHz, CDCl$_3$) δ 170.1, 154.3, 149.9, 134.2, 130.5, 130.1, 127.9, 127.5, 126.9, 125.5, 125.1, 118.7, 111.8, 100.9. The enantiomeric purity was established by HPLC analysis using a chiral column (Chiralpak AD-H, 22° C., 1.0 mL/min, 90:10 Hexanes:Isopropanol, 254 nm, $t_{major}$=11.292 min, $t_{minor}$=15.236 min).

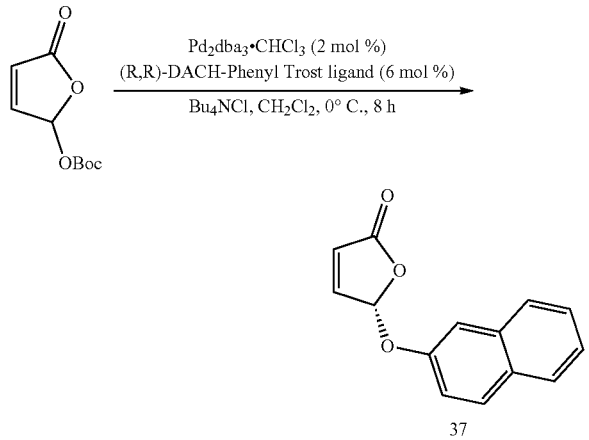

37

(S)-5-(naphthalen-2-yloxy)furan-2(5H)-one (37): Synthesized according to known literature procedure (Trost, B. M. and Toste, F. D. *J. Am. Chem. Soc.* 2003, 125, 3090). The spectroscopic data was in agreement with the R-enantiomer prepared above. The enantiopurity was established by HPLC analysis using a chiral column (Chiralpak AD-H, 22° C., 1.0 mL/min, 90:10 Hexanes:Isopropanol, 254 nm, $t_{minor}$=11.648 min, $t_{major}$=15.663 min).

Diels-Alder Cycloaddition Optimization

General procedure for Diels-Alder cycloaddition optimization: The desired lactone (0.25 mmol, 1.00 equiv) was added to a flame dried one-dram scintillation vial under an atmosphere of dry N$_2$. Toluene (1.00 mL) was added to the reaction vessel followed by 2-trimethylsiloxy-1,3-butadiene (equiv as stated in table below). The scintillation vial was sealed with a screw cap and heated to 100° C. for 16 h.

Upon cooling to 23° C., the solvent was removed under reduced pressure and the resulting residue taken up in THF (575 ml). HCl (575 ml, 1 M, aqueous) was added and the biphasic mixture stirred vigorously for 30 minutes. At the completion of the reaction, the phases were separated and the aqueous layer extracted with EtOAc (3×1 mL). The combined extracts were washed with brine, dried over MgSO$_4$, filtered, and concentrated. 1,3,5-Trimethoxybenzene was added as an internal standard to determine the yield of each reaction.

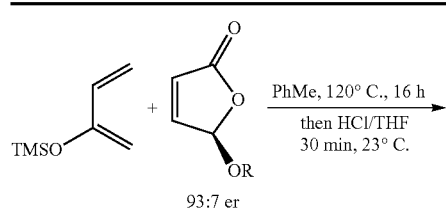

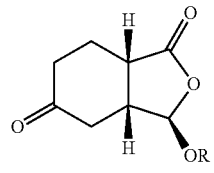

R = 2-naphthyl, 40

| Entry | R | Diene (equiv) | rr$^a$ | yield (NMR) | es$^b$ |
|---|---|---|---|---|---|
| 1 | Me | 1.2 | 1.2:1 | 37% | ND |
| 2 | $^i$Pr | 1.2 | 1.3:1 | 31% | ND |
| 3 | Ac | 1.2 | 1.6:1 | 54% | 87% |
| 4 | 2-naphthyl | 1.2 | 6:1 | 47% | 99% |
| 5 | 2-naphthyl | 2.0 | 7:1 | 61% | 99% |
| 6 | 2-naphthyl | 2.5 | 9:1 | 83% | 99% |
| 7* | 2-naphthyl | 2.5 | >20:1 | 53% | >99% |

$^a$Regioisomeric ratio (rr) determined by $^1$H NMR analysis of the crude reaction mixture with a calibrated internal standard.
$^b$Enantiospecificity determined by HPLC analysis with a chiral column.
*Results reported are after recrystallization.

Alternative Synthetic Route

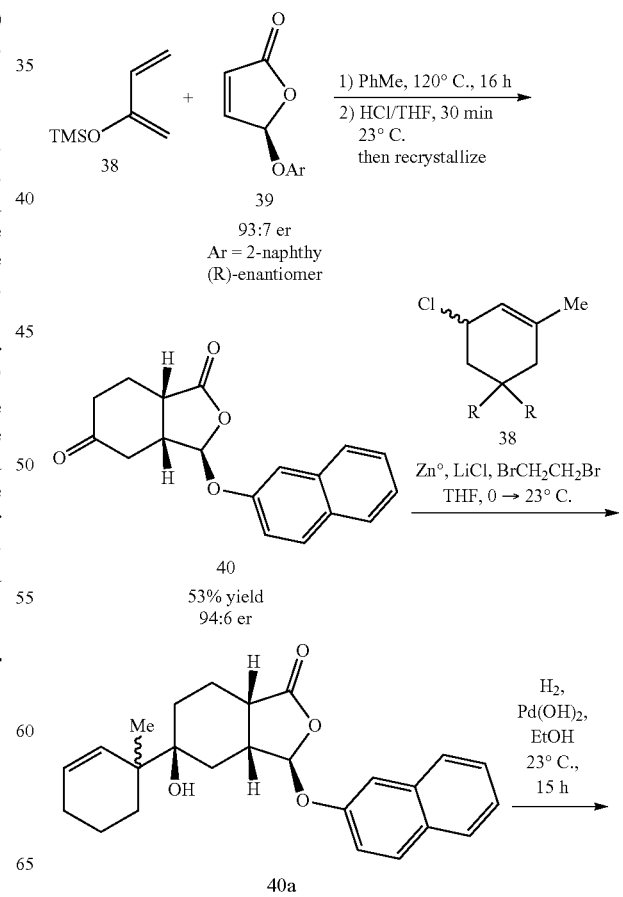

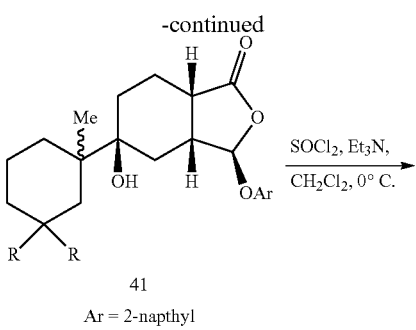

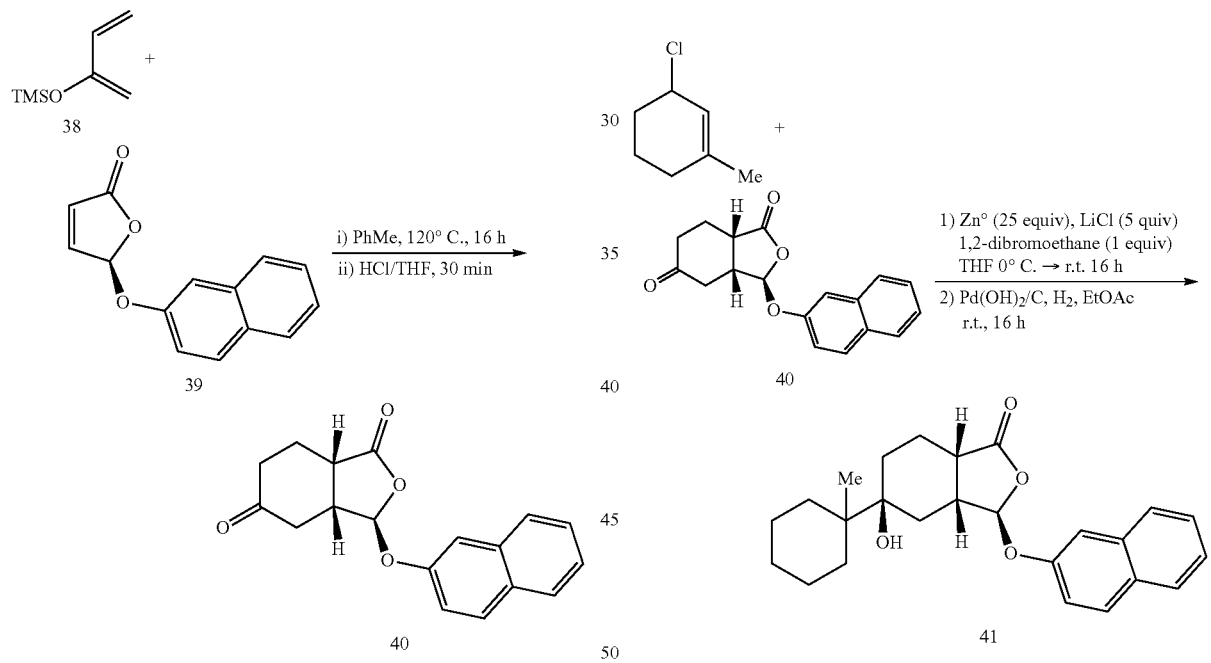

over MgSO$_4$, filtered, and concentrated. To crude compound as a 9:1 mixture of regioisomers. Purification by silica gel chromatography (10-60% EtOAc:Hexanes) followed by recrystallization yielded 1.35 grams (42% yield, 94:6 er) of the title compound as a white solid. Rf=0.23 (60% Et$_2$O: Hexanes). M.P.=143-145° C. IR (film) 3430 (w), 3060 (m), 2960 (m), 2253 (w), 1788 (s), 1716 (s), 1632 (m), 1600 (m), 1511 (m), 1468 (m), 1391 (m), 1366 (m), 1347 (m), 1252 (s), 1157 (s), 1122 (s), 1074 (m) cm$^{-1}$. $^1$H NMR (600 MHz, CDCl$_3$) δ 7.80 (app d, J=8.8 Hz, 2H), 7.77 (d, J=8.2 Hz, 1H), 7.48 (t, J=7.5 Hz, 1H), 7.45-7.39 (m, 2H), 7.18 (dd, J=8.9, 2.5 Hz, 1H), 5.85 (s, 1H), 3.42-3.36 (m, 1H), 3.28-3.21 (m, 1H), 2.73 (dd, J=15.3, 6.7 Hz, 1H), 2.48-2.36 (m, 4H), 2.33-2.24 (m, 1H). $^{13}$C NMR (150 MHz, CDCl$_3$) δ 207.9, 176.5, 153.7, 134.2, 130.3, 130.1, 127.8, 127.5, 127.0, 125.1, 118.6, 111.2, 103.7, 42.2, 39.6, 37.4, 36.8, 22.4. HRMS (ESI): Calcd for C18H16O4Na$_1$ [M+Na]$^+$: 319.0941, Found: 319.0942. Optical Rotation: [α]$_D^{25}$-201.6 (c=1.00, CHCl3) for an enantiomerically enriched sample of 94:6 er. The enantiomeric purity was established by HPLC analysis using a chiral column (Chiralpak AD-H column, 22° C., 1.0 mL/min, 90:10 Hexane:Isopropanol, 254 nm, t$_{minor}$=39.708 min, t$_{major}$=59.605 min). Absolute stereochemistry determined unambiguously via X-ray diffraction.

(3R,3aR,7aS)-3-(naphthalen-2-yloxy)tetrahydroisobenzofuran-1,5 (3H,4H)-dione (40): (R)-5-(naphthalen-2-yloxy)furan-2(5H)-one 36 (2.47 g, 10.9 mmol, 1.00 equiv) was added to aflame dried pressure vessel and the atmosphere purged with N$_2$. PhMe (8.67 mL) was added followed by 2-trimethylsiloxy-1,3-butadiene 38 (4.73 mL, 27.2 mmol, 2.50 equiv). The pressure vessel was sealed with a screw cap and the mixture heated to 120° C. overnight. Upon cooling, the solvent was removed under reduced pressure and the residue taken up in THF (25 mL). HCl (25 mL, 1 M aqueous) was added and the resulting mixture was stirred vigorously for 30 minutes. The mixture was then transferred to a separatory funnel and the phases separated. The aqueous phase was extracted with Et$_2$O (3×25 mL) and the combined extracts were washed first with NaHCO$_3$ (15 mL, sat. aqueous) then brine (20 mL). The organic phase was dried (3R,3aR,5S,7aS)-5-hydroxy-5-(1-methylcyclohexyl)-3-(naphthalen-2-yloxy)hexahydroisobenzofuran-1(3H)-one (41): Zn° powder (1.38 g, 21.1 mmol, 25.0 equiv) and LiCl (179 mg, 4.22 mmol, 5.00 equiv) were added to a flame dried RB flask and flame dried under high vacuum and cooled to room temperature for three cycles. Upon final cooling, THF (11.7 mL) was added and the resulting heterogeneous solution was stirred vigorously. 1,2-Dibromoethane (73.0 mL, 0.84 mmol, 1.00 equiv) was added and the solution was heated with a heat gun to initiate a gentle reflux. The solution was then cooled to 0° C. and the ketolactone 40 (250 mg, 0.84 mmol, 1.00 equiv) was added as a solution in THF (1.50 mL). 3-chloro-1-methylcyclohex-1-ene (Machacek, M. R.; Romeo, E. T.; Kattar, S. D.; Christopher, M.; Altman, M. D.; Northrup, A. B.; Ellis, J. M.; O'Boyle, B.; Donofrio, A.; Grimm, J.; Reutershan, M. H.; Childers, K.

K.; Otte, R. D.; Cash, B.; Ducharme, Y.; Haidle, A. M.; Spencer, K.; Vitharana, D.; Wu, L.; Zhang, L.; Zhang, P.; Beaulieu, C.; Guay, D. WO2014/48065 A1, Apr. 3, 2014) (990 mL, 7.59 mmol, 9.00 equiv) was added over 5 hours via syringe pump as a solution in THF (2.40 mL). The reaction was allowed to warm to r.t. over the course of the addition and stirred overnight. Upon complete reaction, the mixture was quenched with NH$_4$Cl (sat. aqueous) and extracted with EtOAc (3×10 mL). The combined extracts were washed with brine, dried over MgSO$_4$, filtered, and concentrated. Purification by silica gel chromatography (10-90% EtOAc:Hexanes) provided 152 mg (46% yield) of the homoallylic alcohol as an inseparable mixture of epimers. Additionally, 52.5 mg (21% recovery) of the starting material was isolated and could be resubjected to the reaction conditions. Rf=0.38 (30% EtOAc:Hex). IR (film) 3499 (br, w), 2933 (s), 2863 (m), 1784 (s), 1658 (w), 1631 (m), 1600 (m), 1512 (m), 1467 (m), 1443 (m), 1252 (m), 1213 (m), 1177 (m), 1139 (m), 1121 (m), 962 (w), 927 (w) cm 1. Due to spectral complexity, integrations are not corrected and are listed for both diastereomers.

$^1$H NMR (600 MHz, CDCl$_3$) δ 7.81-7.72 (m, 12H), 7.50-7.36 (m, 12H), 7.20-7.15 (m, 4H), 5.92-5.86 (m, 3H), 5.85 (s, 1H), 5.77 (d, J=5.1 Hz, 3H), 5.61-5.54 (m, 3H), 3.26 (t, J=6.4 Hz, 1H), 3.21-3.10 (m, 4H), 3.05 (app dtd, J=12.6, 6.5, 2.6 Hz, 3H), 2.54-2.47 (m, 1H), 2.40-2.34 (m, 1H), 2.28 (s, 1H), 2.21-1.62 (m, 36H), 1.40 (app dd, J=17.3, 12.9 Hz, 8H), 1.34-1.19 (m, 15H), 1.00 (d, J=4.0 Hz, 8H). $^{13}$C NMR (150 MHz, CDCl$_3$) δ 177.88, 177.81, 176.7, 154.21, 154.19, 154.0, 134.3, 130.9, 130.8, 130.2, 130.1, 130.0, 129.85, 129.8, 127.81, 127.79, 127.42, 127.39, 126.9, 126.76, 126.74, 124.9, 124.73, 124.72, 118.83, 118.79, 118.6, 111.0, 110.91, 110.88, 104.0, 103.9, 103.1, 81.0, 74.4, 74.3, 42.6, 42.5, 39.7, 39.5, 39.4, 36.72, 36.69, 36.2, 31.1, 30.5, 30.2, 30.04, 30.02, 29.9, 27.9, 27.6, 26.8, 25.2, 22.2, 22.0, 19.68, 19.66, 18.7, 18.24, 18.20. HRMS (ESI): Calcd for C$_{25}$H$_{28}$O$_4$Na$_1$ [M+Na]$^+$: 415.1880, Found: 415.1881.

The ketone prepared above was taken up in EtOAc (12.3 mL) and Pd(OH)$_2$/C (20% wt., 108 mg, 0.40 equiv) was added. The atmosphere was purged with an H$_2$ balloon and the mixture allowed to stir overnight at room temperature. Upon complete reduction, the mixture was filtered through Celite and concentrated. The resulting residue was purified by silica gel chromatography (30% EtOAc:Hex) to yield 84.5 mg (55% yield) of the title compound as a white solid. Rf=0.46 (30% EtOAc:Hexanes). M.P.=156-160° C. IR (film) 3516 (br, w) 2931 (s), 2860 (m), 1777 (s), 1631 (w), 1600 (w), 1512 (w), 1468 (w), 1445 (m) 1251 (m), 1214 (m), 1177 (m), 1140 (m), 1046 (m), 922 (s) cm. 1'H NMR (600 MHz, CDCl$_3$) δ 7.80-7.73 (m, 3H), 7.46 (ddd, J=8.1, 6.9, 1.0 Hz, 1H), 7.43 (d, J=2.3 Hz, 1H), 7.39 (ddd, J=8.0, 6.9, 1.0 Hz, 1H), 7.18 (dd, J=8.9, 2.5 Hz, 1H), 5.77 (s, 1H), 3.71 (app t, J=5.6 Hz, 1H), 3.18 (app t, J=6.4 Hz, 1H), 3.04 (app dt, J=12.8, 6.4 Hz, 1H), 2.19-2.14 (m, 1H), 2.12-2.03 (m, 2H), 1.72-1.64 (m, 4H), 1.62-1.56 (m, 2H), 1.48-1.23 (m, 6H), 0.94 (s, 3H). $^{13}$C NMR (150 MHz, CDCl$_3$) δ 177.8, 154.2, 134.3, 130.1, 129.9, 127.8, 127.4, 126.8, 124.7, 118.8, 110.9, 104.0, 75.1, 63.0, 40.2, 39.4, 36.7, 30.54, 30.45, 30.0, 29.9, 26.7, 26.3, 22.1, 18.3, 17.3. HRMS (ESI): Calcd for C$_{25}$H$_{30}$O$_4$Na$_1$ [M+Na]$^+$: 417.2036, Found: 417.2036. Absolute stereochemistry determined unambiguously via X-ray diffraction.

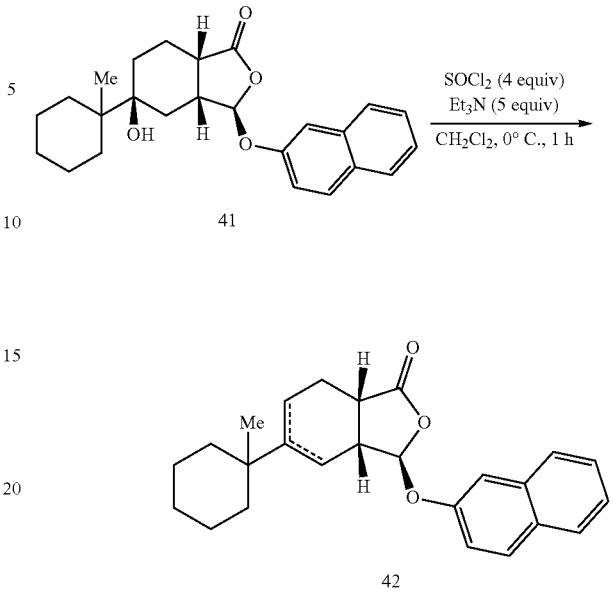

Mixture of (3R,3aR,7aS)-5-(1-methylcyclohexyl)-3-(naphthalen-2-yloxy)-3a,6,7,7a-tetrahydroisobenzofuran-1 (3H)-one and (3R,3aR,7aS)-5-(1-methylcyclohexyl)-3-(naphthalen-2-yloxy)-3a,4,7,7a-tetrahydroisobenzofuran-1 (3H)-one (42): The tertiary alcohol 41 (84.5 mg, 0.24 mmol, 1.00 equiv) was added to a flame dried reaction flask and dissolved in CH$_2$Cl$_2$ (1.00 mL). The resulting solution was cooled to 0° C. and Et$_3$N (150 mL, 1.07 mmol, 5.00 equiv) was added. SOCl$_2$ (62.5 mL, 0.86 mmol, 4.00 equiv) was added dropwise and the reaction was stirred for 1 hour at 0° C. Upon complete reaction, as judged by TLC, the mixture was concentrated and purified directly by silica gel chromatography (0-20% EtOAc:Hex) to provide 38.0 mg (47% yield) of the eliminated product as a pale yellow oil. Attempts to separate the product isomers were unsuccessful. Rf=0.65 (30% EtOAc:Hexanes). IR (film) 2928 (s), 2854 (m), 1787 (s), 1631 (w), 1600 (w), 1511 (w), 1467 (w), 1363 (w), 1251 (m), 1213 (m), 1178 (m), 1148 (m), 1120 (m), 972 (m), 947 (s), 845 (m) cm$^{-1}$. Due to spectral complexity, integrations are not corrected and are listed for all diastereomers. $^1$H NMR (600 MHz, CDCl$_3$) δ 7.82-7.74 (m, 10H), 7.49-7.43 (m, 7H), 7.39 (app ddt, J=8.2, 6.8, 1.4 Hz, 3H), 7.21 (app ddd, J=8.7, 6.1, 2.5 Hz, 3H), 7.10 (app ddd, J=23.7, 8.9, 5.5 Hz, 4H), 5.84 (s, 2H), 5.82 (s, 1H), 5.65 (t, J=4.5 Hz, 1H), 5.56-5.53 (m, 2H), 5.45 (dq, J=7.6, 3.1 Hz, 1H), 5.35 (s, 1H), 5.34-5.31 (m, 1H), 4.19-4.11 (m, 1H), 3.39-3.32 (m, 2H), 3.28-3.18 (m, 3H), 3.18-3.06 (m, 1H), 3.07-2.67 (m, 7H), 2.60 dddd, J=17.1, 4.8, 3.0, 1.7 Hz, 1H), 2.43 (dddt, J=17.1, 8.6, 4.1, 1.4 Hz, 1H), 2.34 (dd, J=15.9, 6.8 Hz, 1H), 2.30-2.22 (m, 2H), 2.19-1.82 (m, 13H), 1.82-1.51 (m, 19H), 1.51-1.17 (m, 39H), 0.97 (s, 9H). $^{13}$C NMR (150 MHz, CDCl$_3$) δ 178.7, 177.9, 154.1, 154.1, 134.2, 130.0, 129.73, 129.71, 127.66, 127.31, 127.28, 126.64, 126.62, 124.64, 124.61, 118.73, 118.69, 111.0, 110.9, 105.1, 104.4, 74.5, 74.3, 42.9, 40.8, 39.0, 38.4, 36.7, 36.6, 36.3, 35.96, 35.95, 35.9, 35.82, 35.80, 35.7, 26.4, 26.31, 26.29, 24.1, 23.1, 22.68, 22.67, 22.43, 22.36, 21.1, 20.4. HRMS (ESI): Calcd for C$_{25}$H$_{28}$O$_3$Na$_1$ [M+Na]$^+$: 399.1931, Found: 399.1934.

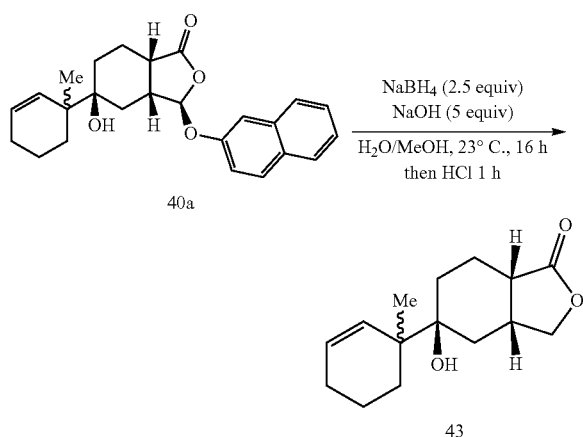

(3aR,5S,7aS)-5-hydroxy-5-(1-methylcyclohex-2-en-1-yl)hexahydroisobenzofuran-1(3H)-one (43): Procedure adapted from literature report (Trost, B. M.; Crawley, M. L. *Chem. Eur. J.* 2004, 10, 2237). NaBH$_4$ (9.80 mg, 0.26 mmol, 2.50 equiv) was added to a stirred solution of NaOH (20.4 mg, 0.51 mmol, 5.00 equiv) in H$_2$O (500 mL) under an air atmosphere. After stirring for 5 minutes at room temperature, the naphthyloxylactone 40a (40.3 mg, 0.1 mmol, 1.00 equiv) was added as a solution in MeOH (1.00 mL). The mixture was allowed to stir overnight at room temperature then quenched with HCl (conc. 100 mL) and stirred for 1 hour. The reaction was diluted with CH$_2$Cl$_2$ (2 mL) and H$_2$O (2 mL) and the layers separated. The organic phase was washed with brine, dried over MgSO$_4$, filtered, and concentrated. The crude residue was purified by silica gel chromatography (10-50% EtOAc:Hexanes) to obtain 4.6 mg (18% yield) of the title compound as an inseparable mixture of epimers. $^1$H NMR (600 MHz, CDCl$_3$) δ 5.87 (ddd, J=10.1, 5.3, 2.0 Hz, 1H), 5.59-5.53 (m, 1H), 4.28-4.23 (m, 1H), 3.94 (dd, J=8.9, 2.8 Hz, 1H), 2.78 (dq, J=11.1, 5.7, 5.2 Hz, 1H), 2.68-2.63 (m, 1H), 2.13-2.06 (m, 1H), 2.06-1.80 (m, 6H), 1.70 (ddd, J=14.7, 10.3, 3.6 Hz, 3H), 1.64-1.49 (m, 5H), 1.41-1.20 (m, 6H), 0.97 (d, J=4.8 Hz, 2H). $^{13}$C NMR (150 MHz, CDCl$_3$) δ 178.7, 178.61, 131.07, 131.02, 130.6, 74.88, 74.85, 72.1, 72.0, 42.6, 42.5, 39.1, 39.0, 33.33, 33.28, 32.5, 31.5, 30.12, 30.05, 27.5, 26.6, 25.2, 22.1, 22.0, 19.68, 19.67, 18.7, 18.6.

Example C

Biological Properties of Representative Gracilin a Derivatives

In this example, the biological properties of representative gracilin A derivatives of the invention are described.

Materials

Carboxymethyl dextran (CM5) sensor chips, Hank's Balance Solution Surfactant P20 (HBS-EP) buffer (pH 7.4, 0.01 M 4-(2-hydroxyethyl)-1-piperazinedsethanesulfonic acid (HEPES), 0.15 M NaCl, 3 mM EDTA, 0.005% polysorbate), amine coupling kit (1-ethyl-3-(3-dimethylaminopropyl) carbodiimide hydrochloride (EDC) and N-hydroxysuccinimide (NHS) were supplied by BiacoreAB (Uppsala, Sweden). Percoll was obtained from Pharmacia (Uppsala, Sweden). Plastic tissue-culture dishes were purchased from Falcon (Madrid, Spain). The Pan T cell Isolation Kit (human) was purchased from MiltenyiBiotec (Germany). Active human CypA full-length protein was from Abcam. Tetramethylrhodamine methyl ester (TMRM), Thiol Tracker Violet, 5-(and 6)-carboxy-2',7'-dichlorodihydrofluorescein diacetate (carboxy-H2DCFDA) and Human IL-2 ELISA kit were purchased from Thermo Fisher Scientific (Madrid, Spain). Bovine Serum Albumin (BSA) and other chemicals were reagent grade and purchased from Sigma-Aldrich (Madrid, Spain). The composition of saline solution (PBS) used for human T lymphocytes purification was (mM): 137 NaCl, 8.2 Na$_2$HPO$_4$, 1.5 KH$_2$PO$_4$, 3.2 KCl and 2 EDTA. The composition of Umbreit saline solution was (mM): NaCl 119, MgSO$_4$ 1.2, NaH$_2$PO$_4$ 1.2, NaHCO$_3$ 22.85, KCl 5.94, CaCl$_2$ 1. Glucose (1 g/L) was added to the medium. The pH was equilibrated between 7.2-7.3. Stock solutions of drugs were done in dimethylsulphoxide (DMSO).

Cell Culture

Human neuroblastoma SH-SY5Y cell line was purchased from American Type Culture Collection (ATCC), number CRL 2266. Cells were maintained in Dulbecco's Modified Eagle's medium: Nutrient Mix F-12 (DMEM/F-12) supplemented with 10% fetal bovine serum (FBS), glutamax, 100 U/mL penicillin and 100 μg/mL streptomycin at 37° C. in a humidified atmosphere of 5% CO$_2$ and 95% air. Cells were dissociated weekly using 0.05% trypsin/EDTA. All reagents were provided by Thermo Fisher Scientific.

Human T lymphocyte isolation

Peripheral lymphocytes were isolated from human fresh heparinised blood from healthy volunteers as previously described (Alfonso, A., Botana, M. A., Vieytes, M. R. and Botana, L. M. *Cell Signal*, 2001, 13, 819-826). The blood was diluted in the same proportion with PBS plus EDTA (2 mM) previously equilibrated at room temperature. 4 mL of diluted blood were placed over 3 mL of isotonic percoll (57.5%) carefully avoiding the mixture of these two phases. Once the tubes were prepared they were centrifuged at 3000 rpm, 25 min at room temperature. After centrifugation, different phases were obtained and only the fraction that contained the population of lymphocytes was collected and washed three times with PBS-EDTA to removed percoll at 1500 rpm, 10 min, room temperature. Lymphocyte purity was always higher than 80%. T lymphocytes were purified from this population with a Pan T cell Isolation Kit. This is an indirect magnetic labelling system for the isolation of untouched T cells. T cell purity was always higher than 95%. Assessment of cell purity was performed by flow cytometry using a monoclonal antibody to human CD3 labelled with FITC. Viability (>95%) was determined by trypan blue exclusion. Pure T cells were maintained in RPMI (Roswell Park Memorial Institute) 1640 plus, 10% FBS, and plated in 24 plastic tissue-culture dishes in humidified 5% CO$_2$ and 95% air atmosphere at 37° C.

Cell Viability Assay

The MTT (3-[4,5-dimethylthiazol-2-yl]-2,5-diphenyltetrazoliumbromide) assay was used to determine the cytotoxicity of gracilin derivatives in T lymphocytes (Burton, J. D. *Methods Mol. Med.*, 2005, 110, 69-78) and SH-SY5Y cells and the protective effect of these compounds against H$_2$O$_2$ insult in neuroblastoma cells as previously described (Leiros, M., Alonso, E., Sanchez, J. A., Rateb, M. E., Ebel, R., Houssen, W. E., Jaspars, M., Alfonso, A. and Botana, L. M. *ACS Chem. Neurosci.*, 2014, S, 71-80). Human T lymphocytes were cultured in 24 well plates at the concentration of 2.5×106 cells/mL and exposed to different compound concentrations (0.01, 0.1, 1 and 10 μM) added to the culture medium. Human T cells were maintained in the presence of the pure compound at 37° C. in humidified 5% CO$_2$/95% air atmosphere for 48 h.

Saponin was used as cellular death control and its absorbance was subtracted from the other data. After the incubation period with compounds, assay was performed. First cells were centrifuged (1500 rpm, 5 min, 4° C.). The pellets were resuspended in saline solution with MTT (250 μg/mL) and then incubated at 37° C. during 30 min. After washing off excess MTT twice with saline solution, cells were disaggregated with $H_2O$ and sonicated for 1 min and the absorbance of the colored formazan salt was measured at 595 nm in a spectrophotometer plate reader. All experiments were performed three times.

SH-SY5Y cells were seeded in 96-well plates at a density of $2.5 \times 10^5$ cells/mL and allowed to adhere for 24 h. At first, cells were treated only with compounds at concentrations ranging from 10-0.01 μM for 24 h to determine their possible cytotoxic effects. Experiments were carried out three times. For neuroprotective experiments, cells were treated with compounds at non-toxic concentrations (1 μM→1 nM) and 150 μM $H_2O_2$ for 6 h. Briefly, cells were washed three times with saline solution and 200 μL of MTT (500 μg/mL) dissolved in saline buffer were added to each well. Following 1 h of incubation at 37° C., the cells were disaggregated with sodium dodecyl sulphate at 5%. Absorbance of formazan crystals was measured at 595 nm with a spectrophotometer plate reader. Saponin was used as death control and its absorbance was subtracted from the other data. All experiments were performed four times.

Binding Experiments: Surface Activation, Ligand Immobilization and Binding

A Biacore X SPR biosensor with Control Software and BIA evaluation software version 3.0 from Biacore (GE Healthcare, Uppsala, Sweden) was used to check the binding between molecules. Sensor surface activation and ligand immobilization were performed by using HBS-EP as running buffer at a flow rate of 5 μL/min and 25° C. CM5 sensor chips were used as surface where Cyp A or D was immobilized as ligand. The CM5 chip is a glass slide coated with a thin layer of gold with a matrix of carboxymethylated dextran covalently attached. The CM5 chip was activated using an amine coupling kit. Following manufacture instructions, a mixture (1:1, v/v) of EDC and NHS was applied for 2 min over the sensor chip. After activation, the ligand, 100 μg/mL of active human CypA protein dissolved in sodium acetate 10 mM at pH 4.5 was added to be immobilized over a CM5 sensor chip. Finally ethanolamine-HCl was injected to deactivate the remaining active esters and to avoid non-specific binding. Next, analytes (CsA as positive control or synthetic compounds) were added to check the binding between them and CypA. Once analytes were tested and interaction was observed, individual binding curves were analyzed by determining the kinetic constants of analytes-CypA binding, namely, the observed rate constant ($K_{obs}$), the association rate constant ($K_{ass}$), the dissociation rate constant ($K_{diss}$), and the kinetic equilibrium dissociation constant ($K_D$). At equilibrium, by definition, $K_{diss}/K_{ass}=K_D$. The pseudo-first order association rate constants $K_{obs}$ ($s^{-1}$) were determined for each compound concentration by using the 1:1 Langmuir association model of BiaEvaluation software (BiaCore, Uppsala, Sweden). Then a representation of $K_{obs}$ against the corresponding concentration of each compound was done. These plots follow a linear correlation coefficient. From the equation of these representations, $K_{ass}$, $M^{-1}$ $s^{-1}$, gradient of the plot, and $K_{diss}$, $s^{-1}$, intercept of the plot was obtained. Within these two values, the kinetic equilibrium dissociation constant $K_D$ for each analyte-CypA binding was obtained.

The duration of the sample injection was 2 min at 10 μL/min flow rate. Next, dissociation of bound molecules in HBS-EP buffer flow was studied. The bound drugs were removed from the chip surface before the next injection by adding 1 M Glycine-HCl at pH 2.5 for 1 min. The association phase was used to quantify the compound-CypA or D interactions. All experiments were performed four times.

Interleukin 2 release

Human T lymphocytes at the concentration of $1 \times 10^6$ cells/mL were plated in 24 well plates and pre-treated for 2 hours with gracilin derivatives at a concentration that did not produce cell viability decrease determined by MTT test. Then, cells were stimulated with Concanavalin A (Con A) at 50 μg/mL for 48 h to induce IL-2 release. The amount of IL-2 released to the culture medium was evaluated using Human IL-2 ELISA kit. Experiments were carried out four times.

Mitochondrial Membrane Potential Measurement

The mitochondrial membrane potential (ΔΨm) was assessed using the tetramethylrhodamine methyl ester (TMRM) probe. SH-SY5Y cells were seeded in 96-well plates at $2.5 \times 10^5$ cells/mL. After 24 h, cells were treated with compounds at different concentrations (1 μM→1 nM) and 150 μM $H_2O_2$ for 6 h. Then, cells were washed twice with saline solution and 1 μM TMRM was added to each well for 30 min at 37° C. After this time, cells were solubilized with DMSO and $H_2O$ at 50%. The fluorescence was monitored with a spectrophotometer plate reader (535 nm excitation and 590 nm emission). All experiments were performed four times.

Determination of Intracellular ROS Levels

Intracellular levels of reactive oxygen species (ROS) were determined with carboxy-H2DCFDA (5-(and-6)-carboxy-2',7'-dichlorodihydrofluorescein diacetate). This dye diffuses through the cellular membrane and is converted by cellular esterases to carboxy-H2DCFH (non-fluorescent). When carboxy-H2DCFH is oxidized by ROS, it becomes fluorescent (Halliwell, B. and Whiteman, M. *Br. J. Pharmacol.*, 2004, 142, 231-255). Cells were seeded at a density of $2.5 \times 10^5$ cells/mL in 96-well plates and allowed to attach for 24 h. Following treatment with compounds at various concentrations (1 μM→1 nM) and 150 μM $H_2O_2$ for 6 h, SH-SY5Y cells were washed twice with serum-free culture medium. Then, carboxy-H2DCFDA 20 μM dissolved in serum-free culture medium was added to each well and the cells were incubated for 1 h at 37° C. After this incubation, the medium with the fluorescent dye was replaced with PBS and the plate was incubated for 30 min at 37° C. Fluorescence was read at 527 nm, with an excitation wavelength of 495 nm. All experiments were performed four times.

Glutathione Assay

Glutathione (GSH) levels were determined using Thiol Tracker Violet dye, which reacts with reduced thiols in cells. Reduced glutathione represents the majority of intracellular free thiols, so this probe can be used to estimate its levels in cells. Measurements were performed following manufacturer's protocol. Cells were seeded in 96-well plates at $2.5 \times 10^5$ cells/mL for 24 h and treated with compounds at various concentrations (1 μM→1 nM) and 150 μM $H_2O_2$. After 6 h, SH-SY5Y cells were washed twice with PBS and loaded with 100 μL of prewarmed Thiol Tracker Violet dye (10 μM) for 30 min at 37° C. The fluorescence was measured at 404 nm excitation and emission at 526 nm. All experiments were performed four times.

Mitochondrial Membrane Permeability Transition Pore (mPTP) Measurement

The blockage of mPTP by compounds was determined with the MitoProbe Transition Assay Kit following manufacturer's instructions. Briefly, SH-SY5Y human neuroblastoma cells were re-suspended in pre-warmed PBS/Ca$^{+2}$ buffer at a final concentration of 1×10$^6$ cells/mL. Cells were loaded with 0.01 µM Calcein-AM and incubated at 37° C. for 15 min. Then, 0.4 mM CoCl$_2$ and compounds at selected concentrations were added and incubated for 15 min at 37° C. Cyclosporine A (CsA) at 0.2 µM was used as positive control. After this incubation, cells were centrifuged and re-suspended in 100 µL of PBS. Just before analyzing, 1 mM tert-butyl hydroperoxide (TBHP) was added to the samples to induce pore opening. Fluorescence intensity was measured at 488 nm excitation and 517 nm emission wavelengths by flow cytometry using the ImageStreamMKII (Amnis Corporation, Merck-Millipore) and INSPIRER software. The fluorescence of 10,000 events was analyzed with IDEASR Application vs 6.0 (Amnis Corporation, Merck-Millipore). Experiments were carried out four times.

CypD Enzyme Inhibition Assay

The inhibition of the peptidyl-prolyl cis-trans isomerase (PPIase) activity of compounds was determined by following the rate of hydrolysis of N-succinyl-Ala-Ala-Pro-Phe-pnitroanilide by chymotrypsin. CsA was used as positive control. The assay was performed as previously described (Yan, W., Qing, J., Mei, H., Nong, J., Huang, J., Zhu, J., Jiang, H., Liu, L., Zhang, L. and Li, J. *Bioorg. Med. Chem. Lett.*, 2015, 25, 5682-5686) with small modifications. The assay buffer (20 mM Tris-HCl, 50 mM NaCl, pH 7.8), CypD (1 nM) and the compounds at concentrations ranging from 0.001 to 10 µM were pre-cooled at 4° C. for 1 h. After that time, chymotrypsin at 0.4 mg/mL in 1 mM HCl was added to each well. The reaction was initiated by the addition of the peptide (0.1 mg/mL in 500 mM LiCl in THF). The absorbance at 380 nm was monitored every 30 sec for 5 min with a spectrophotometer plate reader. The blank rates of hydrolysis (in absence of CypD) were subtracted from the rates in the presence of the enzyme. The half-maximal inhibitory concentration (IC$_{50}$) was calculated by fitting the data with a log(inhibitor) vs. response model of GraphPad Prism 5.0 software. All experiments were performed four times.

Statistical Analyses

Data are presented as mean±SEM. Differences were evaluated by one way ANOVA with Dunnett's post hoc analysis. Statistical significance was considered at p<0.05.

While illustrative embodiments have been illustrated and described, it will be appreciated that various changes can be made therein without departing from the spirit and scope of the invention.

The invention claimed is:

1. A method for suppressing an immune response in a subject, the method comprising administering to a subject in need thereof an effective amount of a compound having the formula:

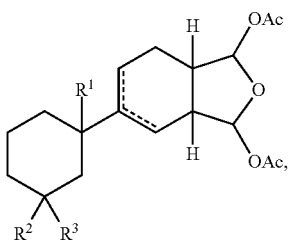

or a stereoisomer or racemate thereof, wherein:
R$^1$, R$^2$, and R$^3$ are independently H or C1-C3 alkyl, and the dashed line denotes a bond or an absence of a bond, with the proviso that only one dashed line is a bond.

2. The method of claim 1, wherein the compound is:

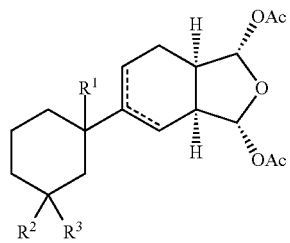

or a stereoisomer or racemate thereof.

3. The method of claim 1, wherein the compound is:

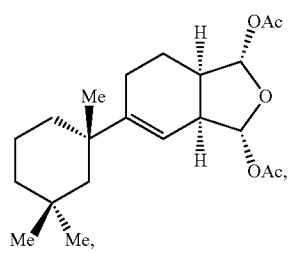

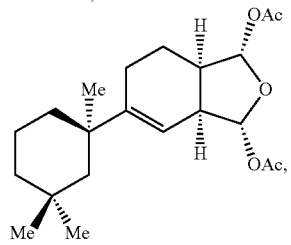

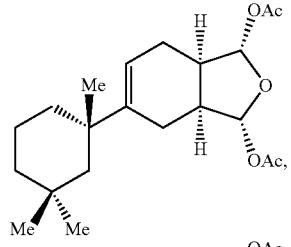

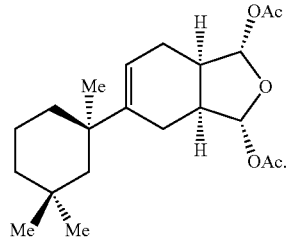

4. The method of claim 1, wherein the subject has been diagnosed as suffering from an autoimmune disease or an inflammatory disease.

5. The method of claim 1, wherein the compound inhibits interleukin-2 production.

6. The method of claim 5, wherein the interleukin-2 production is inhibited by greater than about 20%.

7. The method of claim 1, wherein the compound binds to CypA with a K$_D$ of less than about 6 µM.

8. The method of claim 1, wherein the compound reduces T-cell viability in vitro by less than about 10%.

9. A method for treating a neurodegenerative disease in a subject, the method comprising administering to a subject in need thereof an effective amount of a compound having the formula:

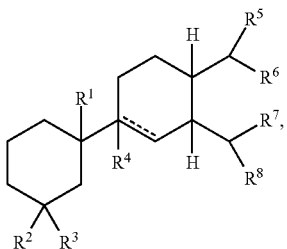

or a stereoisomer or racemate thereof, wherein:
$R^1$, $R^2$, and $R^3$ are independently H or C1-C3 alkyl;
$R^4$ is H, OH, OAc, or absent;
$R^5$ and $R^8$ are independently H or OAc;
$R^6$ and $R^7$ are H or $R^6$ and $R^7$, taken together, are O; and
the dashed line denotes a bond when $R^4$ is absent, or absence of a bond when $R^4$ is H, OH, or OAc.

10. The method of claim 9, wherein the compound is:

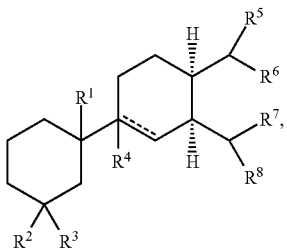

or a stereoisomer or racemate thereof.

11. The method of claim 9, wherein the compound is:

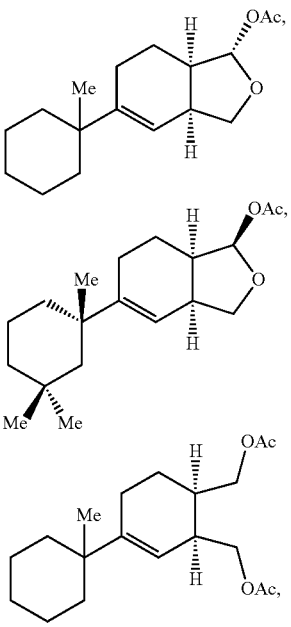

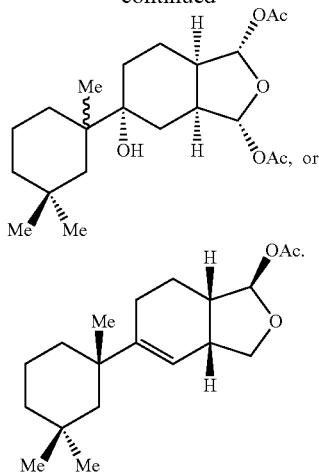

12. The method of claim 9, wherein the neurodegenerative disease is Alzheimer's disease.

13. The method of claim 9, wherein the compound inhibits CypD with an $IC_{50}$ of less than about 0.5 μM.

14. The method of claim 9, wherein the compound inhibits CypA with an $IC_{50}$ of less than about 0.3 μM.

15. The method of claim 9, wherein the compound inhibits CypD and does not inhibit CypA.

16. A compound having the formula:

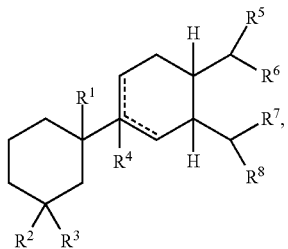

or a stereoisomer or racemate thereof, wherein:
$R^1$, $R^2$, and $R^3$ are independently H or C1-C3 alkyl;
$R^4$ is H, OH, OAc, or absent;
$R^5$ and $R^8$ are independently H or OAc;
$R^6$ and $R^7$, taken together, are O; and
the dashed line denotes a bond or absence of a bond with the proviso that only one dashed line is a bond, and with a further proviso that both dashed lines denote absence of a bond when $R^4$ is H, OH, or OAc.

17. The compound of claim 16, wherein the compound is:

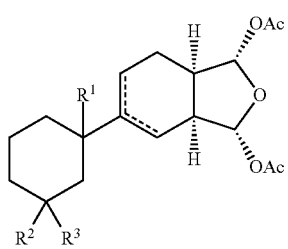

or a stereoisomer or racemate thereof.

18. The compound of claim 16 selected from the group consisting of:

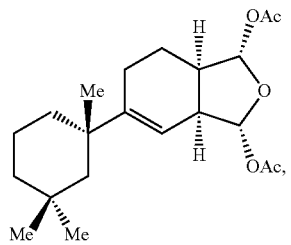
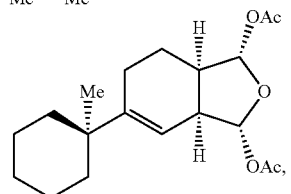
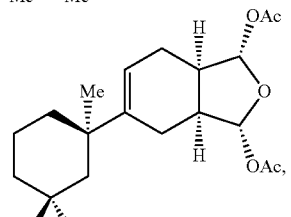
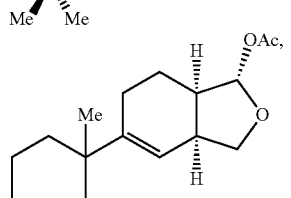
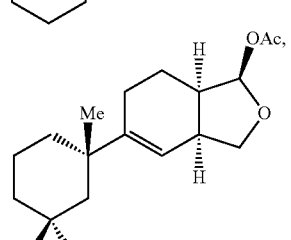
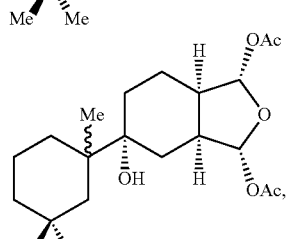
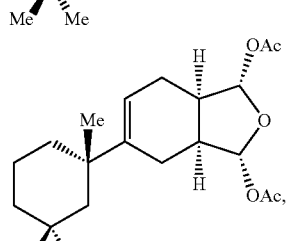

-continued

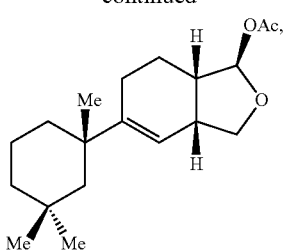
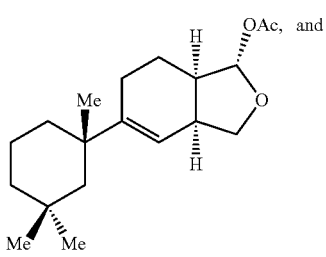
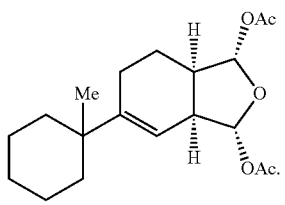

19. A pharmaceutical composition, comprising a compound of claim 16 and a pharmaceutically acceptable carrier.

20. A method for suppressing an immune response in a subject, the method comprising administering to a subject in need thereof an effective amount of a compound having the formula:

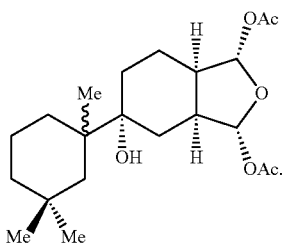

21. A compound having the formula:

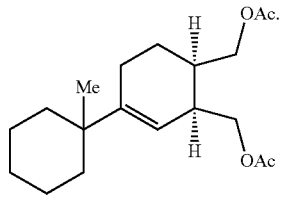 [SMILES: CC(=O)OC[C@@H]1CCC(C2(C)CCCCC2)=C[C@@H]1COC(C)=O]

22. A pharmaceutical composition, comprising a compound of claim 21 and a pharmaceutically acceptable carrier.

* * * * *